(12) United States Patent
Dervieux et al.

(10) Patent No.: US 7,582,282 B2
(45) Date of Patent: Sep. 1, 2009

(54) METHODS FOR OPTIMIZING CLINICAL RESPONSIVENESS TO METHOTREXATE THERAPY USING METABOLITE PROFILING AND PHARMACOGENETICS

(75) Inventors: Thierry Dervieux, San Diego, CA (US); Michael Walsh, San Diego, CA (US)

(73) Assignee: Prometheus Laboratories Inc., San Diego, CA (US)

( * ) Notice: Subject to any disclaimer, the term of this patent is extended or adjusted under 35 U.S.C. 154(b) by 565 days.

(21) Appl. No.: 10/927,904

(22) Filed: Aug. 26, 2004

(65) Prior Publication Data

US 2005/0112627 A1 May 26, 2005

Related U.S. Application Data

(60) Provisional application No. 60/514,423, filed on Oct. 24, 2003, provisional application No. 60/560,752, filed on Aug. 29, 2003.

(51) Int. Cl.
*G01N 33/68* (2006.01)
(52) U.S. Cl. .......................... 424/9.2; 436/86; 436/161; 436/171; 436/172; 436/173
(58) Field of Classification Search ........................ None
See application file for complete search history.

(56) References Cited

U.S. PATENT DOCUMENTS 6,921,667 B2 * 7/2005 Dervieux et al. .............. 436/63
2005/0112627 A1 * 5/2005 Dervieux et al. .............. 435/6

FOREIGN PATENT DOCUMENTS

WO      01/65994 A      9/2001

OTHER PUBLICATIONS

Dervieux et al, Clinical Chemistry.*
The Merck Index, Tenth Edition, Merck & Co., Inc., 1983, pp. 859-860.*
Allegra et al., "Inhibition of phosphoribosylaminoimicazolecarbixamide transformylase by methotrexate and dihydrofolic acid polyglutamates," *Proc. Natl. Acad. Sci. USA*, 82:4881-85 (1985).
Angelis-Stoforidis et al., "Methotrexate polyglutamate levels in circulating erythrocytes ad polymorphs correlate with clinical efficacy in rheumatoid arthritis," *Clin. Exp. Rheumatol*, 17:313-320 (1999).
Baggott et al., "Inhibition of 5-aminoimidazole-4-carboxamide ribotide transformylase, adenosine deaminase and 5'-adenylate deaminase by polyglutamates of methotrexate and oxidized folates and by 5-aminoimidazole-4-carboxamide riboside and ribotide," *Biochem. J.* 236:193-200 (1986).

(Continued)

*Primary Examiner*—David A Saunders
(74) *Attorney, Agent, or Firm*—Cooley Godward Kronish LLP

(57) ABSTRACT

The present invention provides methods for optimizing clinical responsiveness to chemotherapy in an individual through genotypic analysis of polymorphisms in at least one gene. The methods of the present invention may further comprise determining the level of at least one long-chain methotrexate polyglutamate (MTXPG) in a sample obtained from the individual. The present invention also provides methods for generating a pharmacogenetic index for predicting clinical responsiveness to chemotherapy in an individual through genotypic analysis of polymorphisms in at least one gene. In addition, the present invention provides methods for optimizing therapeutic efficacy of chemotherapy in an individual by calculating the level of at least one long-chain MTXPG in a sample obtained from the individual.

28 Claims, 21 Drawing Sheets

OTHER PUBLICATIONS

Chabner et al., "Polyglutamation of methotrexate. Is methotrexate a prodrug?" *J. Clin. Invest*, 76:907-912 (1985).

Chango et al., "A polymorphism (80G->A) in the reduced folate carrier gene and its associations with folate status and homocysteinemia," *Mol. Genet. Metab*. 70:310-315 (2000).

Chladek et al., "Pharmacokinetics of low doses of methotrexate in patients with psoriasis over the early period of treatment," *Eur. J. Clin, Pharmacol*, 53:437-444 (1998).

Cronstein et al., "Methotrexate inhibits neutrophil function stimulating adenosine release from connective tissue cells," *Proc. Natl. Acad. Sci. USA* 88:2441-2445 (1991).

Cronstein et al., "The anti-inflammatory mechanism of methotrexate. Increased adenosine release at inflamed sites diminishes leukocyte accumulation in an in vivo model of inflammation," *J. Clin. Invest*. 92:2675-2682 (1993).

Dervieux et al., "De novo purine synthesis inhibition and antileukemic effects of mercaptopurine alone or in combination with methotrexate in vivo," *Blood* 100:1240-1247 (2002).

Kamen and Winick, "Analysis of methotrexate polyglutamate derivatives in vivo," *Methods Enzymol*. 122:339-346 (1986).

Kamen et al., "A rapid, radiochemical-ligand binding assay for methotrexate," *Anal. Biochem*. 70:54-63 (1976).

Laverdiere et al., "Polymorphism G80A in the reduced folate carrier gene and its relationship to methotrexate plasma levels and outcome of childhood acute lymphoblastic leukemia," *Blood* 100:3832-34 (2002).

Masson et al., "Accumulation of methotrexate polyglutamates in lymphoblasts is a determinant of antileukemic effects in vivo. A rationale for high-dose methotrexate," *J. Clin. Invest*. 97:73-80 (1996).

Matherly, "Molecular and cellular biology of the human reduced folate carrier," *Progress in Nucleic Acid Research and Molecular Biology* 67: 131-162 (2001).

Montesinos et al., "Adenosine A2A or A3 receptors are required for inhibition of inflammation by methotrexate and its analog MX-68," *Arthritis Rheum*. 48:240-247 (2003).

Morabito et al., "Methotrexate and sulfasalazine promote adenosine release by a mechanism that requires ecto5'-nucleotidase-mediated conversion of adenine nucleotides," *J.Clin. Invest*. 101:295-300 (1998).

Ortendahl et al., "The methotrexate therapeutic response in rheumatoid arthritis," *J. Rheumatol*. 29:2084-2091 (2002).

Rayl et al., "The human purH gene product, 5-aminoimidazole-4carboxamide ribonucleotide formyltransferase/IMP cyclohydrolase. Cloning, sequencing, expression, purification, kinetic analysis, and domain mapping," *J. Biol. Chem*. 271:2225-2233 (1996).

Relling and Dervieux, "Pharmacogenetics and cancer therapy," *Nat. Rev. Cancer* 1:99-108 (2001).

Schmiegelow et al., "Risk of relapse in childhood acute lymphoblastic leukemia is related to RBC methotrexate and mercaptopurine metabolites during maintenance chemotherapy. Nordic Society for Pediatric Hematology and Oncology," *J. Clin. Oncol*. 13:345-351 (1995).

Schroder and Heinsvig, "Enzymatic assay for methotrexate in erythrocytes," *Scand. J. Clin. Lab. Invest* . 45:657-659 (1985).

Vergis et al., "Human 5-aminoimidazole-4-carboxamide ribonucleotide transformylase/inosine 5'-monophosphate cyclohydrolase. A bifunctional protein requiring dimerization for transformylase activity but not for cyclohydrolase activity," *J. Biol. Chem*. 276:7727-7733 (2001).

Walker et al., "Determinants of serious liver disease among patients receiving low-dose methotrexate for rheumatoid arthritis," *Arthritis Rheum*, 36:329-335 (1993).

Weinblatt et al., "Methotrexate in rheumatoid arthritis. A five-year prospective multicenter study," *Arthritis Rheum*, 37:1492-1498 (1994).

Weinblatt et al., "Efficacy of low-dose methotrexate in rheumatoid arthritis," *Eng. J. Med*, 312:818-822 (1985).

Whetstine et al., "Single nucleotide polymorphisms in the human reduced folate carrier: Characterization of a high-frequency G/A variant at position 80 and transport properties of the $His^{27}$ and $Arg^{27}$ carriers," *Clin. Cancer Res*. 7: 3416-3422 (2001).

Genbank Accession No. AH006305.
Genbank Accession No. NC_003283.
Genbank Accession No. NM_003056.
Genbank Accession No. NM_004044.
Genbank Accession No. U92868.
Genbank Accession No. U92869.
Genbank Accession No. U92870.
Genbank Accession No. U92871.
Genbank Accession No. U92872.
Genbank Accession No. U92873.
Genbank Accession No. Z75532.

Dervieux, et al.; "Effect of methotrexate polyglutamates on thioguanine nucleotide concentrations during continuation therapy of acute lymphoblastic leukemia with mercaptopurine;" *Leukemia*; 16, 209-212 (2002).

Hendel et al.; "Pharmacokinetics of Methotrexate in Erythrocytes in Psoriasis;" *European Journal of Clinical Pharmacology*; 27: 607-610; (1984).

Kamen, et al.; "Methotrexate Accumulation and Folate Depletion in Cells as a Possible Mechanism of Chronic Toxicity to the Drug;" *British Journal of Haematology*; 49, 355-360 (1981).

Lena et al.; "Kinetics of Methotrexate and Its Metabolites in Red Blood Cells;" *Cancer Drug Delivery*; vol. 4, No. 2: 119-127; (1987).

Schmiegelow et al.; "Myelotoxicity, Pharmacokinetics, and Relapse Rate with Methotrexate/6-Mercaptopurine Maintenance Therapy of Childhood Acute Lymphoblastic Leukemia;" *Pediatric Hematology and Oncology*; 13:433-441; (1996).

Schroder, et al.; "Methotrexate and its polyglutamate derivatives in erythrocytes during and after weekly low-dose oral methotrextae therapy of children with acute lymphoblastic leukemia;" *Cancer Chemother Pharmacol*; 21: 145-149; (1988).

Schroder, et al.; "In vivo decline of methotrexate and methotrexate polyglutamates in age-fractionated erythrocytes;" *Cancer Chemother Pharmacol*; 21: 150-155; (1988).

T. Dervieux; Polyglutamation of Methotrexate With Common Polymorphisms in Reduced Folate Carrier, Aminoimidazole Carboxamide Ribonucleotide Transformylase, and Thymidylate Synthase are Associated With Methotrexate Effects in Rheumatoid Arthritis; *Arthritis & Rheumatism*; vol. 50, No. 9, previously presented 2766-2774 (2004).

Belkov et al.; Reduced Folate Carrier Expression in Acute Lymphoblastic Leukemia: A Mechanism for Ploidy but not Lineage Differences in Methotrexate Accumulation; *Blood*; vol. 93, No. 5; previously presented 1643-1650 (1999).

C. Skibola, et al.; Polymorphisms in the thymidylate synthase and serine hydroxymethyltransferase genes and risk of adult acute lymphocytic leukemia; *Blood*; vol. 99, No. 10: 3786-3791; (2002).

K. Chave, et al.; Identification of single nucleotide polymorphisms in the human γ-glutamyl hydrolase gene and characterization of promoter polymorphisms; *Gene*; 319: 167-175; (2003).

J. Ma et al.; A Polymorphism of the Methionine Synthase Gene: Association with Plasma Folate, Vitamin B12, Homocyst(e)ine, and Colorectal Cancer Risk; *Cancer Epidemiology, Biomarkers and Prevention*; vol. 8, 825-829 (1999).

A. Ulvik et al.; Single Nucleotide Polymorphism (SNP) Genotyping in Unprocessed WShole Blood and Serum by Real-Time PCR: Application to SNPs Affecting Homocysteine and Folate Metabolism; *Clinical Chemistry*; vol. 47, 2050-2053; (2001).

Chiusolo, P. "Preponderance of methylenetetrahydrofolate reductase C677T homozygosity among leukemia patients intolerant to methotrexate," Annals of Oncology, 2002, vol. 13, pp. 1915-1918.

Evans, William "Differing effects of methylenetetrahydrofolate reductase single nucleotide polymorphisms on methotrexate efficacy and toxicity in rheumatoid arthritis," Pharmacogenetics, 2002, vol. 12, No. 3, pp. 181-182.

Laverdiere, Caroline, et al. "Polymorphism $G^{80}A$ in the reduced folate carrier gene and its relationship to methotrexate plasma levels and outcome of childhood acute lymphoblastic leukemia," Blood, 2002, vol. 100, No. 10, pp. 3832-3834.

Masson, Eric, et al. "Accumulation of Methotrexate Polyglutamates in Lymphoblasts is a Determinant of Antileukemic Effects in Vivo," J. Clin. Invest. 1996, vol. 97, No. 1, pp. 73-80.

Ranganathan, Prabha, et al. "Methotrexate Pharmacogenetics *The First Step Toward Individualized Therapy in Rheumatoid Arthritis*," Arthritis & Rheumatism, 2006, vol. 54, No. 5, pp. 1366-1377.

Urano, W. et al., "Polymorphisms in the methylenetetrahydrofolate reductase gene were associated with both the efficacy and the toxicity of methotrexate used for the treatment of rheumatoid arthritis, as evidence by single locus and haplotype analyses," Pharmacogenetics, 2002, vol. 12, No. 3, pp. 183-190.

Supplemental European Search Report dated Oct. 7, 2008; Int'l App. No. PCT/US2004027851.

Sierra E. et al., Recent advances in the understanding of the mechanism of membrane transport of folates and antifolates, Seminars in Oncology, vol. 26, No. 2, pp. 11-23 (1999).

Takemura Yuzuru et al., Cellular and molecular mechanisms of resistance to antifolate drugs: New analogues and approaches to overcome the resistance, International Journal of Hematology, vol. 66, No. 4, pp. 459-477 (1997).

Bosson Geoffrey, Reduced folate carrier: Biochemistry and molecular biology of the normal and methotrexate-resistant cell, British Journal of Biomedical Science, vol. 60, No. 2, pp. 117-129 (2003).

Iqbal Syma et al., Targeted therapy and pharmacogenomic programs, Cancer, vol. 97, No. 8 Supplement, pp. 2076-2082 (2003).

\* cited by examiner

Methotrexate

Methotrexate polyglutamates

A.

B.

C.

D.

E.

A.

B. Methotrexate Polyglutamates, Pharmacogenetic Index and Response

Pharmacogenetic Index = RFC80AA + ATIC 347G + TSER*2

A.

```
   1 ggcacgaggc cgctcgccct gaacccagtg cctgcagcca tggctcccgg ccagctcgcc
  61 ttatttagtg tctctgacaa aaccggcctt gtggaatttg caagaaacct gaccgctctt
 121 ggtttgaatc tggtcgcttc cggagggact gcaaaagctc tcagggatgc tggtctggca
 181 gtcagagatg tctctgagtt gacgggattt cctgaaatgt tgggggacg tgtgaaaact
 241 ttgcatcctg cagtccatgc tggaatccta gctcgtaata ttccagaaga taatgctgac
 301 atggccagac ttgatttcaa tcttataaga gttgttgcct gcaatctcta tccctttgta
 361 aagacagtgg ctttctccagg tgtaactgtt gaggaggctg tggagcaaat tgacattggt
 421 ggagtaacct tactgagagc tgcagccaaa aaccacgctc gagtgacagt ggtgtgtgaa
 481 ccagaggact atgtggtggt gtccacggag atgcagagct ccgagagtaa ggacacctcc
 541 ttggagacta gacgccagtt agccttgaag gcattcactc atacggcaca atatgatgaa
 601 gcaatttcag attatttcag gaaacagtac agcaaaggcg tatctcagat gcccttgaga
 661 tatggaatga acccacatca gaccctgcc cagctgtaca cactgcagcc aagcttccc
 721 atcacagttc taaatggagc cctggatt ataaacttgt gcgatgcttt gaacgcctgg
 781 cagctggtga aggaactcaa ggaggcttta ggtattccag ccgctgcctc tttcaaacat
 841 gtcagcccag caggtgctgc tgttggaatt ccactcagtg aagatgaggc caagtctgc
 901 atggtttatg atctctataa aaccctcaca cccatctcag cggcatatgc aagagcaaga
 961 ggggctgata ggatgtcttc atttggtgat tttgttgcat tgtccgatgt ttgtgatgta
1021 ccaactgcaa aaattatttc cagagaagta tctgatggta taattgcccc aggatatgaa
1081 gaagaagcct tgacaatact ttccaaaaag aaaaatggaa actattgtgt cctcagatg
1141 gaccaatctt acaaaccaga tgaaaatgaa gttcgaactc tctttggtct tcatttaagc
1201 cagaagagaa ataatggtgt cgtcgacaag tcattattta gcaatgttgt taccaaaaat
1261 aaagatttgc cagagtctgc cctcgagac ctcatcgtag ccaccattgc tgtcaagtac
1321 actcagtcta actctgtgtg ctacgccaag aacgggcagg ttatcggcat tggagcagga
1381 cagcagtctc gtatacactg cactcgcctt gcaggagata aggcaaacta ttggtggctt
1441 agacaccatc cacaagtgct ttcgatgaag tttaaaacag gagtgaagag agcagaaatc
1501 tccaatgcca tcgatcaata tgtgactgga accattggcg aggatgaaga tttgataaag
1561 tggaagcac tgtttgagga agtccctgag ttactcactg aggcagagaa gaaggaatgg
1621 gttgagaaac tgactgaagt ttctatcagc tctgatgcct tcttcccttt ccgagataac
1681 gtagacagag ctaaaaggag tggtgtgcg tacattgcgg ctccctccgg ttctgctgct
1741 gacaaagttg tgattgaggc ctgcgacgaa ctgggaatca tcctcgctca tacgaacctt
1801 cggctcttcc accactgatt ttaccacaca ctgtttttg gcttgcttat gtgtaggtga
1861 acagtcacgc ctgaaacttt gaggataact ttttaaaaaa ataaaacagt atctcttaaa
1921 aaaaaaaaaa aaaaaaaaaa aaaaa
```

B.

```
                 MAPGQLALFSVSDKTGLVEFARNLTALGLNLVASGGTAKALRDA
GLAVRDVSELTGFPEMLGGRVKTLHPAVHAGILARNIPEDNADMARLDFNLIRVVACN
LYPFVKTVASPGVTVEEAVEQIDIGGVTLLRAAAKNHARVTVVCEPEDYVVVSTEMQS
SESKDTSLETRRQLALKAFTHTAQYDEAISDYFRKQYSKGVSQMPLRYGMNPHQTPAQ
LYTLQPKLPITVLNGAPGFINLCDALNAWQLVKELKEALGIPAAASFKHVSPAGAAVG
IPLSEDEAKVCMVYDLYKTLTPISAAYARARGADRMSSFGDFVALSDVCDVPTAKIIS
REVSDGIIAPGYEEEALTILSKKKNGNYCVLQMDQSYKPDENEVRTLFGLHLSQKRNN
GVVDKSLFSNVVTKNKDLPESALRDLIVATIAVKYTQSNSVCYAKNGQVIGIGAGQQS
RIHCTRLAGDKANYWWLRHHPQVLSMKFKTGVKRAEISNAIDQYVTGTIGEDEDLIKW
KALFEEVPELLTEAEKKEWVEKLTEVSISSDAFFPFRDNVDRAKRSGVAYIAAPSGSA
ADKVVIEACDELGIILAHTNLRLFHH"
```

FIG. 20

SEQUENCE LISTING

```
<160> NUMBER OF SEQ ID NOS: 16

<210> SEQ ID NO 1
<211> LENGTH: 1945
<212> TYPE: DNA
<213> ORGANISM: Homo sapiens
<220> FEATURE:
<223> OTHER INFORMATION: aminoimidazole carboxamide ribonucleotide
      transformylase, 5-aminoimidazole-4-carboxamide
      ribonucleotide formyltransferase (ATIC)

<400> SEQUENCE: 1
ggcacgaggc cgctcgccct gaacccagtg cctgcagcca tggctcccgg ccagctcgcc      60
ttatttagtg tctctgacaa aaccggcctt gtggaatttg caagaaacct gaccgctctt     120
ggtttgaatc tggtcgcttc cggagggact gcaaaagctc tcagggatgc tggtctggca     180
gtcagagatg tctctgagtt gacgggattt cctgaaatgt tgggggacg tgtgaaaact      240 ttgcatcctg cagtccatgc tggaatccta gctcgtaata ttccagaaga taatgctgac     300
atggccagac ttgatttcaa tcttataaga gttgttgcct gcaatctcta tccctttgta     360
aagacagtgg cttctccagg tgtaactgtt gaggaggctg tggagcaaat tgacattggt     420
ggagtaacct tactgagagc tgcagccaaa aaccacgctc gagtgacagt ggtgtgtgaa     480
ccagaggact atgtggtggt gtccacggag atgcagagct ccgagagtaa ggacacctcc     540
ttggagacta gacgccagtt agccttgaag gcattcactc atacggcaca atatgatgaa     600
gcaatttcag attatttcag gaaacagtac agcaaaggcg tatctcagat gcccttgaga     660
tatggaatga acccacatca gaccccctgcc cagctgtaca cactgcagcc caagcttccc     720
atcacagttc taaatggagc ccctggattt ataaacttgt gcgatgcttt gaacgcctgg     780
cagctggtga aggaactcaa ggaggcttta ggtattccag ccgctgcctc tttcaaacat     840
gtcagcccag caggtgctgc tgttggaatt ccactcagtg aagatgaggc caaagtctgc     900
atggtttatg atctctataa aaccctcaca cccatctcag cggcatatgc aagagcaaga     960
ggggctgata ggatgtcttc atttggtgat tttgttgcat tgtccgatgt ttgtgatgta    1020
ccaactgcaa aaattatttc cagagaagta tctgatggta taattgcccc aggatatgaa    1080
gaagaagcct tgcaatact ttccaaaaag aaaaatggaa actattgtgt ccttcagatg    1140
gaccaatctt acaaaccaga tgaaaatgaa gttcgaactc tctttggtct tcatttaagc    1200
cagaagagaa ataatggtgt cgtcgacaag tcattattta gcaatgttgt taccaaaaat    1260
```

-continued

```
aaagatttgc cagagtctgc cctccgagac ctcatcgtag ccaccattgc tgtcaagtac    1320
actcagtcta actctgtgtg ctacgccaag aacgggcagg ttatcggcat ggagcagga    1380 cagcagtctc gtatacactg cactcgcctt gcaggagata aggcaaacta ttggtggctt    1440
agacaccatc cacaagtgct tcgatgaag tttaaaacag gagtgaagag agcagaaatc    1500
tccaatgcca tcgatcaata tgtgactgga accattggcg aggatgaaga tttgataaag    1560
tggaaggcac tgtttgagga agtccctgag ttactcactg aggcagagaa gaaggaatgg    1620
gttgagaaac tgactgaagt ttctatcagc tctgatgcct tcttcccttt ccgagataac    1680
gtagacagag ctaaaaggag tggtgtggcg tacattgcgg ctccctccgg ttctgctgct    1740
gacaaagttg tgattgaggc ctgcgacgaa ctgggaatca tcctcgctca tacgaacctt    1800
cggctcttcc accactgatt ttaccacaca ctgttttttg gcttgcttat gtgtaggtga    1860
acagtcacgc tgaaacttt gaggataact ttttaaaaaa ataaaacagt atctcttaaa    1920
aaaaaaaaaa aaaaaaaaa aaaaa                                            1945
```

<210> SEQ ID NO 2
<211> LENGTH: 592
<212> TYPE: PRT
<213> ORGANISM: Homo sapiens
<220> FEATURE:
<223> OTHER INFORMATION: aminoimidazole carboxamide ribonucleotide transformylase, 5-aminoimidazole-4-carboxamide ribonucleotide formyltransferase (ATIC)

<400> SEQUENCE: 2

```
Met Ala Pro Gly Gln Leu Ala Leu Phe Ser Val Ser Asp Lys Thr Gly
  1               5                  10                  15

Leu Val Glu Phe Ala Arg Asn Leu Thr Ala Leu Gly Leu Asn Leu Val
             20                  25                  30

Ala Ser Gly Gly Thr Ala Lys Ala Leu Arg Asp Ala Gly Leu Ala Val
         35                  40                  45

Arg Asp Val Ser Glu Leu Thr Gly Phe Pro Glu Met Leu Gly Gly Arg
     50                  55                  60

Val Lys Thr Leu His Pro Ala Val His Ala Gly Ile Leu Ala Arg Asn
 65                  70                  75                  80

Ile Pro Glu Asp Asn Ala Asp Met Ala Arg Leu Asp Phe Asn Leu Ile
                 85                  90                  95

Arg Val Val Ala Cys Asn Leu Tyr Pro Phe Val Lys Thr Val Ala Ser
            100                 105                 110

Pro Gly Val Thr Val Glu Glu Ala Val Glu Gln Ile Asp Ile Gly Gly
        115                 120                 125

Val Thr Leu Leu Arg Ala Ala Ala Lys Asn His Ala Arg Val Thr Val
    130                 135                 140

Val Cys Glu Pro Glu Asp Tyr Val Val Val Ser Thr Glu Met Gln Ser
145                 150                 155                 160

Ser Glu Ser Lys Asp Thr Ser Leu Glu Thr Arg Arg Gln Leu Ala Leu
                165                 170                 175

Lys Ala Phe Thr His Thr Ala Gln Tyr Asp Glu Ala Ile Ser Asp Tyr
            180                 185                 190

Phe Arg Lys Gln Tyr Ser Lys Gly Val Ser Gln Met Pro Leu Arg Tyr
        195                 200                 205

Gly Met Asn Pro His Gln Thr Pro Ala Gln Leu Tyr Thr Leu Gln Pro
    210                 215                 220
```

```
Lys Leu Pro Ile Thr Val Leu Asn Gly Ala Pro Gly Phe Ile Asn Leu
225                 230                 235                 240

Cys Asp Ala Leu Asn Ala Trp Gln Leu Val Lys Glu Leu Lys Glu Ala
            245                 250                 255

Leu Gly Ile Pro Ala Ala Ser Phe Lys His Val Ser Pro Ala Gly
        260                 265                 270

Ala Ala Val Gly Ile Pro Leu Ser Glu Asp Glu Ala Lys Val Cys Met
    275                 280                 285

Val Tyr Asp Leu Tyr Lys Thr Leu Thr Pro Ile Ser Ala Ala Tyr Ala
290                 295                 300

Arg Ala Arg Gly Ala Asp Arg Met Ser Ser Phe Gly Asp Phe Val Ala
305                 310                 315                 320

Leu Ser Asp Val Cys Asp Val Pro Thr Ala Lys Ile Ile Ser Arg Glu
                325                 330                 335

Val Ser Asp Gly Ile Ile Ala Pro Gly Tyr Glu Glu Ala Leu Thr
            340                 345                 350

Ile Leu Ser Lys Lys Asn Gly Asn Tyr Cys Val Leu Gln Met Asp
        355                 360                 365

Gln Ser Tyr Lys Pro Asp Glu Asn Glu Val Arg Thr Leu Phe Gly Leu
    370                 375                 380

His Leu Ser Gln Lys Arg Asn Asn Gly Val Val Asp Lys Ser Leu Phe
385                 390                 395                 400

Ser Asn Val Val Thr Lys Asn Lys Asp Leu Pro Glu Ser Ala Leu Arg
                405                 410                 415

Asp Leu Ile Val Ala Thr Ile Ala Val Lys Tyr Thr Gln Ser Asn Ser
            420                 425                 430

Val Cys Tyr Ala Lys Asn Gly Gln Val Ile Gly Ile Gly Ala Gly Gln
        435                 440                 445

Gln Ser Arg Ile His Cys Thr Arg Leu Ala Gly Asp Lys Ala Asn Tyr
    450                 455                 460

Trp Trp Leu Arg His His Pro Gln Val Leu Ser Met Lys Phe Lys Thr
465                 470                 475                 480

Gly Val Lys Arg Ala Glu Ile Ser Asn Ala Ile Asp Gln Tyr Val Thr
                485                 490                 495

Gly Thr Ile Gly Glu Asp Glu Asp Leu Ile Lys Trp Lys Ala Leu Phe
            500                 505                 510

Glu Glu Val Pro Glu Leu Leu Thr Glu Ala Glu Lys Lys Glu Trp Val
        515                 520                 525

Glu Lys Leu Thr Glu Val Ser Ile Ser Ser Asp Ala Phe Phe Pro Phe
    530                 535                 540

Arg Asp Asn Val Asp Arg Ala Lys Arg Ser Gly Val Ala Tyr Ile Ala
545                 550                 555                 560

Ala Pro Ser Gly Ser Ala Ala Asp Lys Val Val Ile Glu Ala Cys Asp
                565                 570                 575

Glu Leu Gly Ile Ile Leu Ala His Thr Asn Leu Arg Leu Phe His His
            580                 585                 590

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence:ATIC C347G
      polymorphism forward primer

<400> SEQUENCE: 3
```
cctgcaatct ctatcccttt gtaaa                                        25

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence:ATIC C347G
      polymorphism reverse primer

<400> SEQUENCE: 4
ttctgactta ccaatgtcaa tttgct                                       26

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence:ATIC C347G
      polymorphism allelic discrimination 347C wild-type
      fluorescent probe
<220> FEATURE:
<221> NAME/KEY: modified_base
<222> LOCATION: (1)
<223> OTHER INFORMATION: n = fluorescent reporter dye FAM-substituted c
<220> FEATURE:
<221> NAME/KEY: modified_base
<222> LOCATION: (16)
<223> OTHER INFORMATION: n = g conjugated to a DNA minor groove binder
      (MGB) group, e.g., dihydrocyclopyrroloindole
      tripeptide (DPI3)

<400> SEQUENCE: 5
ncaggtgtaa gtgttn                                                  16

<210> SEQ ID NO 6
<211> LENGTH: 16
<212> TYPE: DNA
<213> ORGANISM: Artificial Sequence
<220> FEATURE:
<223> OTHER INFORMATION: Description of Artificial Sequence:ATIC C347G
      polymorphism allelic discrimination 347G mutant
      fluorescent probe
<220> FEATURE:
<221> NAME/KEY: modified_base
<222> LOCATION: (1)
<223> OTHER INFORMATION: n = fluorescent reporter dye VIC-substituted t
<220> FEATURE:
<221> NAME/KEY: modified_base
<222> LOCATION: (16)
<223> OTHER INFORMATION: n = t conjugated to a DNA minor groove binder
      (MGB) group, e.g., dihydrocyclopyrroloindole
      tripeptide (DPI3)

<400> SEQUENCE: 6
nccaggtgta actgtn                                                  16

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:reduced
      folate carrier (RFC-1) G80A polymorphism PCR amplification forward
      primer

<400> SEQUENCE: 7
agtgtcacct tcgtcccctc                                              20

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence:reduced
      folate carrier (RFC-1) G80A polymorphism PCR amplification reverse
      primer

<400> SEQUENCE: 8
ctcccgcgtg aagttctt                                                 18

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:thymidylate
      synthase (TS) 5'-UTR promoter region PCR
      amplification forward primer

<400> SEQUENCE: 9
gtggctcctg cgtttccccc                                               20

<210> SEQ ID NO 10
<211> LENGTH: 38
<212> TYPE: DNA
<213> ORGANISM: Artificial Sequence
<220> FEATURE:
<223> OTHER INFORMATION: Description of Artificial Sequence:thymidylate
      synthase (TS) 5'-UTR promoter region PCR
      amplification reverse primer

<400> SEQUENCE: 10
ccaagcttcg ctccgagccg gccacaggca tggcgcgg                           38

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence:methotrexate
      polyglutamate, MTXPG-2-7
<220> FEATURE:
<221> NAME/KEY: MOD_RES
<222> LOCATION: (1)
<223> OTHER INFORMATION: Xaa = 4-amino-10-methylpteroylglutamic acid
      (methotrexate, MTXPG-1)
<220> FEATURE:
<221> NAME/KEY: MOD_RES
<222> LOCATION: (3)..(7)
<223> OTHER INFORMATION: Glu residues at positions 3-7 may be present or
      absent

<400> SEQUENCE: 11

Xaa Glu Glu Glu Glu Glu Glu
 1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence:methotrexate
      polyglutamate,
      4-amino-10-methylpteroylpenta-glutamic acid,
      MTXPG-5
<220> FEATURE:
<221> NAME/KEY: MOD_RES
<222> LOCATION: (1)
<223> OTHER INFORMATION: Xaa = 4-amino-10-methylpteroylglutamic acid (methotrexate, MTXPG-1)

<400> SEQUENCE: 12

Xaa Glu Glu Glu Glu
 1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence:methotrexate
      polyglutamate, MTXPG-3-5
<220> FEATURE:
<221> NAME/KEY: MOD_RES
<222> LOCATION: (1)
<223> OTHER INFORMATION: Xaa = 4-amino-10-methylpteroylglutamic acid
      (methotrexate, MTXPG-1)
<220> FEATURE:
<221> NAME/KEY: MOD_RES
<222> LOCATION: (4)..(5)
<223> OTHER INFORMATION: Glu at positions 4 and 5 may be present or
      absent

<400> SEQUENCE: 13

Xaa Glu Glu Glu Glu
 1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence:methotrexate
      polyglutamate,
      4-amino-10-methylpteroylhepta-glutamic acid,
      MTXPG-7
<220> FEATURE:
<221> NAME/KEY: MOD_RES
<222> LOCATION: (1)
<223> OTHER INFORMATION: Xaa = 4-amino-10-methylpteroylglutamic acid
      (methotrexate, MTXPG-1)

<400> SEQUENCE: 14

Xaa Glu Glu Glu Glu Glu Glu
 1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence:methotrexate
      polyglutamate,
      4-amino-10-methylpteroylhexa-glutamic acid,
      MTXPG-6

<400> SEQUENCE: 15

Xaa Glu Glu Glu Glu Glu
 1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence:methotrexate
      polyglutamate, MTXPG-1-5
<220> FEATURE:
<221> NAME/KEY: MOD_RES
<222> LOCATION: (1)

-continued

```
<223> OTHER INFORMATION: Xaa = 4-amino-10-methylpteroylglutamic acid
      (methotrexate, MTXPG-1)
<220> FEATURE:
<221> NAME/KEY: MOD_RES
<222> LOCATION: (2)..(5)
<223> OTHER INFORMATION: Glu at positions 2-5 may be present or absent

<400> SEQUENCE: 16

Xaa Glu Glu Glu Glu
 1               5
```

METHODS FOR OPTIMIZING CLINICAL RESPONSIVENESS TO METHOTREXATE THERAPY USING METABOLITE PROFILING AND PHARMACOGENETICS

CROSS-REFERENCES TO RELATED APPLICATIONS

The present application claims priority to U.S. application Ser. No. 10/652,894, filed Aug. 29, 2003, which has been converted to a U.S. Provisional Application, and U.S. Provisional Application No. 60/514,423, filed Oct. 24, 2003, each of which is herein incorporated by reference in its entirety for all purposes.

FIELD OF THE INVENTION

This invention relates generally to medical genetics and, more specifically, to methods for optimizing clinical responsiveness to chemotherapy.

BACKGROUND OF THE INVENTION

Folate (folic acid) is a vitamin that is essential for the life-sustaining processes of DNA synthesis, replication, and repair. Folate is also important for protein biosynthesis, another process that is central to cell viability. The pteridine compound, methotrexate (MTX), is structurally similar to folate and as a result can bind to the active sites of a number of enzymes that normally use folate as a coenzyme for biosynthesis of purine and pyrimidine nucleotide precursors of DNA and for interconversion of amino acids during protein biosynthesis. Despite its structural similarity to folic acid, methotrexate cannot be used as a cofactor by enzymes that require folate, and instead competes with the folate cofactor for enzyme binding sites, thereby inhibiting protein and DNA biosynthesis and, hence, cell division.

The ability of the folate antagonist methotrexate to inhibit cell division has been exploited in the treatment of a number of diseases and conditions that are characterized by rapid or aberrant cell growth. As an example, autoimmune diseases are characterized by an inappropriate immune response directed against normal autologous (self) tissues and mediated by rapidly replicating T-cells or B-cells. Autoimmune diseases that have been treated with methotrexate include, without limitation, rheumatoid arthritis and other forms of arthritis, psoriasis, multiple sclerosis, the autoimmune stage of diabetes mellitus (juvenile-onset or Type 1 diabetes), autoimmune uveoretinitis, myasthenia gravis, autoimmune thyroiditis, and systemic lupus erythematosus.

In particular, methotrexate is currently one of the most widely prescribed drugs for treatment of rheumatoid arthritis (Weinblatt et al., *Eng. J. Med.* 312:818-822 (1985); Kremer and Lee, *Arthritis Rheum.* 29:822-831 (1986)). Although methotrexate is among the best tolerated of the disease-modifying anti-rheumatic drugs (DMARDs), a major drawback of methotrexate therapy is a troublesome inter-patient variability in the clinical response and an unpredictable appearance of side effects including gastrointestinal disturbances, alopecia, elevation of liver enzymes, and bone marrow suppression (Weinblatt et al., *Arthritis Rheum.* 37:1492-1498 (1994); Walker et al, *Arthritis Rheum.* 36:329-335 (1993)). Several studies in well-controlled clinical trials have demonstrated that methotrexate is effective at decreasing functional disability, with the maximum effect occurring after about six months of therapy. However, recent findings from retrospective studies on a large cohort of patients with rheumatoid arthritis have suggested that methotrexate dosage may be suboptimal in some patients (Ortendahl et al., *J. Rheumatol.* 29:2084-2091 (2002)). Thus, the lack of efficient therapeutic drug monitoring of methotrexate therapy and difficulty of rapidly individualizing methotrexate dose-maximizing response hampers effective patient treatment.

Methotrexate enters cells through the reduced folate carrier (RFC-1) and is intracellularly activated by folylpolyglutamate synthase to methotrexate polyglutamates (MTX-PGs) (Chabner et al., *J. Clin. Invest.* 76:907-912 (1985)). The γ-linked sequential addition of glutamic acid residues enhances intracellular retention of methotrexate (Allegra et al., *Proc. Natl. Acad. Sci. USA* 82:4881-4885 (1985)). Polyglutamation also promotes sustained inhibition of de novo purine synthesis (5-aminoimidazole carboxamide-ribonucleotide transformylase (ATIC); Dervieux et al., *Blood* 100:1240-1247 (2002); Allegra et al., supra, 1985), thereby promoting the build-up of adenosine, a potent anti-inflammatory agent (Baggott et al., *Biochem. J.* 236:193-200 (1986); Morabito et al., *J. Clin. Invest.* 101:295-300 (1998); Montesinos et al., *Arthritis* 48:240-247 (2003); Cronstein et al., *J. Clin. Invest.* 92:2675-2682 (1993)). Furthermore, MTXPGs are inhibitors of thymidylate synthase (TS) (Allegra et al., *J. Biol. Chem.* 260:9720-9726 (1985)). TS methylates deoxyuridine monophosphate to produce deoxythymidylate, providing a unique de novo source of thymidylate.

Part of the large inter-individual variability in the response to methotrexate is related to common polymorphisms in genes implicated in methotrexate pharmacokinetics or pharmacodynamics (Relling and Dervieux, *Nat. Rev. Cancer* 1:99-108 (2001)). Recently, a G to A transition in exon 1 (position 80) of RFC-1, resulting in an arginine to histidine substitution at codon 27, was identified (Chango et al., *Mol. Genet. Metab.* 70:310-315 (2000)). However, the functional consequence of this polymorphism on methotrexate transport has remained unclear (Whetstine et al., *Clin. Cancer Res.* 7:3416-3422 (2001); Layerdiere et al., *Blood* 100:3832-3834 (2002)). Moreover, a recent study of children with acute lymphoblastic leukemia has suggested that the A variant may be associated with poor clinical outcomes as compared with patients having the G/G genotype; individuals carrying the A/A genotype presented higher plasma concentrations of methotrexate compared to those with the G/G or G/A genotypes (Layerdiere et al., supra, 2002).

Because individual differences in pharmacokinetic and pharmacodynamic parameters can be difficult to predict and because patient genotype affects these pharmacokinetic and pharmacodynamic parameters, methotrexate treatment can be rendered safer and more effective through patient genotyping. Thus, there exists a need for novel correlations between patient genotypes and efficacy of chemotherapy and for new methods of optimizing clinical responsiveness to methotrexate and other chemotherapies through genotyping. The present invention satisfies these needs and provides related advantages as well.

BRIEF SUMMARY OF THE INVENTION

The present invention provides methods for optimizing clinical responsiveness to chemotherapy in an individual through genotypic analysis of polymorphisms in at least one gene. The methods of the present invention may further comprise determining the level of at least one long-chain methotrexate polyglutamate (MTXPG) in a sample obtained from the individual. The present invention also provides methods for generating a pharmacogenetic index for predicting clinical responsiveness to chemotherapy in an individual through genotypic analysis of polymorphisms in at least one gene. In addition, the present invention provides methods for optimizing therapeutic efficacy of chemotherapy in an individual by calculating the level of at least one long-chain MTXPG in a sample obtained from the individual.

In one aspect, the present invention provides a method for optimizing clinical responsiveness to chemotherapy in an individual comprising:

genotyping the individual at a polymorphic site in at least one gene, wherein the presence of a variant allele at the polymorphic site is indicative of a characteristic clinical responsiveness to the chemotherapy.

In another aspect, the present invention provides a method for optimizing clinical responsiveness to chemotherapy in an individual comprising:

genotyping the individual at a polymorphic site in at least one gene selected from the group consisting of a folate pathway gene, a purine synthesis gene, and a cytokine synthesis gene, wherein the presence of a variant allele at the polymorphic site is indicative of a characteristic clinical responsiveness to the chemotherapy.

In one embodiment, the method further comprises genotyping the individual at a polymorphic site in at least one pyrimidine synthesis gene. In another embodiment, the method further comprises resolving at least one long-chain methotrexate polyglutamate (MTXPG) in a sample obtained from the individual and determining a level of the at least one long-chain MTXPG, wherein the level of the at least one long-chain MTXPG is indicative of a characteristic clinical responsiveness to the chemotherapy.

In certain instances, the method for optimizing clinical responsiveness to chemotherapy comprises:
a) genotyping the individual at a polymorphic site in a reduced folate carrier (RFC-1) gene;
b) genotyping the individual at a polymorphic site in an aminoimidazole carboxamide ribonucleotide transformylase (ATIC) gene; and
c) genotyping the individual at a polymorphic site in a thymidylate synthase (TS) gene, wherein the presence of a variant allele at one or more of the polymorphic sites is indicative of a characteristic clinical responsiveness to the chemotherapy.

In yet another aspect, the present invention provides a method for optimizing clinical responsiveness to arthritis therapy in an individual comprising:

genotyping the individual at a polymorphic site in at least one gene selected from the group consisting of an RFC-1 gene, an ATIC gene, and a TS gene, wherein the presence of a variant allele at the polymorphic site is indicative of a characteristic clinical responsiveness to the arthritis therapy.

In still yet another aspect, the present invention provides a method for optimizing clinical responsiveness to chemotherapy in an individual comprising:
a) genotyping the individual at a polymorphic site in at least one gene selected from the group consisting of a folate pathway gene, a purine synthesis gene, a pyrimidine synthesis gene, and a cytokine synthesis gene;
b) identifying the presence or absence of a variant allele at the polymorphic site;
c) determining whether the individual is wild-type, heterozygous, or homozygous for the variant allele at the polymorphic site; and
d) generating a pharmacogenetic index by calculating the sum of the wild-type, heterozygous, and homozygous variant alleles, wherein the pharmacogenetic index is indicative of a characteristic clinical responsiveness to the chemotherapy.

In a further aspect, the present invention provides a method for optimizing clinical responsiveness to chemotherapy in an individual comprising:
a) genotyping the individual at a polymorphic site in at least one gene selected from the group consisting of a folate pathway gene, a purine synthesis gene, a pyrimidine synthesis gene, and a cytokine synthesis gene;
b) identifying the presence or absence of a variant allele at the polymorphic site;
c) if present, determining whether the variant allele is homozygous at the polymorphic site; and
d) generating a pharmacogenetic index by calculating the sum of the homozygous variant alleles;

wherein the pharmacogenetic index is indicative of a characteristic clinical responsiveness to the chemotherapy.

In another aspect, the present invention provides a method for generating a pharmacogenetic index for predicting clinical responsiveness to chemotherapy in an individual comprising:
a) genotyping the individual at a plurality of polymorphic sites in a plurality of genes;
b) identifying the presence or absence of a variant allele at the plurality of polymorphic sites;
c) determining whether the individual is wild-type, heterozygous, or homozygous for the variant alleles at the plurality of polymorphic sites; and
d) calculating the sum of the wild-type, heterozygous, and homozygous variant alleles, to generate the pharmacogenetic index.

As will be apparent to one of skill in the art, the sum can be a weighted sum wherein the presence or absence of, for example, homozygous variant alleles is weighted more.

In certain instances, the method for generating the pharmacogenetic index comprises:
a) genotyping the individual at a polymorphic site in an RFC-1 gene;
b) genotyping the individual at a polymorphic site in an ATIC gene;
c) genotyping the individual at a polymorphic site in a TS gene;
d) identifying the presence or absence of a variant allele at the polymorphic site in the RFC-1, ATIC, and TS genes;
e) determining whether the individual is wild-type, heterozygous, or homozygous for the variant alleles at the polymorphic site in the RFC-1, ATIC, and TS genes; and
f) calculating the sum of heterozygous variant alleles for the ATIC and TS genes and homozygous variant alleles for the RFC-1, ATIC, and TS genes.

In yet another aspect, the present invention provides a method for generating a pharmacogenetic index for predicting clinical responsiveness to chemotherapy in an individual comprising:
a) genotyping the individual at a plurality of polymorphic sites in a plurality of genes;
b) identifying the presence or absence of a variant allele at the plurality of polymorphic sites;
c) if present, determining whether the variant allele is homozygous at the plurality of polymorphic sites; and
d) calculating the sum of the homozygous variant alleles, to generate the pharmacogenetic index.

In certain instances, the method for generating the pharmacogenetic index comprises:
a) genotyping the individual at a polymorphic site in an RFC-1 gene;

b) genotyping the individual at a polymorphic site in an ATIC gene;
c) genotyping the individual at a polymorphic site in a TS gene;
d) identifying the presence or absence of a variant allele at the polymorphic site in the RFC-1, ATIC, and TS genes;
e) if present, determining which of the variant alleles are homozygous at the polymorphic site in the RFC-1, ATIC, and TS genes; and
f) calculating the sum of the homozygous variant alleles.

In still yet another aspect, the present invention provides a method for optimizing therapeutic efficacy of chemotherapy in an individual comprising:

calculating a level of at least one long-chain MTXPG in a sample from the individual, wherein a level of the at least one long-chain MTXPG less than a predetermined threshold level is indicative of a need to increase the amount of the chemotherapy subsequently administered to the individual.

Other objects, features, and advantages of the present invention will be apparent to one of skill in the art from the following detailed description and figures.

BRIEF DESCRIPTION OF THE DRAWINGS

FIG. 20 shows the human ATIC cDNA nucleotide and amino acid sequences. Panel A: Human ATIC nucleotide sequence (SEQ ID NO:1). Panel B: Human ATIC amino acid Sequence (SEQ ID NO:2).

DETAILED DESCRIPTION OF THE INVENTION

I. Definitions

As used herein, the following terms have the meanings ascribed to them unless specified otherwise.

The term "chemotherapy" refers to the treatment of cancer or a disease or disorder caused by a virus, bacterium, other microorganism, or an inappropriate immune response using specific chemical agents, drugs, or radioactive agents that are selectively toxic and destructive to malignant cells and tissues, viruses, bacteria, or other microorganisms. Chemotherapeutic agents or drugs such as an anti-folate (e.g., methotrexate) or any other agent or drug useful in treating cancer, an inflammatory disease, or an autoimmune disease are preferred. Suitable chemotherapeutic agents and drugs include, but are not limited to, actinomycin D, adriamycin, altretamine, azathioprine, bleomycin, busulphan, capecitabine, carboplatin, carmustine, chlorambucil, cisplatin, cladribine, crisantaspase, cyclophosphamide, cytarabine, dacarbazine, daunorubicin, doxorubicin, epirubicin, etoposide, fludarabine, fluorouracil, gemcitabine, hydroxyurea, idarubicin, ifosfamide, irinotecan, liposomal doxorubicin, lomustine, melphalan, mercaptopurine, methotrexate, mitomycin, mitozantrone, oxaliplatin, paclitaxel, pentostatin, procarbazine, raltitrexed, steroids, streptozocin, taxol, taxotere, temozolomide, thioguanine, thiotepa, tomudex, topotecan, treosulfan, uft (uracil-tegufur), vinblastine, vincristine, vindesine, and vinorelbine. Methotrexate is especially preferred.

Figure 2:
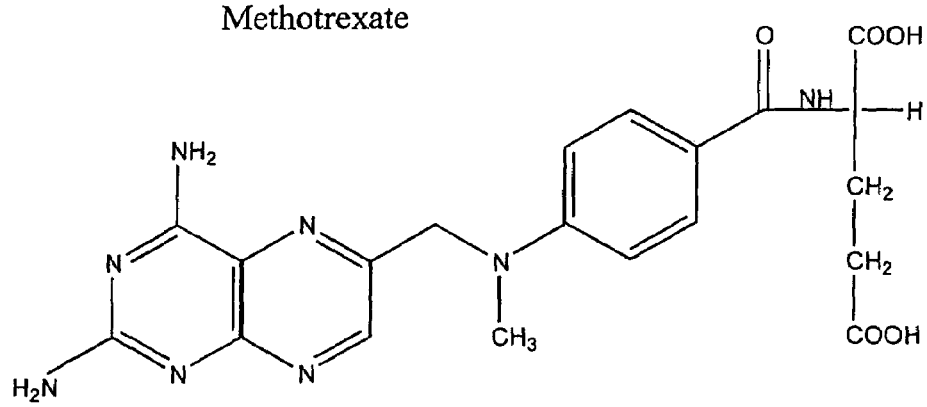
FIG. 2 shows the structures of methotrexate and methotrexate polyglutamates. Upper panel: The chemical structure of methotrexate. Lower panel: The chemical structure for the methotrexate polyglutamates, where N refers to the number of glutamates attached to methotrexate (SEQ ID NO:11).
Figure 2:
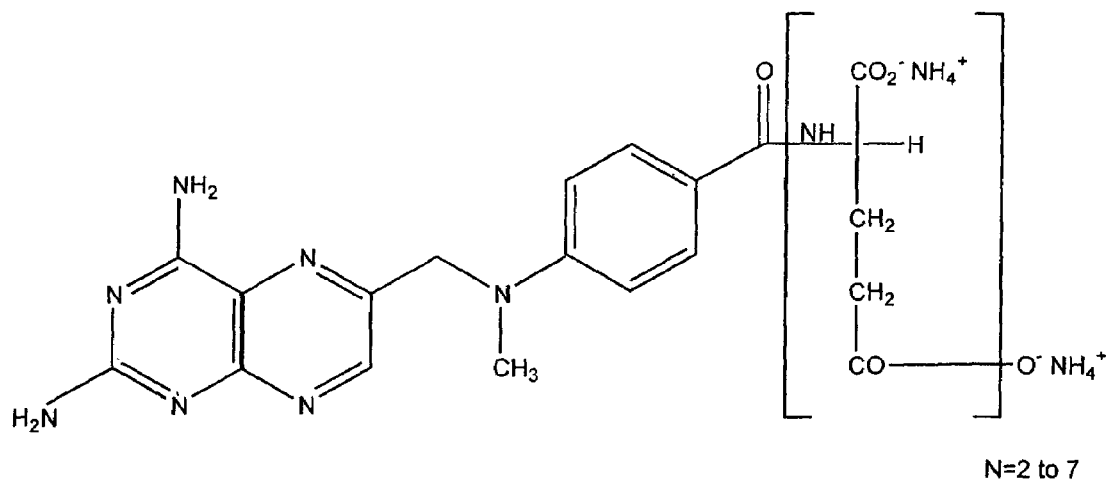

The term "methotrexate" is synonymous with "MTX" and refers to a molecule having the structure shown in FIG. 2, upper panel. Methotrexate includes, in part, a 2,4-diamino substituted pterine ring moiety linked at the 6 position to the amino group of a p-aminobenzoyl moiety, the p-aminobenzoyl moiety having a methylated amino group and being amide bonded to a glutamic acid moiety. As used herein, "$MTXPG_1$" is synonymous with methotrexate.

The term "methotrexate polyglutamate" is synonymous with "MTXPG" and refers to a derivative of methotrexate having two or more glutamates which are amide bonded to the p-aminobenzoyl moiety of methotrexate as shown in the generalized structure of FIG. 2, lower panel. The number of glutamates in a methotrexate polyglutamate varies from two to seven or more; the number of glutamate moieties can be denoted by "n" using the nomenclature $MTXPG_n$ such that, for example, $MTXPG_2$ is MTXPG having two glutamates, $MTXPG_3$ is MTXPG having three glutamates, $MTXPG_4$ is MTXPG having four glutamates, $MTXPG_5$ (SEQ ID NO:12) is MTXPG having five glutamates, $MTXPG_6$ (SEQ ID NO:15) is MTXPG having six glutamates, $MTXPG_7$ (SEQ ID NO:14) is MTXPG having seven glutamates, and $MTXPG_{2-7}$ (SEQ ID NO:11) is a mixture containing $MTXPG_2$, $MTXPG_3$, $MTXPG_4$, $MTXPG_5$ (SEQ ID NO:12), $MTXPG_6$ (SEQ ID NO:15), and $MTXPG_7$ (SEQ ID NO:14), with the ratio of the individual polyglutamated forms in the mixture not defined. As used herein, the term "long-chain MTXPG" refers to any MTX having at least three glutamates attached thereto (e.g., $MTXPG_3$).

The term "autoimmune disease" refers to a disease or disorder resulting from an immune response against a self tissue or tissue component and includes a self antibody response or cell-mediated response. The term autoimmune disease, as used herein, encompasses organ-specific autoimmune diseases, in which an autoimmune response is directed against a single tissue, such as Crohn's disease and ulcerative colitis, Type I diabetes mellitus, myasthenia gravis, vitiligo, Graves' disease, Hashimoto's disease, Addison's disease and autoimmune gastritis; and autoimmune hepatitis. The term autoimmune disease also encompasses non-organ specific autoimmune diseases, in which an autoimmune response is directed against a component present in several or many organs throughout the body. Such autoimmune diseases include, for example, rheumatoid disease, systemic lupus erythematosus, progressive systemic sclerosis and variants, polymyositis and dermatomyositis. Additional autoimmune diseases include, but are not limited to, pernicious anemia, autoimmune gastritis, primary biliary cirrhosis, autoimmune thrombocytopenia, Sjögren's syndrome, multiple sclerosis and psoriasis. One skilled in the art appreciates that the autoimmune diseases set forth above have been treated with chemotherapy such as methotrexate therapy and further recognizes that the methods of the invention can be used to optimize clinical responsiveness to the chemotherapy in a human or other mammal having any of the above or another autoimmune disease.

The term "inflammatory disease" refers to a disease or disorder characterized or caused by inflammation. "Inflammation" refers to a local response to cellular injury that is marked by capillary dilatation, leukocytic infiltration, redness, heat, and pain that serves as a mechanism initiating the elimination of noxious agents and of damaged tissue. The site of inflammation includes the lungs, the pleura, a tendon, a lymph node or gland, the uvula, the vagina, the brain, the spinal cord, nasal and pharyngeal mucous membranes, a muscle, the skin, bone or bony tissue, a joint, the urinary bladder, the retina, the cervix of the uterus, the canthus, the intestinal tract, the vertebrae, the rectum, the anus, a bursa, a follicle, and the like. Such inflammatory diseases include, but are not limited to, fibrositis, inflammatory bowel disease, Crohn's disease, ulcerative colitis, pelvic inflammatory disease, acne, psoriasis, actinomycosis, dysentery, biliary cirrhosis, Lyme disease, heat rash, Stevens-Johnson syndrome, systemic lupus erythematosus, mumps, and blastomycosis.

The term "cancer" refers to any of various malignant neoplasms characterized by the proliferation of anaplastic cells that tend to invade surrounding tissue and metastasize to new body sites. Examples of different types of cancer include, but are not limited to, lung cancer, breast cancer, bladder cancer, thyroid cancer, liver cancer, pleural cancer, pancreatic cancer, ovarian cancer, cervical cancer, testicular cancer, colon cancer, anal cancer, bile duct cancer, gastrointestinal carcinoid tumors, esophageal cancer, gall bladder cancer, rectal cancer, appendix cancer, small intestine cancer, stomach (gastric) cancer, renal cancer, cancer of the central nervous system, skin cancer, choriocarcinomas; head and neck cancers; and osteogenic sarcomas, B-cell lymphoma, non-Hodgkin's lymphoma, Burkitt's lymphoma, fibrosarcoma, neuroblastoma, glioma, melanoma, monocytic leukemia, myelogenous leukemia, acute lymphocytic leukemia, and acute myelocytic leukemia.

The term "gene" refers to the segment of DNA involved in producing a polypeptide chain; it includes regions preceding and following the coding region, such as the promoter and 3'-untranslated region, respectively, as well as intervening sequences (introns) between individual coding segments (exons).

A "folate pathway gene" refers to any gene involved in folate homeostasis and metabolism and includes the proteins encoded by these genes. Examples of folate pathway genes include, without limitation, reduced folate carrier (RFC-1), folylpolyglutamate synthase (FPGS), folylpolyglutamate hydrolase (FPGH), 5,10-methylenetetrahydrofolate reductase (MTHFR), dihydrofolate reductase (DHFR), and efflux transporters such as MRP2.

A "purine synthesis gene" refers to any gene involved in the biosynthesis of purine bases and nucleotides such as adenine monophosphate (AMP), guanine monophosphate (GMP), inosine monophosphate (IMP), and xanthyline monophosphate (XMP), and includes the proteins encoded by these genes. Examples of purine synthesis genes include, without limitation, 5-aminoimidazole carboxamide ribonucleotide transformylase (ATIC), glutamine PRPP amidotransferase, glycinamide ribonucleotide (GAR) synthetase, GAR transformylase, formylglycinamide ribonucleotide (FGAR) amidotransferase, formylglycinamidine ribonucleotide (FGAM) cyclase, 5-aminoimidazole ribonucleotide (AIR) carboxylase, N-succinylo-5-aminoimidazole-4-carboxamide ribonucleotide (SAICAR) synthetase, SAICAR lyase, IMP synthase, adenylosuccinate synthetase, adenylosuccinate lyase, IMP dehydrogenase, and XMP-glutamine amidotransferase.

A "pyrimidine synthesis gene" refers to any gene involved in the biosynthesis of pyrimidine bases and nucleotides such as cytidine monophosphate (CMP), uridine monophosphate (UMP), and thymidine monophosphate (TMP), and includes the proteins encoded by these genes. Examples of pyrimidine synthesis genes include, without limitation, thymidylate synthase (TS), ribonucleotide reductase, nucleoside diphosphate kinase, deaminase, deoxyuridine triphosphatase, aspartate transcarbamoylase, dihydroorotase, dihydroorotate dehydrogenase, orotate phosphoribosyl transferase, orotidylate decarboxylase, and cytidylate synthetase.

A "cytokine synthesis gene" refers to any gene involved in the biosynthesis of proteins such as the interleukins and lymphokines that are released by cells of the immune system and act as intercellular mediators in the generation of an immune response, and includes the proteins encoded by these genes. Examples of cytokine synthesis genes include, without limitation, interleukin-1, interleukin-6, interferon-gamma, tumor necrosis factor alpha, and granulocyte-macrophage colony-stimulating factor.

The term "nucleic acid" or "polynucleotide" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Cassol et al. (1992); Rossolini et al., *Mol. Cell. Probes* 8:91-98 (1994)). The term nucleic acid is used interchangeably with gene, cDNA, and mRNA encoded by a gene.

"Polymorphism" refers to the occurrence of two or more genetically determined alternative sequences or alleles in a population. A "polymorphic site" refers to the locus at which divergence occurs. Preferred polymorphic sites have at least two alleles, each occurring at frequency of greater than 1%, and more preferably greater than 10% or 20% of a selected population. A polymorphic locus may be as small as one base pair (single nucleotide polymorphism, or SNP). Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allele is arbitrarily designated as the reference allele and other alleles are designated as alternative or "variant alleles." The alleles occurring most frequently in a selected population is sometimes referred to as the "wild-type" allele. Diploid organisms may be homozygous or heterozygous for the variant alleles. The variant allele may or may not produce an observable physical or biochemical characteristic ("phenotype") in an individual carrying the variant allele. For example, a variant allele may alter the enzymatic activity of a protein encoded by a gene of interest.

A "single nucleotide polymorphism" or "SNP" occurs at a polymorphic site occupied by a single nucleotide, which is the site of variation between allelic sequences. The site is usually preceded by and followed by highly conserved sequences of the allele (e.g., sequences that vary in less than 1/100 or 1/1000 members of the populations). A SNP usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele.

The term "genotype" as used herein broadly refers to the genetic composition of an organism, including, for example, whether a diploid organism is heterozygous or homozygous for one or more variant alleles of interest.

The term "individual" typically refers to humans, but also to mammals and other animals, multicellular organisms such as plants, and single-celled organisms or viruses.

The term "sample" refers to any biological specimen obtained from an individual. Suitable samples for use in the present invention include, without limitation, whole blood, plasma, serum, red blood cells, saliva, urine, stool (i.e., feces), tears, any other bodily fluid, tissue samples (e.g., biopsy), and cellular extracts thereof (e.g., red blood cellular extract). In a preferred embodiment, the sample is red blood cells or a cellular extract thereof.

A "pharmacogenetic index" or "PGENi" is calculated to predict an increased or decreased probability of clinical responsiveness to chemotherapy in an individual. The present invention provides methods or algorithms for calculating various pharmacogenetic indexes. For example, in one preferred aspect, the pharmacogenetic index is calculated as the sum of the number of variant alleles at one or more polymorphic sites. As such, if an individual is heterozygous for a variant allele at a polymorphic site, the variant allele contributes a value of 1 to the pharmacogenetic index. Likewise, if an individual is homozygous for a variant allele at a polymorphic site, the variant alleles contribute a value of 2 to the pharmacogenetic index. If an individual is wild-type at a polymorphic site, there is no contribution from the variant allele to the pharmacogenetic index.

In another preferred aspect, the pharmacogenetic index is calculated as the sum of the number of homozygous variant alleles at one or more polymorphic sites. For example, an individual that is homozygous for a variant allele (i.e., having 2 copies of the variant allele) contributes a value of 1 to the pharmacogenetic index. In this algorithm, if an individual is wild-type or heterozygous at a polymorphic site, there is no contribution from the variant allele to the pharmacogenetic index.

The present invention is not limited to the foregoing methods or algorithms for generating a PGENi. Using other statistical analyses, a PGENi can be calculated. These methods include, for example, identifying the presence or absence of variant alleles at polymorphic sites in other genes in the folate pathway, purine synthesis pathway, pyrimidine synthesis pathway, cytokine synthesis pathway, or combinations thereof. Further, certain genes or polymorphic sites can have a weighted contribution such that the importance of wild-type, homozygosity, or heterozygosity at that specific site contributes more weight to the PGENi. Other parameters such as phenotypic parameters, e.g., clinical observations, can be used in the algorithms. Other algorithms include, for example, principal component analysis, neural networks, genetic algorithms, fuzzy logic, pattern recognition, and pattern-matching algorithms. Those of skill in the art will know of other algorithms suitable for use in the present invention.

II. General Overview

The present invention provides methods for optimizing clinical responsiveness to chemotherapy in an individual by genotyping at a polymorphic site in at least one gene, and may further comprise determining the concentration level of at least one long-chain methotrexate polyglutamate (MTXPG) in a sample obtained from the individual. In these instances, the presence of one or more variant alleles at one or more of the polymorphic sites, alone or in combination with the level of the long-chain MTXPG(s), is indicative of a characteristic clinical responsiveness to the chemotherapy. The present invention also provides methods for optimizing clinical responsiveness to chemotherapy in an individual by genotyping at a polymorphic site in at least one gene and generating a pharmacogenetic index. In these instances, the value of the pharmacogenetic index is indicative of a characteristic clinical responsiveness to the chemotherapy. In addition, the present invention provides methods for optimizing therapeutic efficacy of chemotherapy in an individual by calculating the level of at least one long-chain MTXPG in a sample obtained from the individual. As such, the present invention provides methods for predicting, determining, and/or calculating the probability that an individual will respond to a particular chemotherapy, and methods for optimizing such responses.

III. Description of the Embodiments

In one aspect, the present invention provides a method for optimizing clinical responsiveness to chemotherapy in an individual comprising:

genotyping the individual at a polymorphic site in at least one gene, wherein the presence of a variant allele at the polymorphic site is indicative of a characteristic clinical responsiveness to the chemotherapy.

In another aspect, the present invention provides a method for optimizing clinical responsiveness to chemotherapy in an individual comprising:

genotyping the individual at a polymorphic site in at least one gene selected from the group consisting of a folate pathway gene, a purine synthesis gene, and a cytokine synthesis gene, wherein the presence of a variant allele at the polymorphic site is indicative of a characteristic clinical responsiveness to the chemotherapy.

In certain instances, the folate pathway gene includes, without limitation, reduced folate carrier (RFC-1), folylpolyglutamate synthase (FPGS), folylpolyglutamate hydrolase (FPGH), 5,10-methylenetetrahydrofolate reductase (MTHFR), dihydrofolate reductase (DHFR), efflux transporters such as MRP2, and combinations thereof. In certain other instances, the purine synthesis gene includes, without limitation, 5-aminoimidazole carboxamide ribonucleotide transformylase (ATIC), glutamine PRPP amidotransferase, glycinamide ribonucleotide (GAR) synthetase, GAR transformylase, formylglycinamide ribonucleotide (FGAR) amidotransferase, formylglycinamidine ribonucleotide (FGAM) cyclase, 5-aminoimidazole ribonucleotide (AIR) carboxylase, N-succinylo-5-aminoimidazole-4-carboxamide ribonucleotide (SAICAR) synthetase, SAICAR lyase, IMP synthase, adenylosuccinate synthetase, adenylosuccinate lyase, IMP dehydrogenase, XMP-glutamine amidotransferase, and combinations thereof. In yet certain other instances, the cytokine synthesis gene includes, without limitation, interleukin-1, interleukin-6, interferon-gamma, tumor necrosis factor alpha (TNFalpha), granulocyte-macrophage colony-stimulating factor, and combinations thereof.

In one embodiment, the method further comprises genotyping the individual at a polymorphic site in at least one pyrimidine synthesis gene. In certain instances, the pyrimidine synthesis gene includes, without limitation, thymidylate synthase (TS), ribonucleotide reductase, nucleoside diphosphate kinase, deaminase, deoxyuridine triphosphatase, aspartate transcarbamoylase, dihydroorotase, dihydroorotate dehydrogenase, orotate phosphoribosyl transferase, orotidylate decarboxylase, cytidylate synthetase, and combinations thereof.

In another embodiment, the chemotherapy is anti-folate therapy. Preferably, the anti-folate therapy is methotrexate (MTX). In yet another embodiment, the individual has a disease selected from the group consisting of cancer, an inflammatory disease, and an autoimmune disease. In certain instances, the individual has rheumatoid arthritis. In certain other instances, the polymorphic site is located in a coding region, or alternatively, in a non-coding region such as a promoter, of the gene or genes described above. Preferably, the polymorphic site is a single nucleotide polymorphism (SNP).

In yet another embodiment, the presence of the variant allele at the polymorphic site is indicative of either superior or inferior clinical responsiveness to the chemotherapy. In certain instances, variant allele homozygosity is indicative of either superior or inferior clinical responsiveness to the chemotherapy. In certain other instances, the greater number of variant alleles at the polymorphic site is indicative of either superior or inferior clinical responsiveness to the chemotherapy. One of skill in the art will appreciate that the number of variant alleles varies depending on the number of genes that are genotyped. For example, an individual genotyped at a polymorphic site in 1 gene may carry as many as 2 variant alleles. As a result, the number of variant alleles can range from between 0 and 2, with 0 being wild-type (i.e., no variant alleles), 1 being heterozygous (i.e., 1 variant allele), and 2 being homozygous (i.e., 2 variant alleles). In still yet another embodiment, the variant allele is associated with either increased or decreased activity or expression of the gene or protein encoded by the gene.

In a preferred embodiment, the folate pathway gene is an RFC-1 gene. In certain instances, the presence of the variant allele at the polymorphic site in the RFC-1 gene is indicative of superior clinical responsiveness to the chemotherapy. In such instances, the variant allele is associated with increased RFC-1 activity or expression. Alternatively, the presence of the variant allele at the polymorphic site in the RFC-1 gene is indicative of inferior clinical responsiveness to the chemotherapy. In such instances, the variant allele is associated with decreased RFC-1 activity or expression.

Preferably, the polymorphic site in the RFC-1 gene is a SNP, wherein the variant allele at the SNP comprises a G to A mutation at nucleotide 80. In one embodiment, the presence of the RFC-1 80A variant allele is indicative of superior clinical responsiveness to the chemotherapy. In certain instances, variant allele homozygosity (i.e., RFC-1 80A/A) is indicative of superior clinical responsiveness to the chemotherapy. In certain other instances, the greater number of RFC-1 80A variant alleles is indicative of superior clinical responsiveness to the chemotherapy. For example, the number of RFC-1 80A variant alleles can range from between 0 and 2, with 0 being wild-type (i.e., RFC-1 80G/G), 1 being heterozygous (i.e., RFC-1 80G/A), and 2 being homozygous (i.e., RFC-1 80A/A). Preferably, the number of the RFC-1 80A variant alleles is 2. In another embodiment, the RFC-1 80A variant allele is associated with increased RFC-1 activity or expression. One of skill in the art will appreciate that other polymorphic sites within the RFC-1 gene are also suitable for genotyping according to the methods of the present invention.

In another preferred embodiment, the purine synthesis gene is an ATIC gene. In certain instances, the presence of the variant allele at the polymorphic site in the ATIC gene is indicative of superior clinical responsiveness to the chemotherapy. In such instances, the variant allele is associated with decreased ATIC activity or expression. Alternatively, the presence of the variant allele at the polymorphic site in the ATIC gene is indicative of inferior clinical responsiveness to the chemotherapy. In such instances, the variant allele is associated with increased ATIC activity or expression.

Preferably, the polymorphic site in the ATIC gene is a SNP, wherein the variant allele at the SNP comprises a C to G mutation at nucleotide 347. In one embodiment, the presence of the ATIC 347G variant allele is indicative of superior clinical responsiveness to the chemotherapy. In certain instances, variant allele homozygosity (i.e., ATIC 347G/G) is indicative of superior clinical responsiveness to the chemotherapy. In certain other instances, the greater number of ATIC 347G variant alleles is indicative of superior clinical responsiveness to the chemotherapy. For example, the number of ATIC 347G variant alleles can range from between 0 and 2, with 0 being wild-type (i.e., ATIC 347C/C), 1 being heterozygous (i.e., ATIC 347C/G), and 2 being homozygous (i.e., ATIC 347G/G). Preferably, the number of the RFC-1 80A variant alleles is 2. In another embodiment, the ATIC 347G variant allele is associated with decreased ATIC activity or expression. One of skill in the art will appreciate that other polymorphic sites within the ATIC gene are also suitable for genotyping according to the methods of the present invention.

In yet another preferred embodiment, the pyrimidine synthesis gene is a TS gene. In certain instances, the presence of the variant allele at the polymorphic site in the TS gene is indicative of superior clinical responsiveness to the chemotherapy. In such instances, the variant allele is associated with decreased TS activity or expression. Alternatively, the presence of the variant allele at the polymorphic site in the TS gene is indicative of inferior clinical responsiveness to the chemotherapy. In such instances, the variant allele is associated with increased TS activity or expression.

Preferably, the polymorphic site in the TS gene is located in the promoter, wherein the variant allele comprises a two 28 base pair tandem repeat (2TR) in the promoter. In one embodiment, the presence of the TS 2TR variant allele is indicative of superior clinical responsiveness to the chemotherapy. In certain instances, variant allele homozygosity (i.e., TS 2TR/2TR) is indicative of superior clinical responsiveness to the chemotherapy. In certain other instances, the greater number of TS 2TR variant alleles is indicative of superior clinical responsiveness to the chemotherapy. For example, the number of TS 2TR variant alleles can range from between 0 and 2, with 0 being wild-type (i.e., TS 3TR/3TR), 1 being heterozygous (i.e., TS 3TR/2TR), and 2 being homozygous (i.e., TS 2TR/2TR). Preferably, the number of the TS 2TR variant alleles is 2. In another embodiment, the TS 2TR variant allele is associated with decreased TS activity or expression. One of skill in the art will appreciate that other polymorphic sites within the TS gene are also suitable for genotyping according to the methods of the present invention.

In another embodiment, the presence of the variant allele at the polymorphic site in the cytokine synthesis gene (e.g., TNFalpha) is indicative of superior clinical responsiveness to the chemotherapy. Alternatively, the presence of the variant allele at the polymorphic site in the cytokine synthesis gene is indicative of inferior clinical responsiveness to the chemotherapy. In certain instances, the variant allele is associated with increased cytokine synthesis gene activity or expression. In certain other instances, the variant allele is associated with decreased cytokine synthesis gene activity or expression. One of skill in the art will appreciate that any polymorphic site within the cytokine synthesis gene is suitable for genotyping according to the methods of the present invention, e.g., a G to A mutation at nucleotide −308 in the promoter of TNFalpha (see, Mugnier et al., *Arthritis Rheum.* 48:1849-1852 (2003)).

In still yet another preferred embodiment, the method of the present invention comprises:

genotyping the individual at a polymorphic site in at least one gene selected from the group consisting of an RFC-1 gene, an ATIC gene, and a TS gene, wherein the presence of a variant allele at the polymorphic site is indicative of a characteristic clinical responsiveness to the chemotherapy.

In a particularly preferred embodiment, the method of the present invention comprises:

a) genotyping the individual at a polymorphic site in an RFC-1 gene;

b) genotyping the individual at a polymorphic site in an ATIC gene; and c) genotyping the individual at a polymorphic site in a TS gene, wherein the presence of a variant allele at one or more of the polymorphic sites is indicative of a characteristic clinical responsiveness to the chemotherapy.

In one embodiment, the presence of a variant allele at one or more of the polymorphic sites is indicative of either superior or inferior clinical responsiveness to the chemotherapy. In certain instances, variant allele homozygosity for at least one of the variant alleles is indicative of either superior or inferior clinical responsiveness to the chemotherapy. In certain other instances, the greater number of the variant alleles is indicative of either superior or inferior clinical responsiveness to the chemotherapy. One of skill in the art will appreciate that the number of variant alleles varies depending on the number of genes that are genotyped. For example, an individual genotyped at polymorphic sites in 3 genes (i.e., RFC-1, ATIC, and TS) may carry as many as 6 variant alleles (i.e., if the individual is homozygous for each of the variant alleles.) For each gene that is genotyped, 0 refers to wild-type (i.e., no variant alleles), 1 refers to heterozygous (i.e., 1 variant allele), and 2 refers to homozygous (i.e., 2 variant alleles). The number of variant alleles for all three genes is thus the sum of the number of variant alleles of each gene.

Figure 3:
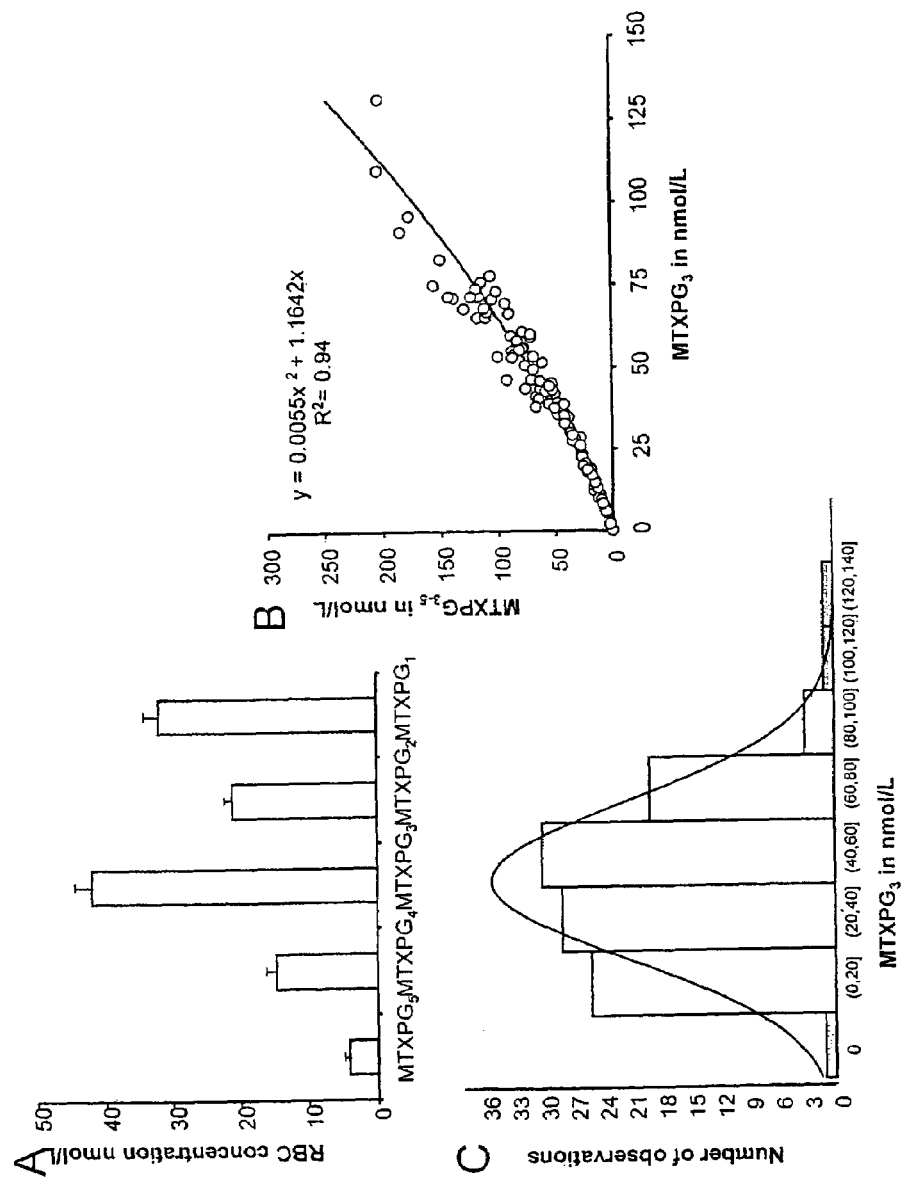
FIG. 3 shows red blood cell methotrexate polyglutamate (MTXPG) concentrations in a population of rheumatoid arthritis patients. Panel A: Average (standard error) of individual red blood cell (RBC) MTXPG concentrations in the population of 108 rheumatoid arthritis patients. $MTXPG_5$= (SEQ ID NO:12. Panel B: Correlation between red blood cell $MTXPG_3$ and red blood cell $MTXPG_{3-5}$ (SEQ ID NO:13) levels. Panel C: Histogram distribution of $MTXPG_3$ in the rheumatoid arthritis study population. The $MTXPG_3$ range in nmol/L is shown in parentheses on the X-axis.

In another embodiment, the method further comprises resolving at least one long-chain methotrexate polyglutamate (MTXPG) in a sample obtained from the individual and determining a level of the at least one long-chain MTXPG, wherein the level of the at least one long-chain MTXPG is indicative of a characteristic clinical responsiveness to the chemotherapy. Preferably, the at least one long-chain MTXPG is selected from the group consisting of $MTXPG_3$, $MTXPG_4$, $MTXPG_5$ (SEQ ID NO:12), and combinations thereof. In certain instances, the at least one long-chain MTXPG is $MTXPG_{3-5}$ (SEQ ID NO:13). In certain other instances, the at least one long-chain MTXPG is $MTXPG_3$. In certain instances, a level of $MTXPG_3$ greater than about 60 nmol/L is indicative of superior clinical responsiveness to the chemotherapy. In certain other instances, a level of $MTXPG_3$ less than about 40 nmol/L is indicative of inferior clinical responsiveness to the chemotherapy. However, one skilled in the art will appreciate that additional threshold levels of $MTXPG_3$, e.g., about 10 nmol/L, 15 nmol/L, 20 nmol/L, 25 nmol/L, 30 nmol/L, 35 nmol/L, 40 nmol/L, 45 nmol/L, 50 nmol/L, 55 nmol/L, 60 nmol/L, 65 nmol/L, 70 nmol/L, 75 nmol/L, or 80 nmol/L, are also within the scope of the present invention. In a preferred embodiment, the level of $MTXPG_3$ is predictive of the level of $MTXPG_{3-5}$ (SEQ ID NO:13) (see, FIG. 3B). As such, one skilled in the art will appreciate that a given threshold level of $MTXPG_3$ can be used to determine a corresponding threshold level of $MTXPG_{3-5}$ (SEQ ID NO:13) for use in the methods of the present invention.

In yet another embodiment, the sample obtained from the individual includes, without limitation, whole blood, plasma, serum, red blood cells, saliva, urine, stool (i.e., feces), tears, any other bodily fluid, tissue samples (e.g., biopsy), and cellular extracts thereof (e.g., red blood cellular extract). Preferably, the sample is red blood cells. In still yet another embodiment, chromatography is used to resolve the at least one long-chain MTXPG in the sample. Chromatography techniques suitable for use in the methods of the present invention include, without limitation, any liquid or gas phase chromatographic technique such as, for example, ion exchange chromatography, size exclusion chromatography, iso-electric focusing, gel electrophoresis, capillary electrophoresis, normal phase chromatography (e.g., high performance liquid chromatography (HPLC)), reverse phase chromatography (e.g., RP-HPLC), and affinity chromatography. Preferably, HPLC is used to resolve the at least one long-chain MTXPG in the sample. In a further embodiment, the level of the at least one long-chain MTXPG is determined using any detection method known in the art including, but not limited to, fluorimetry, spectrophotometry, and spectrometry. Exemplary, but not limiting, spectrometric methods include mass spectrometry, tandem mass spectrometry, and preparative mass spectrometry with electrospray ionization.

In yet another aspect, the present invention provides a method for optimizing clinical responsiveness to arthritis therapy in an individual comprising:

genotyping the individual at a polymorphic site in at least one gene selected from the group consisting of an RFC-1 gene, an ATIC gene, and a TS gene, wherein the presence of a variant allele at the polymorphic site is indicative of a characteristic clinical responsiveness to the arthritis therapy.

In one embodiment, the arthritis therapy is anti-folate therapy. Preferably, the anti-folate is methotrexate (MTX). In another embodiment, the individual has rheumatoid arthritis. In certain instances, the polymorphic site is located in a coding region, or alternatively, in a non-coding region such as a promoter, of the RFC-1 gene, ATIC gene, TS gene, or combinations thereof. Preferably, the polymorphic site is a SNP in the RFC-1 gene or ATIC gene as described above. A polymorphic site located in the promoter of the TS gene as described above is also preferred. In yet another embodiment, the presence of the variant allele at the polymorphic site is indicative of either superior or inferior clinical responsiveness to the arthritis therapy as described above. In a preferred embodiment, the method comprises genotyping the individual at a polymorphic site in all three genes as described above.

In still yet another aspect, the present invention provides a method for optimizing clinical responsiveness to chemotherapy in an individual comprising:

a) genotyping the individual at a polymorphic site in at least one gene selected from the group consisting of a folate pathway gene, a purine synthesis gene, a pyrimidine synthesis gene, and a cytokine synthesis gene;

b) identifying the presence or absence of a variant allele at the polymorphic site;

c) determining whether the individual is wild-type, heterozygous, or homozygous for the variant allele at the polymorphic site; and d) generating a pharmacogenetic index by calculating the sum of the wild-type, heterozygous, and homozygous variant alleles, wherein the pharmacogenetic index is indicative of a characteristic clinical responsiveness to the chemotherapy.

Examples of folate pathway genes, purine synthesis genes, pyrimidine synthesis genes, and cytokine synthesis genes suitable for use in the methods of the present invention are described above. In certain instances, the pharmacogenetic index is indicative of superior clinical responsiveness to the chemotherapy. In certain other instances, the pharmacogenetic index is indicative of inferior clinical responsiveness to the chemotherapy. In a preferred embodiment, the at least one gene is selected from the group consisting of an RFC-1 gene, an ATIC gene, a TS gene, and combinations thereof, wherein the pharmacogenetic index is generated by calculating the sum of heterozygous or homozygous variant alleles for the ATIC and TS genes and homozygous variant alleles for the RFC-1 gene. As a non-limiting example, when all three genes are genotyped, the pharmacogenetic index is the sum of the number of ATIC 347G variant alleles (0: ATIC 347C/C, 1: ATIC 347C/G; 2: ATIC 347G/G), plus the number of TS 2TR variant alleles (0: TSER 3TR/3TR; 1: TSER 3TR/2TR; 2: TSER 2TR/2TR), plus the presence of the RFC-1 80A/A homozygous variant allele genotype (0: RFC-1 80G/G or RFC-1 80G/A; 1: RFC-1 80A/A). However, one skilled in the art will appreciate that other values can be assigned to a particular variant allele or variant allele genotype for calculating the pharmacogenetic index.

In a further aspect, the present invention provides a method for optimizing clinical responsiveness to chemotherapy in an individual comprising:

a) genotyping the individual at a polymorphic site in at least one gene selected from the group consisting of a folate pathway gene, a purine synthesis gene, a pyrimidine synthesis gene, and a cytokine synthesis gene;

b) identifying the presence or absence of a variant allele at the polymorphic site;

c) if present, determining whether the variant allele is homozygous at the polymorphic site; and d) generating a pharmacogenetic index by calculating the sum of the homozygous variant alleles;

wherein the pharmacogenetic index is indicative of a characteristic clinical responsiveness to the chemotherapy.

Examples of folate pathway genes, purine synthesis genes, pyrimidine synthesis genes, and cytokine synthesis genes suitable for use in the methods of the present invention are described above. In certain instances, the pharmacogenetic index is indicative of superior clinical responsiveness to the chemotherapy. In certain other instances, the pharmacogenetic index is indicative of inferior clinical responsiveness to the chemotherapy. In a preferred embodiment, the at least one gene is selected from the group consisting of an RFC-1 gene, an ATIC gene, a TS gene, and combinations thereof, wherein the pharmacogenetic index is generated by calculating the sum of heterozygous or homozygous variant alleles for the ATIC and TS genes and homozygous variant alleles for the RFC-1 gene. As a non-limiting example, when all three genes are genotyped, the pharmacogenetic index is the sum of the presence of the ATIC 347G/G homozygous variant allele genotype (0: ATIC 347C/C or ATIC 347C/G; 1: ATIC 347G/G), plus the presence of the TS 2TR/2TR homozygous variant allele genotype (0: TR 3TR/3TR or TR 3TR/2TR; 1: TR 2TR/2TR), plus the presence of the RFC-1 80A/A homozygous variant allele genotype (0: RFC-1 80G/A or RFC-1 80G/G; 1: RFC-1 80A/A). However, one skilled in the art will appreciate that other values can be assigned to a particular variant allele genotype for calculating the pharmacogenetic index.

In another aspect, the present invention provides a method for generating a pharmacogenetic index for predicting clinical responsiveness to chemotherapy in an individual comprising:

a) genotyping the individual at a plurality of polymorphic sites in a plurality of genes;

b) identifying the presence or absence of a variant allele at the plurality of polymorphic sites;

c) determining whether the individual is wild-type, heterozygous, or homozygous for the variant alleles at the plurality of polymorphic sites; and d) calculating the sum of the wild-type, heterozygous, and homozygous variant alleles, to generate the pharmacogenetic index.

In one embodiment, the pharmacogenetic index is indicative of a characteristic clinical responsiveness to the chemotherapy. In another embodiment, the pharmacogenetic index is indicative of either a superior or inferior clinical responsiveness to the chemotherapy. As will be apparent to one of skill in the art, the sum can be a weighted sum wherein the presence or absence of, for example, homozygous variant alleles is weighted more.

In certain instances, the method for generating the pharmacogenetic index comprises:

a) genotyping the individual at a polymorphic site in at least one gene selected from the group consisting of an RFC-1 gene, an ATIC gene, and a TS gene;

b) identifying the presence or absence of a variant allele at the polymorphic site in at least one of the RFC-1, ATIC, and TS genes;

c) determining whether the individual is wild-type, heterozygous, or homozygous for the variant allele at the polymorphic site in at least one of the RFC-1, ATIC, and TS genes; and d) calculating the sum of heterozygous variant alleles for the ATIC and TS genes and homozygous variant alleles for the RFC-1, ATIC, and TS genes.

In certain other instances, the method for generating the pharmacogenetic index comprises:

a) genotyping the individual at a polymorphic site in an RFC-1 gene;

b) genotyping the individual at a polymorphic site in an ATIC gene;

c) genotyping the individual at a polymorphic site in a TS gene;

d) identifying the presence or absence of a variant allele at the polymorphic site in the RFC-1, ATIC, and TS genes;

e) determining whether the individual is wild-type, heterozygous, or homozygous for the variant allele at the polymorphic site in the RFC-1, ATIC, and TS genes; and f) calculating the sum of heterozygous variant alleles for the ATIC and TS genes and homozygous variant alleles for the RFC-1, ATIC, and TS genes.

In yet another aspect, the present invention provides a method for generating a pharmacogenetic index for predicting clinical responsiveness to chemotherapy in an individual comprising:

a) genotyping the individual at a plurality of polymorphic sites in a plurality of genes;

b) identifying the presence or absence of a variant allele at the plurality of polymorphic sites;

c) if present, determining whether the variant allele is homozygous at the plurality of polymorphic sites; and d) calculating the sum of the homozygous variant alleles, to generate the pharmacogenetic index.

In one embodiment, the pharmacogenetic index is indicative of a characteristic clinical responsiveness to the chemotherapy. In another embodiment, the pharmacogenetic index is indicative of either a superior or inferior clinical responsiveness to the chemotherapy.

In certain instances, the method for generating the pharmacogenetic index comprises:

a) genotyping the individual at a polymorphic site in at least one gene selected from the group consisting of an RFC-1 gene, an ATIC gene, and a TS gene;

b) identifying the presence or absence of a variant allele at the polymorphic site in at least one of the RFC-1, ATIC, and TS genes;

c) if present, determining which of the variant alleles are homozygous at the polymorphic site in at least one of the RFC-1, ATIC, and TS genes; and d) calculating the sum of the homozygous variant alleles.

In certain other instances, the method for generating the pharmacogenetic index comprises:

a) genotyping the individual at a polymorphic site in an RFC-1 gene;

b) genotyping the individual at a polymorphic site in an ATIC gene;

c) genotyping the individual at a polymorphic site in a TS gene;

d) identifying the presence or absence of a variant allele at the polymorphic site in the RFC-1, ATIC, and TS genes;

e) if present, determining which of the variant alleles are homozygous at the polymorphic site in the RFC-1, ATIC, and TS genes; and f) calculating the sum of the homozygous variant alleles.

In still yet another aspect, the present invention provides a method for optimizing therapeutic efficacy of chemotherapy in an individual comprising:

calculating a level of at least one long-chain MTXPG in a sample from the individual, wherein a level of the at least one long-chain MTXPG less than a predetermined threshold level is indicative of a need to increase the amount of the chemotherapy subsequently administered to the individual.

In one embodiment, the chemotherapy is anti-folate therapy. Preferably, the anti-folate is MTX. In another embodiment, the individual has a disease selected from the group consisting of cancer, an inflammatory disease, and an autoimmune disease. In certain instances, the individual has rheumatoid arthritis. In yet another embodiment, the sample is any sample from the individual as described above. Preferably, the sample is red blood cells.

In certain instances, the predetermined threshold level is about 40 nmol/L. In certain other instances, the predetermined threshold level is about 60 nmol/L. However, one skilled in the art will appreciate that additional threshold levels, e.g., about 10 nmol/L, 15 mmol/L, 20 nmol/L, 25 nmol/L, 30 nmol/L, 35 nmol/L, 45 nmol/L, 50 nmol/L, 55 nmol/L, 65 nmol/L, 70 nmol/L, 75 mol/L, or 80 nmol/L, are also within the scope of the present invention. Preferably, the at least one long-chain MTXPG is selected from the group consisting of $MTXPG_3$, $MTXPG_4$, $MTXPG_5$ (SEQ ID NO:12), and combinations thereof. In certain instances, the at least one long-chain MTXPG is $MTXPG_{3-5}$ (SEQ ID NO:13). In certain other instances, the at least one long-chain MTXPG is $MTXPG_3$.

In still yet another embodiment, a chromatographic technique as described above is used to resolve the at least one long-chain MTXPG in the sample. Preferably, the chromatographic technique is HPLC. In a further embodiment, the level of the at least one long-chain MTXPG is determined (i.e., calculated) using any detection method known in the art including, but not limited to, fluorimetry, spectrophotometry, and spectrometry (e.g., mass spectrometry).

A. Methotrexate Therapy

Methotrexate is well known in the art as an inhibitor of dihydrofolate reductase (DHFR), which acts to decrease production of tetrahydrofolate (THF) from dihydrofolate (DHF). As a consequence, methotrexate indirectly inhibits purine and thymidine synthesis and amino acid interconversion. Methotrexate also exhibits anti-proliferative activity through inhibition of thymidylate synthesis, which is required to synthesize DNA (Calvert, *Semin. Oncol.* 26:3-10 (1999)). Methotrexate, its synthesis, and its properties are described in further detail in U.S. Pat. Nos. 2,512,572; 3,892,801; 3,989,703; 4,057,548; 4,067,867; 4,079,056; 4,080,325; 4,136,101; 4,224,446; 4,306,064; 4,374,987; 4,421,913; and 4,767,859. Methods of using methotrexate to treat cancer are described, for example, in U.S. Pat. Nos. 4,106,488, 4,558,690, and 4,662,359.

Methotrexate, which is useful in the treatment of a variety of autoimmune diseases and cancers, can be administered by oral or parenteral routes. The drug is readily distributed to body tissues, where it is transported into cells by a specific carrier system that includes components such as the reduced folate carrier, RFC-1, and the folate receptor. Due to its high polarity at physiological pH, methotrexate does not readily pass through the cell membrane, and the majority of the drug enters cells via specific carriers. Once inside the cell, methotrexate is converted to methotrexate polyglutamates by specific enzymes such as folylpolygamma-glutamate synthetase, which add one or more glutamic acid moieties, linked by iso-peptidic bonds to the γ-carboxyl of methotrexate as described, for example, in Kamen, *Semin. Oncol.* S18:30-39 (1997).

The methods of the invention also can be used to optimize clinical responsiveness to a methotrexate analog or other polyglutamylatable anti-folate. As used herein, the term "anti-folate" means a molecule having structural similarity to folate and activity as a folate antagonist against one or more folate-dependent enzymes. Polyglutamylatable anti-folates are anti-folates that can be polyglutamated in a cell by an enzyme such as folylpoly-gamma-glutamate synthetase. Examples of polyglutamylatable anti-folates include, without limitation, aminopterin, raltitrexed, lometrexol, multitargeted anti-folate (MTA), AQA, MTX, and analogs thereof. Aminopterin, for example, possesses a hydrogen instead of a methyl group at position N-10 compared to the structure of methotrexate. Raltitrexed is a selective inhibitor of thymidylate synthase as described, for example, in Kamen, *Semin. Oncol.* S18:30-39 (1997). Lometrexol selectively inhibits glycinamide ribonucleotide formyltransferase, the first enzyme involved in the pathway of de novo purine synthesis as described, for example, in Calvert, supra, 1999. Multitargeted anti-folate is an inhibitor of multiple folate-dependent enzymes, such as dihydrofolate reductase, thymidylate synthase, and glycinamide ribonucleotide formyltransferase (see, for example, Calvert, supra, 1999). In certain instances, methotrexate (an anti-folate) is used in a combination therapy with polyglutamates. Other anti-folates suitable for use in the presence invention include, for example, aminopterin, edetrexate, lomotrexol, BW1843U89, and ZD1694.

In one embodiment, a method of the invention is used to optimize clinical responsiveness to a methotrexate analog. As used herein, the term "methotrexate analog" means a molecule having structural and functional similarity to methotrexate. Methotrexate analogs are functionally characterized, in part, by their inhibitory activity against dihydrofolate reductase. A methotrexate analog useful in the invention acts as a substrate for polyglutamation in a cell by an enzyme such as folylpoly-gamma-glutamate synthetase. Methotrexate analogs include, but are not limited to, 4-amino derivatives with halogen substitution on the para-aminobenzoic moiety, such as dichloromethotrexate (see, for example, Frei et al., *Clin. Pharmacol. Therap.* 6:160-71 (1965)); 7-methyl substituted MTX (see, for example, Rosowsky and Chen, *J. Med. Chem.* 17:1308-11 (1974)); 3',5'-difluoro MTX, (see, for example, Tomcuf, *J. Organic Chem.* 26:3351 (1961)); 2' and 3' monofluorinated derivatives of aminopterin (see, for example, Henkin and Washtien, *J. Med. Chem.* 26:1193-1196 (1983)); and 7,8-dihydro-8-methyl-MTX (see, for example, Chaykovsky, *J. Org. Chem.* 40:145-146 (1975)). The skilled person understands that the methods of the invention can be used to optimize or monitor clinical responsiveness or toxicity associated with methotrexate analog therapy or other polyglutamylatable anti-folate therapy in the same manner as disclosed herein for optimizing clinical responsiveness to methotrexate therapy.

Rheumatoid arthritis and a variety of other autoimmune disorders such as psoriasis, systemic lupus erythematosus, and graft-versus-host disease are typically treated with low-dose methotrexate therapy, which is also used in some cancer treatment regimens. In one embodiment, a method of the invention is used to optimize clinical responsiveness in a human undergoing low-dose methotrexate therapy. As used herein, the term "low-dose MTX therapy" means administration of methotrexate to a human at a dose that is less than mg/m$^2$ of body surface per week. Typically, low-dose methotrexate therapy is administered orally at a dose in the range of 2.5 to 40 mg/m$^2$ of body surface per week, for example, 2.5 to 25 mg/m$^2$ of body surface per week depending upon the condition being treated.

The methods of the invention also can be useful for optimizing clinical responsiveness to chemotherapy in a human undergoing high-dose methotrexate therapy. As used herein, the term "high-dose MTX therapy" means administration of methotrexate to an individual at a dose that is at least 40 mg/m$^2$ of body surface per day, for example, at least 100, 500, 1000, 1500, 3000 mg/m$^2$ or 5000 mg/m$^2$ of body surface per day.

One skilled in the art understands that high-dose methotrexate therapy is frequently used as an anti-cancer therapeutic and can be administered at doses up to 5 g/m$^2$ of body surface per day or higher depending upon the condition or disease being treated. One skilled in the art recognizes that the doses of methotrexate typically used in high-dose MTX therapy can be administered, for example, intravenously or orally and that such high-dose methotrexate therapy generally requires a period of recovery, which can include leucovorin rescue or another form of folate replacement. It will be understood that the dosage ranges of methotrexate set forth above in the definitions of high and low-dose methotrexate therapy are generalized with respect to treatment of a variety of diseases and that the range of methotrexate dose that is administered for one disease can differ from the range administered for another. Accordingly, a dose of 40 mg/m$^2$ of body surface per day, although generally considered high-dose methotrexate therapy, may be considered by those skilled in the art of cancer therapy as a relatively low dose for treating cancer. Similarly, a dose of 30 mg/m$^2$ of body surface per day, although generally considered as low-dose methotrexate therapy, may be considered by those skilled in the art of rheumatology as a relatively high-dose for treating rheumatoid arthritis.

B. Pharmacogenetcis of Methotrexate Therapy

As disclosed herein, methotrexate therapy was monitored in patients with rheumatoid arthritis, and novel associations between genetic polymorphisms in the de novo purine synthesis pathway and clinical responsiveness to chemotherapy have been identified. In particular, the results disclosed herein in Example 1 indicate that quantification of long-chain (e.g., MTXPG$_{3-5}$; (SEQ ID NO:13)) methotrexate polyglutamate concentrations correlates with MTXPG$_3$ concentrations (see, FIG. 3).

Figure 1:
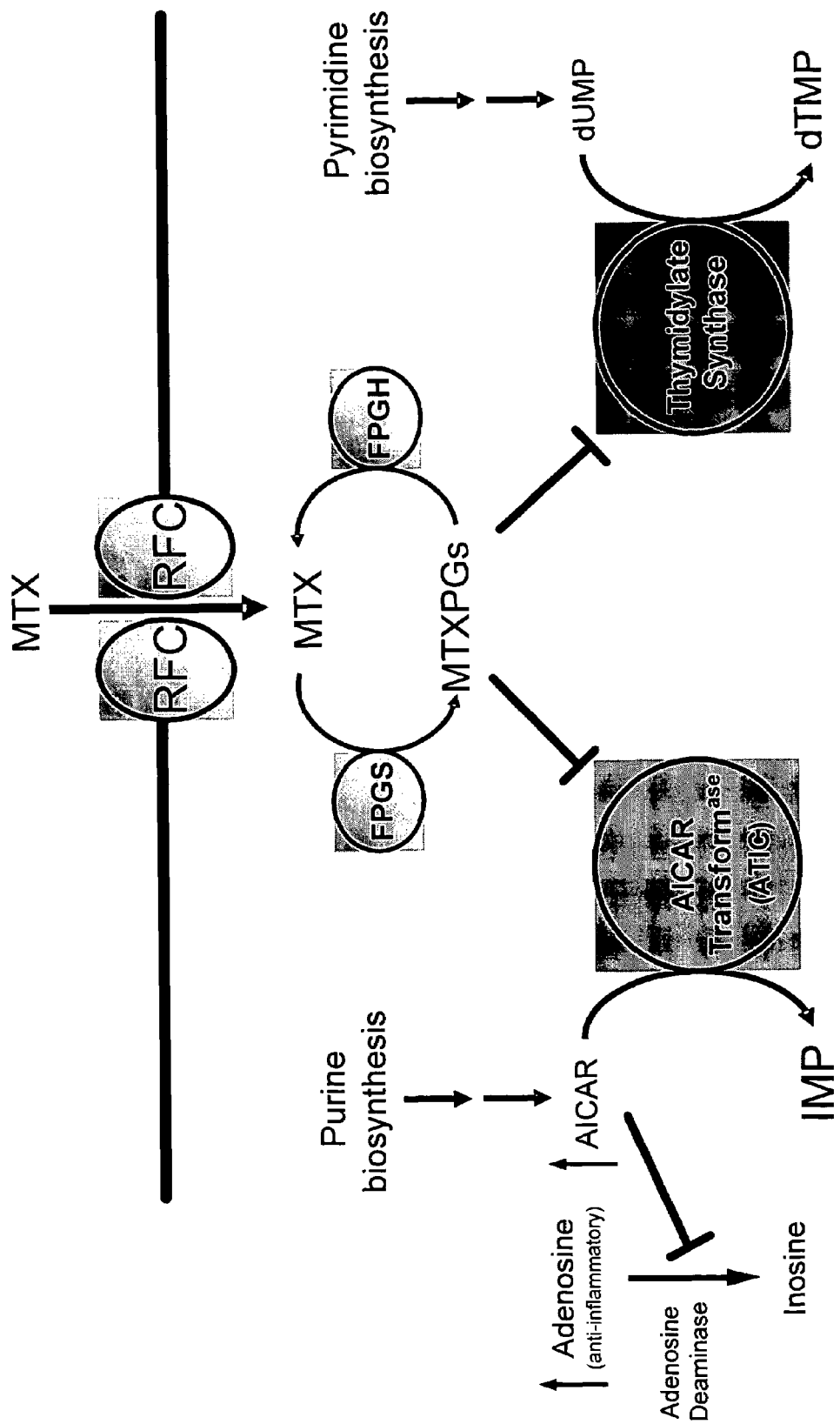
FIG. 1 shows a schematic of methotrexate metabolism and a proposed mechanism for the anti-inflammatory effects of methotrexate. Methotrexate (MTX) and reduced folate enter the cell through the reduced folate carrier (RFC-1). Methotrexate is converted to various methotrexate polyglutamates (MTXPGs) by folylpolyglutamate synthase (FPGS), a process in competition with folylpolyglutamate hydrolase (FPGH). MTXPGs inhibit the last enzyme in the de novo purine synthesis pathway, 5-amino-imidazole carboxamide ribonucleotide transformylase (ATIC), whereby accumulation of amino-imidazole carboxamide ribonucleotide (AICAR) and inhibition of adenosine deaminase (ADA) result in increased levels of the anti-inflammatory agent, adenosine. MTXPGs also inhibit an enzyme in the de novo pyrimidine synthesis pathway, thymidylate synthase (TS).
Figure 5:
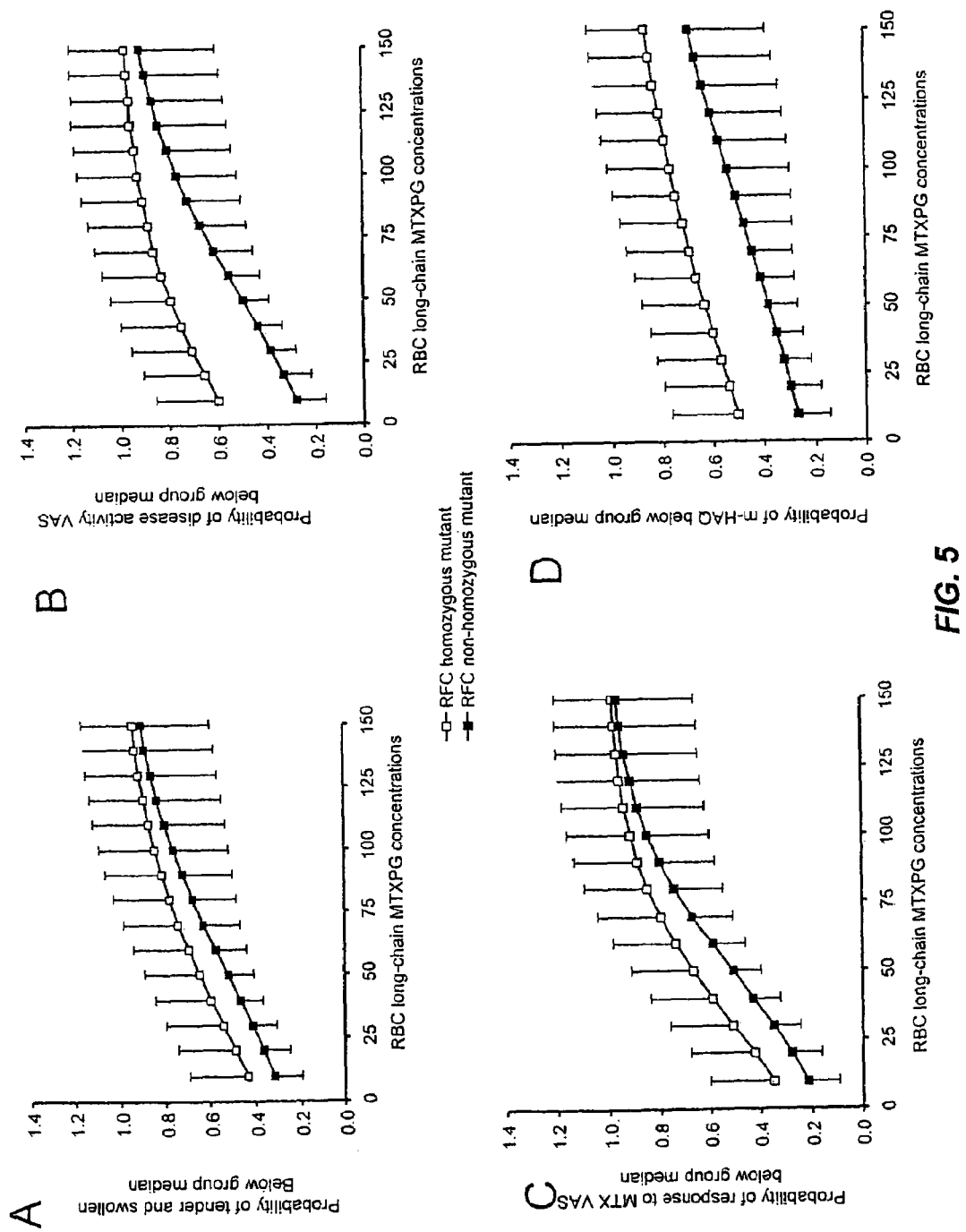
FIG. 5 shows the contribution of the reduced folate carrier G80A homozygous mutant genotype to the effect of methotrexate. A logistic regression equation with standard error of the estimates and p values is given. Panel A: Probability P of a total number of tender and swollen joints below group median. $Log(1/1-P)=-1.00\pm0.42+0.022\pm0.009\times MTXPG_3+0.52\pm0.52\times RFC-1$. $MTXPG_3$: p=0.015; RFC-1: p=0.31. Panel B: Probability P of a Physician Assessment of Disease Activity VAS below group median. $Log(1/1-P)=-1.18\pm0.44+0.024\pm0.009\times MTXPG_3+1.34+0.57\times RFC-1$. $MTXPG_3$: p=0.010; RFC-1: p=0.019. Panel C: Probability P of a Physician Assessment of Response to methotrexate VAS below group median (which corresponds to a perception of response to MTX above median). $Log(1/1-P)=-1.62\pm0.46+0.033\pm0.010\times MTXPG_3+0.66\pm0.54\times RFC-1$. $MTXPG_3$: p=0.001; RFC-1: p=0.22. Panel D: Probability P of a modified health assessment questionnaire below group median. $Log(1/1-P)=-1.14\pm0.43+0.015\pm0.008\times MTXPG_3+0.79\pm0.53\times RFC-1$. $MTXPG_3$: p=0.08; RFC-1: p=0.04.
Figure 6:
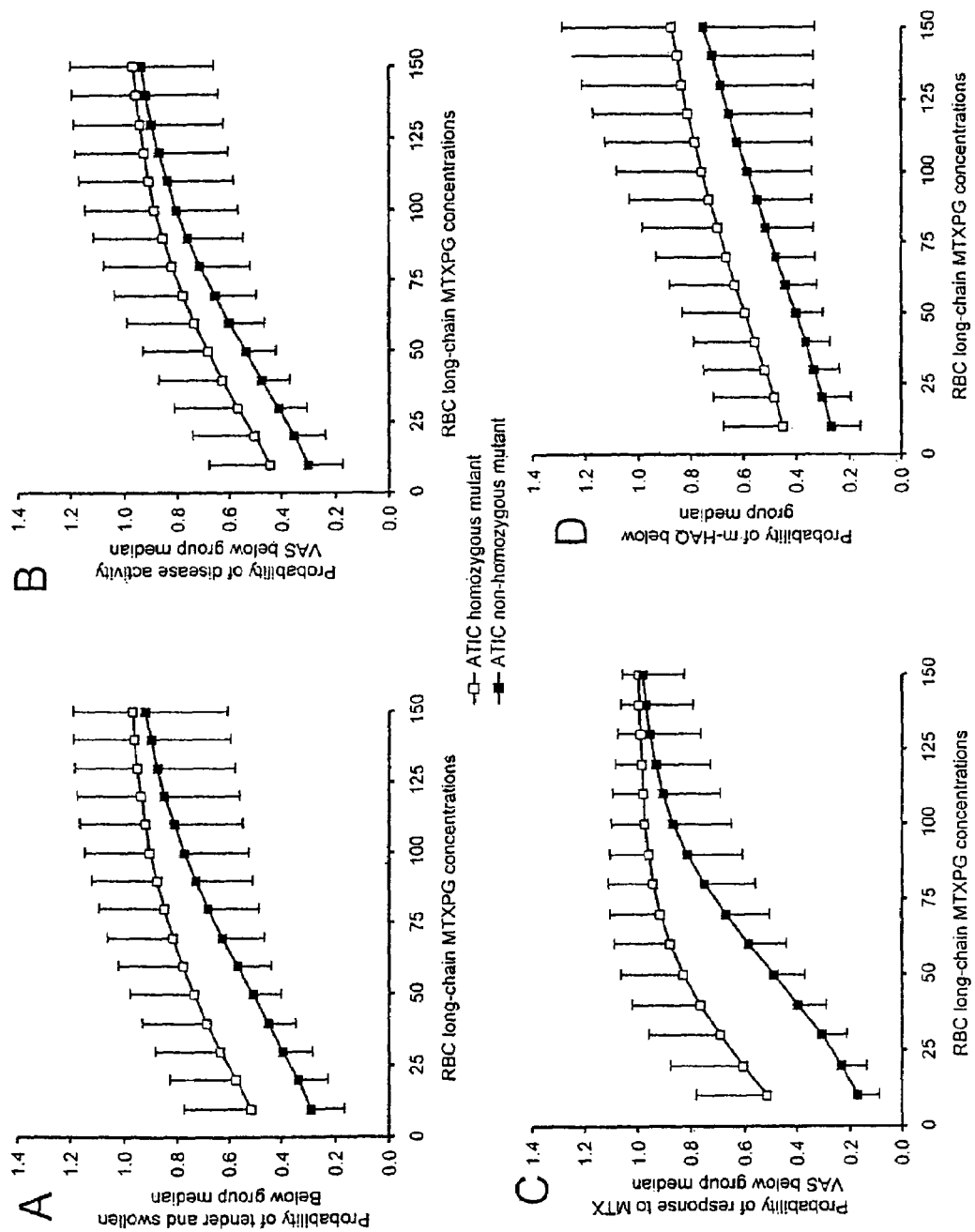
FIG. 6 shows the contribution of the ATIC C347G homozygous mutant genotype to the effect of methotrexate. A logistic regression equation with standard error of the estimates and p values is given. Panel A: Probability P of a total number of tender and swollen joints below group median. $Log(1/1-P)=-1.13\pm0.44+0.024\pm0.009\times MTXPG_3+0.96\pm0.57\times ATIC$. $MTXPG_3$: p=0.009; ATIC: p=0.089. Panel B: Probability P of a physician assessment of Disease activity VAS below group median. $Log(1/1-P)=-1.10\pm0.44+0.025\pm0.009\times MTXPG_3+0.61\pm0.55\times ATIC$. $MTXPG_3$: p=0.006; ATIC: p=0.26. Panel C: Probability P of a physician assessment of response to methotrexate VAS below group median (which corresponds to a perception of response to MTX above median). $Log(1/1-P)=-1.96\pm0.51+0.038\pm0.010\times MTXPG_3+1.62\pm0.63\times ATIC_{0/1}$. $MTXPG_3$: p<0.001; ATIC: P=0.010. Panel D: Probability P of a modified health assessment questionnaire below group median. $Log(1/1-P)=-1.13\pm0.42+0.013\pm0.008\times MTXPG_3+1.03\pm0.51\times ATIC$. $MTXPG_3$: p=0.12; ATIC: p=0.14.

As further disclosed herein in Example 2, several genetic variants were associated with superior clinical responsiveness to methotrexate therapy. Firstly, as shown in FIG. 5, rheumatoid arthritis patients carrying the homozygous mutant RFC-1 genotype (RFC-1 80A/A) were more likely to have an above-median response to methotrexate than those with other genotypes. Furthermore, an allelic variant in ATIC, a fundamental component of the de novo purine synthesis pathway, was identified as correlating with patient responsiveness to methotrexate therapy. As shown in Example 2 and FIG. 6, patients with a homozygous mutant ATIC 347G/G genotype had an increased probability of clinical responsiveness to methotrexate above group median. These results indicate that rheumatoid arthritis patients carrying the ATIC homozygous mutant genotype 347G/G can have superior clinical responsiveness to chemotherapeutics such as methotrexate as compared to patients with other genotypes at this SNP. These results also are consistent with the anti-inflammatory effects of methotrexate occurring, at least in part, through inhibition of ATIC (see, FIG. 1).

Figure 7:
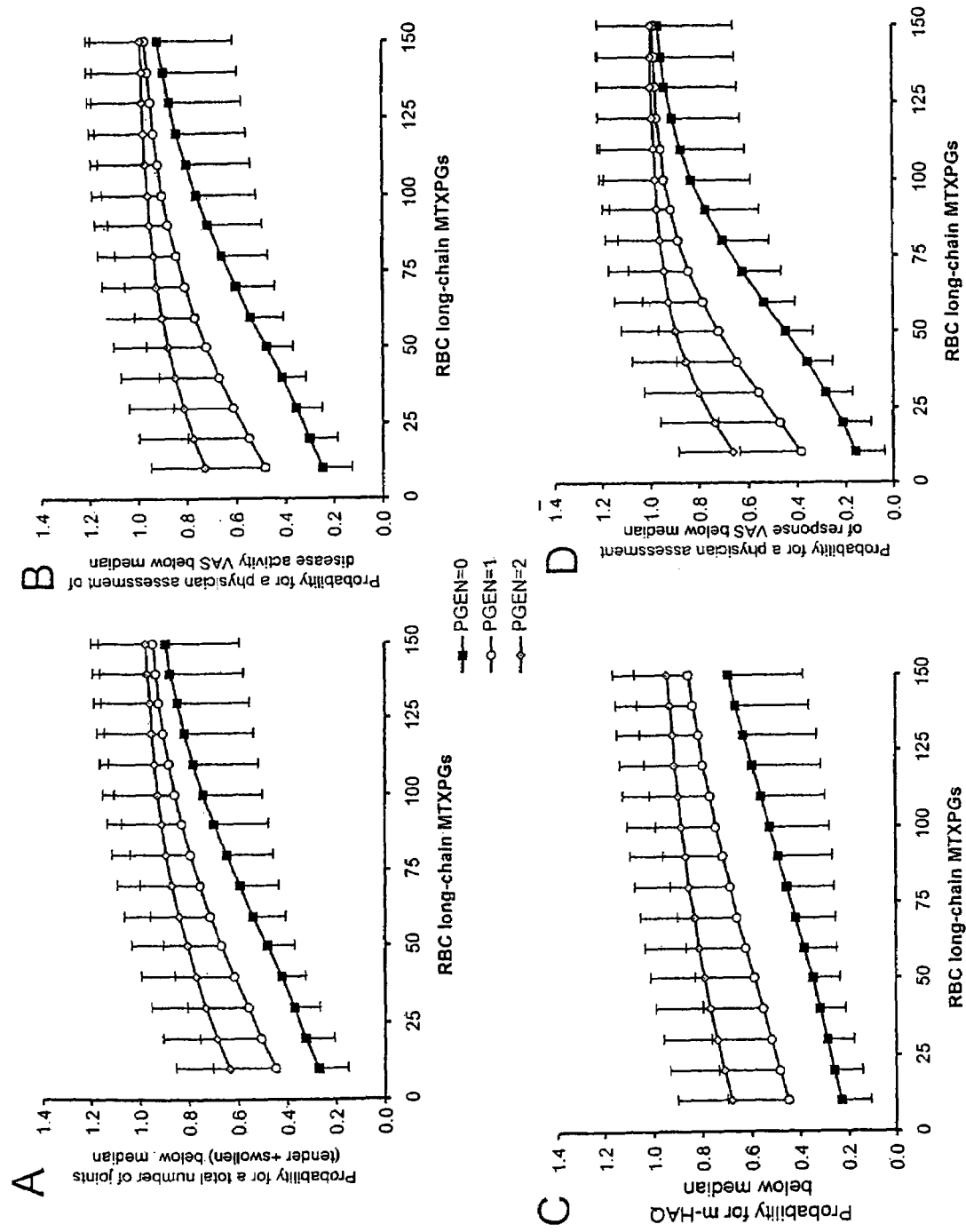
FIG. 7 shows the contribution of the pharmacogenetic index (PGENi) to the effect of methotrexate, where PGENi is expressed as the sum of the variant homozygous genotypes in RFC-1 and ATIC carried by the patients. A logistic regression equation with standard error of the estimates and p values is given. Panel A: Probability P of a total number of tender and swollen joints below group median. $Log(1/1-P)=-1.20\pm0.45+0.023\pm0.009\times MTXPG_3+0.76\pm0.39\times PGENi$. $MTXPG_3$: p=0.012; PGENi: p=0.052. Panel B: Probability P of a physician assessment of Disease activity VAS below group median. $Log(1/1-P)=-1.37\pm0.47+0.025\pm0.009\times MTXPG_3+0.61\pm0.55\times PGENi$. $MTXPG_3$: p=0.006; PGENi: p=0.011. Panel C: Probability P of a physician assessment of response to methotrexate VAS below group median (which corresponds to a perception of response to MTX above median). $Log(1/1-P)=-2.03\pm0.51+0.036\pm0.010\times MTXPG_3+1.04\pm0.413\times PGENi$. $MTXPG_3$: p<0.001; PGENi: p=0.011. Panel D: Probability P of a modified health assessment questionnaire below group median. $Log(1/1-P)=-1.35\pm0.46+0.014\pm0.009\times MTXPG_3+1.03\pm0.51\times PGENi$. $MTXPG_3$: p=0.007; PGENi: p=0.011.

The sum of variant homozygosities (i.e., the pharmacogenetic index) was further analyzed, together with MTXPG$_3$ levels, for ability of polymorphisms in RFC-1 and/or ATIC to predict an increased probability of responsiveness to chemotherapy in rheumatoid arthritis patients, a lower number of tender and swollen joints, and lower disease activity or lower functional disability in patients with rheumatoid arthritis. As shown in FIG. 7, each of these variables was significantly predicted. These results indicate that analysis of methotrexate tri-glutamate levels as an indicator of long-chain methotrexate polyglutamate levles, combined with determination of a pharmacogenetic index including variant homozygosity for at least two polymorphisms in the folate/de novo purine synthesis pathway, can be advantageous in individualizing methotrexate therapy. Thus, the methods disclosed herein are advantageous in allowing routine individualization of methotrexate and other chemotherapeutic dosages.

Figure 9:
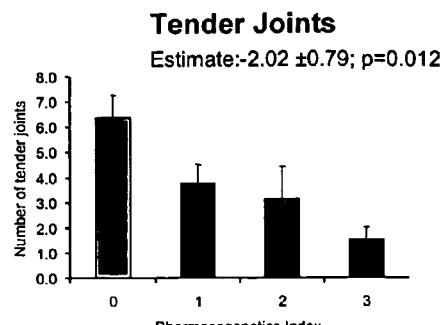
FIG. 9 shows the contribution of the pharmacogenetic index (PGENi) to the effect of methotrexate, where PGENi is expressed as the sum of the variant homozygous genotypes in RFC-1, ATIC, and TS carried by the patients. The PGENi was determined as follows: PGENi=0: no homozygous variant alleles of RFC-1, ATIC, or TS; PGENi=1: any one of the variant alleles is homozygous; PGENi=2: any two of the variant alleles are homozygous; and PGENi=3: all three variant alleles are homozygous. A logistic regression equation with standard error of the estimates and p values is given. Panel A: The number of tender joints in patients for a particular PGENi. The mean number of tender joints is 6.4±0.9 for PGENi=0 (n=58 patients) and 3.3±0.9 for PGENi=1 to 3 (n=50 patients), with a P value of 0.048. Panel B: The number of swollen joints in patients for a particular PGENi. The mean number of swollen joints is 5.5±0.8 for PGENi=0 (n=58 patients) and 2.3±0.4 for PGENi=1 to 3 (n=50 patients), with a P value of 0.019. Panel C: The physician's assessment of disease activity visual analog score (VAS) for a particular PGENi. The mean number of the VAS is 4.1±0.3 for PGENi=0 (n=58 patients) and 2.6±0.3 for PGENi=1 to 3 (n=50 patients), with a P value of 0.0008. Panel D: The modified health assessment questionnaire (MHAQ) score for a particular PGENi. The mean number of the mHAQ score is 0.68±0.07 for PGENi=0 (n=58 patients) and 0.39±0.06 for PGENi=1 to 3 (n=50 patients), with a P value of 0.009. Panel E: The physician's assessment of response to MTX for a particular PGENi. The mean number of the response to MTX is 3.0±0.2 for PGENi=0 (n=58 patients) and 2.3±0.3 for PGENi=1 to 3 (n=50 patients), with a P value of 0.012.
Figure 9:
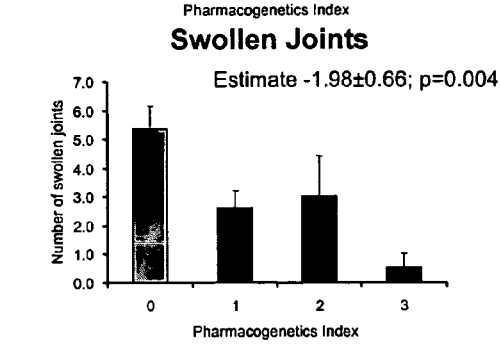
Figure 9:
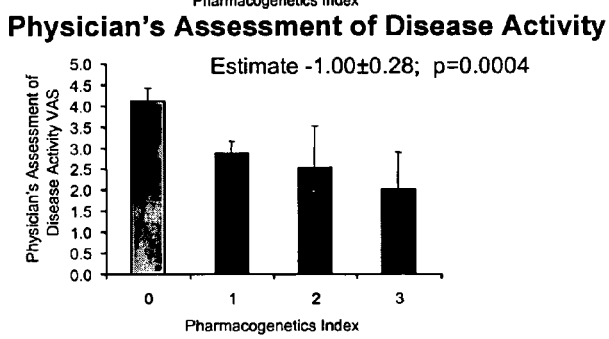
Figure 9:
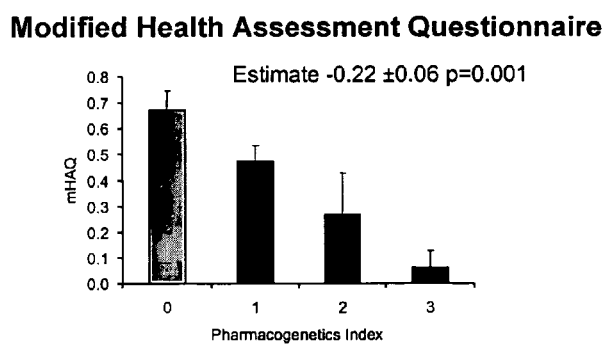
Figure 9:
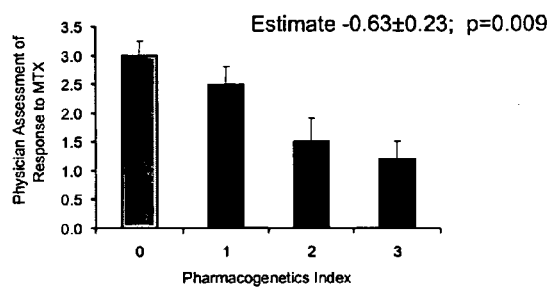

In addition, an allelic variant in thymidylate synthase (TS), a fundamental component of the de novo pyrimidine synthesis pathway, was identified as correlating with patient responsiveness to methotrexate therapy. As shown in FIG. 9, patients with homozygous variant allele genotypes for TS (two 28 base pair tandem repeats, "2TR/2TR" or "TSER*2/TSER*2"), RFC-1, and ATIC (i.e., PGENi=3) have a lower number of tender and swollen joints, a lower physician's assessment of disease activity visual analog score (VAS), a lower modified health assessment questionnaire (mHAQ) score, and a better physician's assessment of response to MTX than patients with no homozygous variant alleles (i.e., PGENi=0) or patients with single (i.e., PGENi=1) or pairwise combinations (i.e., PGENi=2) of homozygous variant alleles.

Based on the above discoveries, the present invention provides a method for optimizing clinical responsiveness to chemotherapy in an individual by genotyping the individual at a polymorphic site in a reduced folate carrier (RFC-1) gene, where the presence of a variant allele at the polymorphic site is indicative of a characteristic clinical responsiveness to the chemotherapy. In a method of the invention, the chemotherapy can be, for example, methotrexate therapy, and the individual can have, for example, rheumatoid arthritis.

Any of a variety of polymorphic sites in an RFC-1 gene can be genotyped in a method of the invention including, without limitation, those in an RFC-1 coding region. In one embodiment, the RFC-1 variant allele is associated with decreased RFC-1 protein activity. Heterozygosity (1 copy) or homozygosity (2 copies) of such a variant allele can be indicative, for example, of either superior or inferior clinical responsiveness to chemotherapy such as methotrexate therapy. In another embodiment, the RFC-1 variant allele is associated with increased RFC-1 protein activity. Heterozygosity (1 copy) or homozygosity (2 copies) of such a variant allele can be indicative, for example, of either superior or inferior clinical responsiveness to chemotherapy, for example, methotrexate therapy.

Polymorphic sites in RFC-1 useful in the present invention include, but are not limited to, single nucleotide polymorphisms (SNPs). In one embodiment, the RFC-1 SNP comprises a G to A mutation at nucleotide 80. In another embodiment, RFC-1 80A variant allele heterozygosity or homozygosity is indicative of superior clinical responsiveness to the chemotherapy.

The present invention also provides a method for optimizing clinical responsiveness to chemotherapy in an individual by genotyping the individual at a polymorphic site in an aminoimidazole carboxamide ribonucleotide transformylase (ATIC) gene, where the presence of a variant allele at the polymorphic site is indicative of a characteristic clinical responsiveness to the chemotherapy. In a method of the invention, the chemotherapy can be, for example, methotrexate therapy, and the individual can have, for example, rheumatoid arthritis.

Any of a variety of polymorphic sites in an ATIC gene can be genotyped in a method of the invention including, without limitation, those in an ATIC coding region. In one embodiment, the ATIC variant allele is associated with decreased ATIC enzymatic activity. Heterozygosity (1 copy) or homozygosity (2 copies) of such a variant allele can be indicative, for example, of either superior or inferior clinical responsiveness to chemotherapy such as methotrexate therapy. In another embodiment, the ATIC variant allele is associated with increased ATIC enzymatic activity. Heterozygosity (1 copy) or homozygosity (2 copies) of such a variant allele can be indicative, for example, of either superior or inferior clinical responsiveness to chemotherapy, for example, methotrexate therapy.

Polymorphic sites in ATIC useful in the present invention include, but are not limited to, single nucleotide polymorphisms (SNPs). In one embodiment, the ATIC SNP comprises a C to G mutation at nucleotide 347. In another embodiment, ATIC 347G variant allele heterozygosity or homozygosity is indicative of superior clinical responsiveness to the chemotherapy.

The present invention further provides a method for optimizing clinical responsiveness to chemotherapy in an individual by genotyping the individual at a polymorphic site in a thymidylate synthase (TS) gene, where the presence of a variant allele at the polymorphic site is indicative of a characteristic clinical responsiveness to the chemotherapy. In a method of the invention, the chemotherapy can be, for example, methotrexate therapy, and the individual can have, for example, rheumatoid arthritis.

Any of a variety of polymorphic sites in a TS gene can be genotyped in a method of the present invention including, without limitation, those in a TS coding region and non-coding region such as a promoter. In one embodiment, the TS variant allele is associated with decreased TS enzymatic activity. Heterozygosity (1 copy) or homozygosity (2 copies) of such a variant allele can be indicative, for example, of either superior or inferior clinical responsiveness to chemotherapy such as methotrexate therapy. In another embodiment, the TS variant allele is associated with increased TS enzymatic activity. Heterozygosity (1 copy) or homozygosity (2 copies) of such a variant allele can be indicative, for example, of either superior or inferior clinical responsiveness to chemotherapy, for example, methotrexate therapy.

Polymorphic sites in TS useful in the present invention include, but are not limited to, single nucleotide polymorphisms (SNPs) and tandem repeats (TRs). In one embodiment, the TS TR consists of two 28 base pair tandem repeats (2TR). In another embodiment, TS 2TR variant allele heterozygosity or homozygosity is indicative of superior clinical responsiveness to the chemotherapy.

The present invention further provides a method for optimizing clinical responsiveness to chemotherapy in an individual by genotyping the individual at a polymorphic site in any combination of an RFC-1 gene and/or an ATIC-1 gene and/or a TS gene, where the presence of a variant allele in RFC-1, ATIC, or TS at one or more of the polymorphic sites is indicative of a characteristic clinical responsiveness to the chemotherapy.

The reduced folate carrier (RFC-1) is well known in the art as described in Matherly, *Prog. Nucl. Acid Res.* 67:131-162 (2001)). The human RFC-1 coding sequence is available as Genbank accession AH006305, and genomic RFC-1 sequence is available under Genbank accessions U92873, U92872, U92871, U92870, U92869 and U92868.

Any of a variety of cellular extracts are useful in a method of the invention for optimizing clinical responsiveness to chemotherapy, including, but not limited to, red blood cellular extracts. Long-chain MTXPGs such as $MTXPG_3$ and, if desired, other MTXPGs such as $MTXPG_4$ and/or $MTXPG_5$ (SEQ ID NO:12) can be resolved, for example, using chromatography such as high pressure liquid chromatography (HPLC). Detection of the long-chain MTXPGs can be performed using, for example, fluorimetry, spectrophotometry, or mass spectrometry.

Aminoimidazole carboxamide ribonucleotide transformylase/inosine monophosphate cyclohydrolase (ATIC) is a bifunctional enzyme catalyzing the last two steps in the de novo purine biosynthetic nucleotide pathway. The penultimate step, 5-aminoimidazole-4-carboxamide ribonucleotide transformylase (AICAR Tfase), involves the transfer of the formyl group from a reduced folate substrate, (6R)N10-formyltetrahydrofolate (10-f-FH4) to the exocyclic amino group of AICAR to form 5-formylaminoimidazole-4-carboxide ribonucleotide (FAICAR). The final step in the pathway, inosine monophosphate cyclohydrolase (IMPCHase), is a ring closure reaction of FAICAR, forming inosine 5' monophosphate (IMP) and a molecule of water. Human ATIC was cloned as described in Rayl et al., *J. Biol. Chem.* 271:2225-2233 (1996), and has been characterized as described in Vergis et al., *J. Biol. Chem.* 276:7727-7733 (2001). The human ATIC nucleotide coding sequence is provided herein as SEQ ID NO: 1, and the human ATIC amino acid sequence is provided herein as SEQ ID NO: 2 (FIG. 20, panels A and B, respectively). The human ATIC cDNA sequence also is available as GenBank accession NM_004044, and the human ATIC genomic sequence is available as GenBank NT_005403.

C. Diseases and Disorders

The methods of the present invention can be useful for optimizing clinical responsiveness in any individual treated with chemotherapy such as methotrexate therapy, including low-dose and high-dose methotrexate therapy. In one embodiment, a method of the present invention is used to optimize clinical responsiveness to chemotherapy in a human having an autoimmune disease such as rheumatoid arthritis or an inflammatory disease. As used herein, the term "arthritis" means an inflammatory condition that affects joints. Arthritis can be, without limitation, infective, autoimmune, or traumatic in origin; the term arthritis includes, but is not limited to, acute arthritis, acute gouty arthritis, bacterial arthritis, chronic inflammatory arthritis, degenerative arthritis (osteoarthritis), infectious arthritis, juvenile arthritis, mycotic arthritis, neuropathic arthritis, polyarthritis, proliferative arthritis, psoriatic arthritis, juvenile rheumatoid arthritis, rheumatoid arthritis, venereal arthritis, and viral arthritis.

In another embodiment, a method of the invention is used to optimize clinical responsiveness to chemotherapy in a human having rheumatoid arthritis. Rheumatoid arthritis is a chronic systemic disease primarily of the joints and is usually polyarticular, marked by inflammatory changes in the synovial membranes and articular structures and by muscle atrophy and rarefaction of the bones. Methotrexate is widely used in the treatment of rheumatoid arthritis, and one skilled in the art recognizes that the methods of the invention can be practiced with a cellular extract from a human or other mammal having rheumatoid arthritis or another form of arthritis.

In yet another embodiment, a method of the present invention is used to optimize clinical responsiveness to chemotherapy in a human having cancer. The term "cancer" is intended to mean any member of a class of diseases characterized by the uncontrolled growth of aberrant cells. The term includes all known cancers and neoplastic conditions, whether characterized as malignant, benign, soft tissue or solid, and cancers of all stages and grades including pre- and post-metastatic cancers. The term cancer encompasses, without limitation, leukemias such as acute lymphocytic leukemia and acute myelocytic leukemia; lymphomas; choriocarcinomas; head and neck cancers; and osteogenic sarcomas, each of which are widely treated with methotrexate. The term cancer further includes, but is not limited to, digestive and gastrointestinal cancers such as anal cancer, bile duct cancer, gastrointestinal carcinoid tumors and colon cancer; esophageal cancer, gallbladder cancer, liver cancer, pancreatic cancer, rectal cancer, appendix cancer, small intestine cancer and stomach (gastric) cancer; breast cancer; ovarian cancer; lung cancer; renal cancer; cancer of the central nervous system; and skin cancer. In one embodiment, a method of the present invention is used to optimize clinical responsiveness to chemotherapy in a human having leukemia.

D. Variant Alleles

The methods of the invention rely on genotyping an individual to detect particular variant alleles, for example, at polymorphic sites in ATIC, RFC-1, or TS. As used herein, the term "variant allele" means a stably heritable molecular variation that results in altered gene product levels or activity. Thus, a variant ATIC allele is a stably heritable molecular variation that results in altered ATIC levels or activity. Similarly, a variant RFC-1 allele is a stably heritable molecular variation that results in altered RFC-1 levels or activity. Likewise, a variant TS allele is a stably heritable molecular variation that results in altered TS levels or activity. One skilled in the art will know of suitable variant alleles in folate pathway genes, purine synthesis genes, pyrimidine synthesis genes, and cytokine synthesis genes for genotyping in the methods of the present invention.

Variant alleles useful in the invention include, without limitation, single nucleotide polymorphisms (SNP), microsatellites (ms), variable number tandem repeat (VNTR) polymorphisms, and substitutions, insertions or deletions of one or more nucleotides. One skilled in the art understands that a variant allele also can be a molecular variation such as abnormal methylation or other modification that does not produce a difference in the primary nucleotide sequence of the variant allele as compared to the wild type allele.

A variant allele at a polymorphic site in an ATIC gene is located within the ATIC locus, which includes coding regions of the ATIC gene as well as non-coding regions such as introns and 5' and 3' untranslated regions. One skilled in the art understands that such a variant allele can be at a polymorphic site within, for example, a promoter region 5' of ATIC coding sequence, within an enhancer region 5' or 3' of ATIC coding sequence or within an intronic sequence, or an mRNA stability region 3' of ATIC coding sequence. In one embodiment, the variant allele at a polymorphic site in an ATIC gene is located within the ATIC coding sequence.

In further embodiments, a variant allele at a polymorphic site in an ATIC gene results in decreased ATIC levels or enzymatic activity. Homozygosity, heterozygosity, or compound heterozygosity of such ATIC variant alleles can be associated with either superior or inferior clinical responsiveness to chemotherapy such as methotrexate therapy, as compared to clinical responsiveness in an individual having a wild-type genotype. In further embodiments, a variant allele at a polymorphic site in an ATIC gene results in increased ATIC levels or enzymatic activity.

A variant allele at a polymorphic site in an RFC-1 gene is located within the RFC-1 locus, which includes coding regions of the RFC-1 gene as well as non-coding regions such as introns and 5' and 3' untranslated regions. One skilled in the art understands that such a variant allele can be at a polymorphic site within, for example, a promoter region 5' of the RFC-1 coding sequence, within an enhancer region 5' or 3' of RFC-1 coding sequence or within an intronic sequence or an mRNA stability region 3' of RFC-1 coding sequence. In one embodiment, the variant allele at a polymorphic site in an RFC-1 gene is located within the RFC-1 coding sequence.

In further embodiments, a variant allele at a polymorphic site in an RFC-1 gene results in decreased RFC-1 levels or activity. Homozygosity, heterozygosity, or compound heterozygosity of such RFC-1 variant alleles can be associated with either superior or inferior clinical responsiveness to chemotherapy such as methotrexate therapy, as compared to clinical responsiveness in an individual having a wild-type genotype. In further embodiments, a variant allele at a polymorphic site in an RFC-1 gene results in increased RFC-1 levels or activity.

A variant allele at a polymorphic site in a TS gene is located within the TS locus, which includes coding regions of the TS gene as well as non-coding regions such as introns and 5' and 3' untranslated regions. One skilled in the art understands that such a variant allele can be at a polymorphic site within, for example, a promoter region 5' of the TS coding sequence, within an enhancer region 5' or 3' of TS coding sequence or within an intronic sequence or an mRNA stability region 3' of TS coding sequence. In one embodiment, the variant allele at a polymorphic site in a TS gene is located within the TS coding sequence.

In further embodiments, a variant allele at a polymorphic site in a TS gene results in decreased a TS levels or enzymatic activity. Homozygosity, heterozygosity, or compound heterozygosity of such TS variant alleles can be associated with either superior or inferior clinical responsiveness to chemotherapy such as methotrexate therapy, as compared to clinical responsiveness in an individual having a wild-type genotype. In further embodiments, a variant allele at a polymorphic site in a TS gene results in increased TS levels or enzymatic activity.

E. Methods of Genotyping

A variety of means can be used to genotype an individual at a polymorphic ATIC, RFC-1, or TS site in a method of the present invention. As an example, enzymatic amplification of nucleic acid from an individual can be conveniently used to obtain nucleic acid for subsequent analysis. The presence or absence of an ATIC, RFC-1, or TS variant allele also can be determined directly from the individual's nucleic acid without enzymatic amplification.

Genotyping of nucleic acid from an individual, whether amplified or not, can be performed using any of various techniques. Useful techniques include, without limitation, polymerase chain reaction based analysis, sequence analysis and electrophoretic analysis, which can be used alone or in combination. As used herein, the term nucleic acid means a polynucleotide such as a single- or double-stranded DNA or RNA molecule including, for example, genomic DNA, cDNA and mRNA. This term encompasses nucleic acid molecules of both natural and synthetic origin as well as molecules of linear, circular or branched configuration representing either the sense or antisense strand, or both, of a native nucleic acid molecule. It is understood that such nucleic acids can be unpurified, purified, or attached, for example, to a synthetic material such as a bead or column matrix.

Material containing nucleic acid is routinely obtained from individuals. Such material is any biological matter from which nucleic acid can be prepared. As non-limiting examples, material can be whole blood, plasma, saliva, cheek swab, or other bodily fluid or tissue that contains nucleic acid. In one embodiment, a method of the invention is practiced with whole blood, which can be obtained readily by non-invasive means and used to prepare genomic DNA. In one embodiment, genotyping involves amplification of an individual's nucleic acid using the polymerase chain reaction (PCR). Use of the polymerase chain reaction for the amplification of nucleic acids is well known in the art (see, for example, Mullis et al. (Eds.), *The Polymerase Chain Reaction*, Birkhäuser, Boston, (1994)). In another embodiment, polymerase chain reaction amplification is performed using one or more fluorescently labeled primers. In a further embodiment, polymerase chain reaction amplification is performed using one or more labeled or unlabeled primers that contain a DNA minor grove binder.

Any of a variety of different primers can be used to amplify an individual's nucleic acid by the polymerase chain reaction. For example, the PCR primers disclosed in Example 1 can be used to amplify the ATIC sequence surrounding the C347G polymorphic site. As understood by one skilled in the art, additional primers for PCR analysis can be designed based on the sequence flanking the polymorphic site of interest. As a non-limiting example, a sequence primer can contain about 15 to 30 nucleotides of a sequence upstream or downstream of the polymorphic site of interest. Such primers generally are designed to have sufficient guanine and cytosine content to attain a high melting temperature which allows for a stable annealing step in the amplification reaction. Several computer programs, such as Primer Select, are available to aid in the design of PCR primers.

A Taqman® allelic discrimination assay available from Applied Biosystems can be useful for genotyping an individual at a polymorphic site and thereby determining the presence or absence of a variant allele. In a Taqman® allelic discrimination assay such as the ATIC assay disclosed in Example 1, a specific, fluorescent, dye-labeled probe for each allele is constructed. The probes contain different fluorescent reporter dyes such as FAM and VIC to differentiate amplification of each allele. In addition, each probe has a quencher dye at one end which quenches fluorescence by fluorescence resonance energy transfer. During PCR, each probe anneals specifically to complementary sequences in the nucleic acid from the individual. The 5' nuclease activity of Taq polymerase is used to cleave only probe that hybridizes to the allele. Cleavage separates the reporter dye from the quencher dye, resulting in increased fluorescence by the reporter dye. Thus, the fluorescence signal generated by PCR amplification indicates which alleles are present in the sample. Mismatches between a probe and allele reduce the efficiency of both probe hybridization and cleavage by Taq polymerase, resulting in little to no fluorescent signal. Those skilled in the art understand that improved specificity in allelic discrimination assays can be achieved by conjugating a DNA minor grove binder (MGB) group to a DNA probe as described, for example, in Kutyavin et al., *Nuc. Acids Research* 28:655-661 (2000). Minor grove binders include, but are not limited to, compounds such as dihydrocyclopyrroloindole tripeptide (DPI3).

Sequence analysis also can be useful genotyping an individual at a polymorphic site. A variant allele can be detected by sequence analysis using the appropriate primers, which are designed based on the sequence flanking the polymorphic site of interest, as is known by those skilled in the art. As a non-limiting example, a sequence primer can contain about 15 to 30 nucleotides of a sequence about 40 to 400 base pairs upstream or downstream of the polymorphic site of interest. Such primers are generally designed to have sufficient guanine and cytosine content to attain a high melting temperature which allows for a stable annealing step in the sequencing reaction.

The term "sequence analysis" means any manual or automated process by which the order of nucleotides in a nucleic acid is determined. As an example, sequence analysis can be used to determine the nucleotide sequence of a sample of DNA. The term sequence analysis encompasses, without limitation, chemical and enzymatic methods such as dideoxy enzymatic methods including, for example, Maxam-Gilbert and Sanger sequencing as well as variations thereof. The term sequence analysis further encompasses, but is not limited to, capillary array DNA sequencing, which relies on capillary electrophoresis and laser-induced fluorescence detection and can be performed using instruments such as the MegaBACE 1000 or ABI 3700. As additional non-limiting examples, the term sequence analysis encompasses thermal cycle sequencing (Sears et al., *Biotechniques* 13:626-633 (1992)); solid-phase sequencing (Zimmerman et al., *Methods Mol. Cell Biol.* 3:39-42 (1992); and sequencing with mass spectrometry, such as matrix-assisted laser desorption/ionization time-of-flight mass spectrometry (MALDI-TOF MS; Fu et al., *Nature Biotech.* 16:381-384 (1998)). The term sequence analysis further includes, yet is not limited to, sequencing by hybridization (SBH), which relies on an array of all possible short oligonucleotides to identify a segment of sequence (Chee et al., *Science* 274:610-614 (1996); Drmanac et al., *Science* 260:1649-1652 (1993); and Drmanac et al., *Nature Biotech.* 16:54-58 (1998)). One skilled in the art understands that these and additional variations are encompassed by the term sequence analysis as defined herein. See, in general, Ausubel et al., supra, Chapter 7 and supplement 47.

Electrophoretic analysis also can be useful in genotyping an individual according to a method of the invention. "Electrophoretic analysis", as used herein in reference to one or more nucleic acids such as amplified fragments, means a process whereby charged molecules are moved through a stationary medium under the influence of an electric field. Electrophoretic migration separates nucleic acids primarily on the basis of their charge, which is in proportion to their size, with smaller molecules migrating more quickly. The term electrophoretic analysis includes, without limitation, analysis using slab gel electrophoresis, such as agarose or polyacrylamide gel electrophoresis, or capillary electrophoresis. Capillary electrophoretic analysis generally occurs inside a small-diameter (50-100-m) quartz capillary in the presence of high (kilovolt-level) separating voltages with separation times of a few minutes. Using capillary electrophoretic analysis, nucleic acids are conveniently detected by UV absorption or fluorescent labeling, and single-base resolution can be obtained on fragments up to several hundred base pairs. Such methods of electrophoretic analysis, and variations thereof, are well known in the art, as described, for example, in Ausubel et al., *Current Protocols in Molecular Biology* Chapter 2 (Supplement 45) John Wiley & Sons, Inc. New York (1999). Restriction fragment length polymorphism (RFLP) analysis also can be useful for genotyping an individual at a polymorphic ATIC, RFC-1, or TS site in a method of the present invention (Jarcho et al. in *Dracopoli* et al., *Current Protocols in Human Genetics* pages 2.7.1-2.7.5, John Wiley & Sons, New York; Innis et al.,(Ed.), *PCR Protocols*, San Diego: Academic Press, Inc. (1990)). As used herein, restriction fragment length polymorphism analysis is any method for distinguishing polymorphic alleles using a restriction enzyme, which is an endonuclease that catalyzes degradation of nucleic acid following recognition of a specific base sequence, generally a palindrome or inverted repeat. One skilled in the art understands that the use of RFLP analysis depends upon an enzyme that can differentiate a variant allele from a wild-type or other allele at a polymorphic site.

Allele-specific oligonucleotide hybridization also can be useful for genotyping an individual in a method of the present invention. Allele-specific oligonucleotide hybridization is based on the use of a labeled oligonucleotide probe having a sequence perfectly complementary, for example, to the sequence encompassing the variant allele. Under appropriate conditions, the variant allele-specific probe hybridizes to a nucleic acid containing the variant allele but does not hybridize to the one or more other alleles, which have one or more nucleotide mismatches as compared to the probe. If desired, a second allele-specific oligonucleotide probe that matches an alternate (e.g., wild-type) allele also can be used. Similarly, the technique of allele-specific oligonucleotide amplification can be used to selectively amplify, for example, a variant allele by using an allele-specific oligonucleotide primer that is perfectly complementary to the nucleotide sequence of the variant allele but which has one or more mismatches as compared to other alleles (Mullis et al., supra, 1994). One skilled in the art understands that the one or more nucleotide mismatches that distinguish between the variant and other alleles are often located in the center of an allele-specific oligonucleotide primer to be used in the allele-specific oligonucleotide hybridization. In contrast, an allele-specific oligonucleotide primer to be used in PCR amplification generally contains the one or more nucleotide mismatches that distinguish between the variant and other alleles at the 3' end of the primer.

A heteroduplex mobility assay (HMA) is another well-known assay that can be used for genotyping at a polymorphic site in a method of the present invention. HMA is useful for detecting the presence of a variant allele since a DNA duplex carrying a mismatch has reduced mobility in a polyacrylamide gel compared to the mobility of a perfectly base-paired duplex (Delwart et al., *Science* 262:1257-1261 (1993); White et al., *Genomics* 12:301-306 (1992)).

The technique of single strand conformational polymorphism (SSCP) also can be useful for genotyping at a polymorphic site in a method of the present invention (see, Hayashi, *Methods Applic.* 1:34-38 (1991)). This technique is used to detect variant alleles based on differences in the secondary structure of single-stranded DNA that produce an altered electrophoretic mobility upon non-denaturing gel electrophoresis. Variant alleles are detected by comparison of the electrophoretic pattern of the test fragment to corresponding standard fragments containing known alleles.

Denaturing gradient gel electrophoresis (DGGE) also can be useful in a method of the present invention. In DGGE, double-stranded DNA is electrophoresed in a gel containing an increasing concentration of denaturant; double-stranded fragments made up of mismatched alleles have segments that melt more rapidly, causing such fragments to migrate differently as compared to perfectly complementary sequences (Sheffield et al., "Identifying DNA Polymorphisms by Denaturing Gradient Gel Electrophoresis" in Innis et al., supra, 1990).

Other molecular methods useful for genotyping an individual at a polymorphic site also are known in the art and useful in the methods of the present invention. Other well-known genotyping approaches include, without limitation, automated sequencing and RNAase mismatch techniques (Winter et al., *Proc. Natl. Acad. Sci.* 82:7575-7579 (1985)). Furthermore, one skilled in the art understands that, where the presence or absence of multiple variant alleles is to be determined, individual variant alleles can be detected by any combination of molecular methods. See, in general, Birren et al. (Eds.) *Genome Analysis: A Laboratory Manual* Volume 1 (Analyzing DNA) New York, Cold Spring Harbor Laboratory Press (1997). In addition, one skilled in the art understands that multiple variant alleles can be detected in individual reactions or in a single reaction (a "multiplex" assay).

In view of the above, one skilled in the art realizes that the methods of the invention for optimizing clinical responsiveness to chemotherapy by genotyping an individual at a polymorphic site can be practiced using one or any combination of the well-known assays described above or other assays known in the art.

F. Methods of Resolving and Detecting Methotrexate Polyglutamates

Where a level of a methotrexate polyglutamate (MTXPG) is determined in a sample such as red blood cells or a cellular extract in a method of the present invention, the term "level" means the amount or concentration of the MTXPG in the sample. It is understood that a level can be an absolute level such as a molar concentration or weight or a relative level such as a percent or fraction compared to one or more other molecules in the sample.

As used herein, the phrase "resolving at least one long-chain MTXPG" refers to sufficiently separating at least one long-chain MTXPG from short-chain MTXPGs and other molecules to allow determination of a level of the at least one long-chain MTXPG (e.g., $MTXPG_3$, alone or in combination with one or more of $MTXPG_4$, $MTXPG_5$ (SEQ ID NO:12), $MTXPG_6$ (SEQ ID NO:15), and $MTXPG_7$ (SEQ ID NO:14)). Thus, resolving the at least one long-chain MTXPG which has an observable property involves sufficiently separating the at least one long-chain MTXPG species from other molecules having the same property. As a non-limiting example, $MTXPG_3$, which is detectable by fluorescence at a particular excitation and emission wavelength, can be resolved by separating it from other molecules that have substantial excitation and emission at the same wavelengths; the $MTXPG_3$ species may or may not be separated from a variety of other molecules having different excitation and emission wavelengths. In view of the foregoing, it is understood that whether or not the at least one long-chain MTXPG is resolved is determined, in part, by the detection means utilized in the method. In one embodiment, $MTXPG_3$ alone is resolved. In a further embodiment, $MTXPG_3$, together with $MTXPG_4$ and $MTXPG_5$ (SEQ ID NO:12), are resolved.

Long-chain MTXPGs such as $MTXPG_3$ can be chromatographically resolved from other cellular components using reverse phase chromatography as set forth in Examples 3 and 4 and subsequently quantitated, for example, by comparison to one or more known reference standards. As demonstrated herein, chromatographic resolution of MTXPGs can be performed by passing a mixture of MTXPGs in a cellular extract through a C18 reverse phase column in a mobile phase consisting of a 20 minute linear gradient from 2% acetonitrile/ 98% mobile phase A to 12.5% acetonitrile/87.5% mobile phase A, wherein mobile phase A is 10 mM ammonium acetate, pH 6.5, with hydrogen peroxide at a final concentration of 0.2% (see, Examples 3 and 4).

A reverse phase column useful for resolving long-chain MTXPGs such as $MTXPG_3$ in a cellular extract can have, for example, dimensions of 25 cm×4.6 mm, as exemplified herein. It is understood that columns having larger or smaller diameters, lengths or both can also be used, for example, to accommodate larger or smaller sample sizes. Flow rates can vary, without limitation, from 0.2 to 2.5 ml/minute. As demonstrated herein, the flow rate for the mobile phase was 1 ml/minute. However, the flow rate of the mobile phase can be altered as desired. A slower flow rate, such as 0.8 ml/minute, 0.5 ml/minute or 0.2 ml/minute, can be used, for example, with a smaller column or to increase MTXPG retention times. Alternatively, a faster flow rate, such as 1.5 ml/minute or 2.0 ml/minute, can be used, for example, with a larger column or to decrease MTXPG retention times.

Long-chain MTXPGs such as $MTXPG_3$ can be resolved from the components of a cellular extract by any of a variety of methods including chromatographic and spectrometric methods and other methods such as those that serve to separate molecules based on size or charge. Examples of useful chromatographic methods include, without limitation, liquid and gas phase chromatographic methods such as, without limitation, ion exchange chromatography, size exclusion chromatography, iso-electric focusing, gel electrophoresis, capillary electrophoresis, normal phase chromatography (e.g., HPLC), reverse phase chromatography (e.g., RP-HPLC), and affinity chromatography. Exemplary, but not limiting, spectrometric methods are mass spectrometry, tandem mass spectrometry, and preparative mass spectrometry with electrospray ionization. It is understood that, if desired, two or more different techniques can be combined to resolve the at least one long-chain MTXPG in a method of the present invention. As a non-limiting example, soluble molecules can be separated from proteins and other precipitated materials after cell lysis and perchloric acid precipitation, followed by HPLC of the soluble molecules.

A cellular extract derived, for example, from an individual treated with methotrexate typically contains a mixture of methotrexate polyglutamated species, which differ in the number of attached glutamate moieties. As used herein, the term "cellular extract" means a mixture containing a heterogenous plurality of cellular components. A cellular extract useful in the invention can contain, for example, a heterogeneous plurality of soluble cellular compounds, proteins and metabolites and can be derived from a single cell type, mixture of cell types or tissue source. Heterogeneity of a cellular extract can be characterized by various criteria. According to one criteria, a cellular extract useful in the invention is heterogeneous with respect to the variety of cellular components present in the extract; such a cellular extract can contain, without limitation, at least 100, 1000, $1 \times 10^4$ or $1 \times 10^5$ or more different cellular components, for example, at least 100, 1000, $1 \times 10^4$ or $1 \times 10^5$ or more different cellular proteins. Heterogeneity can also be expressed a percentage of the total number of different components of the cell from which the extract is derived. As an example, a cellular extract can contain cellular components representing at least 5%, 10%, 15%, 20%, 25%, 50% or 75% of the variety of components present in the cell from which the extract was derived. Heterogeneity can also be determined based on the percentage of any one cellular component in a cellular extract compared to the totality of other components in the cellular extract. Thus, a cellular extract useful in the invention can be a mixture in which any one cellular component represents at most 90%, 80%, 70%, 60%, 50%, 25%, or 10% of totality of other cellular components by weight in the extract. A cellular extract useful in a method of the invention can contain mixtures of components such as proteins, components that are larger than 100 Da or components that absorb radiation between about 303 nm and 313 nm or at about 370 nm.

A cellular extract useful in a method of the invention can be any cellular extract that contains at least one long-chain MTXPG such as $MTXPG_3$. It is understood that additional exogenous MTXPGs can be added, if desired, to a cellular extract. The addition of one or more exogenous MTXPGs into a cellular extract can be useful for determining a standard curve for quantification or for optimizing detection conditions.

Cellular extracts useful in the invention can be prepared from a cell or tissue using methods well known in the art. Those skilled in the art will know or be able to determine an appropriate method for obtaining source cells based on their location and characteristics. As an example, red blood cells and other blood cells can be obtained by harvesting through intravenous routes. Cells can also be removed from tissues using known biopsy methods including, for example, those utilizing an open surgical incision, biopsy needle, or endoscope. Cells can be lysed by any of a variety of means depending, in part, on the properties of the cell. As non-limiting examples, cells can be lysed by mechanical disruption with glass beads, a Dounce homogenizer, french press, or sonication; enzymatic disruption with lysozyme or other enzyme that degrades the cell wall; osmotic disruption or a combination of these methods.

A cellular extract useful in a method of the invention can be a partially purified extract, which can be, for example, enriched in MTXPGs. As a non-limiting example, an extract can be partially purified by centrifugation to remove insoluble material such as membranes and large cellular structures (see, Example 3). Partial purification to separate cellular components including MTXPGs or analogs thereof from other cellular components can include, without limitation, centrifugation, protein precipitation, liquid-liquid extraction, solid-phase extraction, or chromatography such as reverse phase chromatography, ion pairing chromatography or ion exchange chromatography, as described, for example, in Rubino, *J. Chromatog.* 764:217-254 (2001). Additional methods that can be used to obtain and partially purify cellular extracts are well known in the art, as described, for example, in Scopes, *Protein Purification: Principles and Practice,* 3rd Ed., Springer-Verlag, New York (1994) and Coligan et al., *Current Protocols in Protein Science*, John Wiley and Sons, Baltimore, Md. (2000).

Where long-chain MTXPGs such as $MTXPG_3$ are resolved in a cellular extract in a method of the present invention, proteinaceous material can be precipitated away from the MTXPGs and other metabolites, and the protein-depleted supernatant subjected to further separation procedures. As used herein, the term "acid" refers to a reagent that is capable of effecting preferential precipitation of proteinaceous material from solution, without precipitating MTXPGs. One skilled in the art understands that an acid useful in the invention does not substantially destroy, degrade or otherwise affect detection of the MTXPGs. Exemplary acids useful in the invention include, without limitation, perchloric acid; sulfuric acid, phosphoric acid and glacial acetic acid. Additional acids useful in the invention can be identified by the ability to yield substantially similar MTXPG levels for a particular sample, as compared to a sample contacted with 70% perchloric acid.

Red blood cellular extracts are useful for detecting resolved long-chain MTXPGs such as $MTXPG_3$ in a method of the present invention, as demonstrated in Examples 3 and 4. The conditions exemplified herein can also be readily applied to other types of cellular extracts. It is understood that the cellular extract can be from a cell that is a target for methotrexate therapy or otherwise is a cell indicative of efficacy or toxicity of methotrexate therapy. Non-limiting examples of cellular extracts that are useful for detecting resolved long-chain MTXPGs include extracts prepared from tissue biopsies, erythrocytes, neutrophils, and leukocytes. Additional cellular extracts useful for detecting resolved long-chain MTXPGs include, without limitation, neoplastic or cancer cell extracts such as those obtained from any of the specific cancers set forth herein. Cellular extracts useful for detecting resolved long-chain MTXPGs further include, but are not limited to, eukaryotic cellular extracts, mammalian cellular extracts, primate cellular extracts, human cellular extracts, non-human primate cellular extracts, rat cellular extracts, mouse cellular extracts, cat cellular extracts, dog cellular extracts, bird cellular extracts, and horse cellular extracts. The resolved long-chain MTXPGs can be detected in a cellular extract, for example, by resolving the long-chain MTXPGs in the cellular extract; irradiating the long-chain MTXPGs, thereby producing a resolved fluorescent long-chain MTXPG photolytic products; and detecting the resolved fluorescent long-chain MTXPG photolytic products, thereby determining a level of the long-chain MTXPGs. As non-limiting examples, a level of $MTXPG_3$ or $MTXPG_{3-5}$ (SEQ ID NO:13) can be determined. Long-chain MTXPGs such as $MTXPG_3$ can be resolved, without limitation, using chromatography such as high performance liquid chromatography (HPLC). In a method of the present invention, long-chain MTXPGs such as $MTXPG_3$ can be irradiated, for example, using UV irradiation such as UV irradiation in a solvent having 0.05% to 1% $H_2O_2$. In other embodiments, long-chain MTXPGs such as $MTXPG_3$ can be UV irradiated in a solvent having 0.1% to 0.3% $H_2O_2$, UV irradiated using radiation having a wavelength in the range of 225 nm to 275 nm such as a wavelength of 254 nm, or UV irradiated for a duration of 0.5 to 60 seconds or 0.5 to 15 seconds.

The resolved fluorescent long-chain MTXPG photolytic products can be detected, for example, by detecting fluorescence upon excitation in the range of 240 nm to 420 nm, for example, detecting fluorescence upon excitation with UV radiation in the range of 240 nm to 300 nm such as upon excitation with UV radiation at 274 nm. Fluorescence can also be detected upon excitation with UV radiation in the range of 360 nm to 410 nm. It is understood that fluorescence is detected at an appropriate emission wavelength, such as an emission wavelength in the range of 320 nm to 550 nm, or an emission wavelength in the range of 440 nm to 500 nm such as an emission wavelength of 464 mm. Fluorescence can also be detected upon excitation with UV radiation at 274 nm and at an emission wavelength of 464 mm.

As disclosed herein, fluorescent MTXPG photolytic products can be produced by irradiation of MTXPGs. The term "photolytic product," as used herein, means a molecule that is produced by cleavage of bonds in MTXPG that are electronically excited by radiation. The process of producing a photolytic product is referred to as photolysis. Photolysis of long-chain MTXPGs such as $MTXPG_3$ to produce "long-chain MTXPG photolytic products" can be performed, for example, with UV light, which is a term understood in the art to include light of any wavelength in the range of about 200 to 400 nm. It further is understood that any light source which produces UV light can be useful for irradiating long-chain MTXPGs such as $MTXPG_3$ in a method of the present invention including, for example, a lamp such as an arc lamp or quartz halogen lamp, or a laser. As demonstrated in Example 4, fluorescent MTXPG photolytic products, including fluorescent $MTXPG_3$ photolytic products, were produced by irradiating MTXPGs with a low pressure mercury UV lamp which emits radiation in the range of 225 to 275 nm, with a peak output at 254 nm. It is understood that long-chain MTXPGs such as $MTXPG_3$ can be selectively irradiated with a particular wavelength in the UV range by using an appropriate light source, optical filter or combination of these components in accordance with their known optical characteristics. In a method of the present invention which involves detecting long-chain MTXPG photolytic products, long-chain MTXPGs such as $MTXPG_3$ are irradiated for an appropriate period of time to yield fluorescent long-chain MTXPG photolytic products. In particular embodiments, a method of the present invention is practiced by irradiating long-chain MTXPGs such as $MTXPG_3$ or $MTXPG_{3-5}$ (SEQ ID NO:13) for about 0.5 to 60 seconds or 0.5 to 15 seconds. As non-limiting examples, a method of the present invention can be practiced by irradiating long-chain MTXPGs such as $MTXPG_3$ or $MTXPG_{3-5}$ (SEQ ID NO:13) for about 0.1 to 100 seconds, 0.2 to 60 seconds, 0.5 to 60 seconds, 0.5 to 45 seconds, 0.5 to 30 seconds, 0.5 to 20 seconds, 0.5 to seconds, 0.5 to 10 seconds, 1 to 20 seconds, 1 to seconds, 2 to 20 seconds, or 2 to 10 seconds. As additional non-limiting examples, a method of the present invention can be practiced by irradiating long-chain MTXPGs such as $MTXPG_3$ or $MTXPG_{3-5}$ (SEQ ID NO:13) for about 0.5 to 6 seconds, 0.5 to seconds, 0.5 to 4 seconds, 1 to 6 seconds, 1 to seconds, 1 to 4 seconds, or 2 to 4 seconds. In particular embodiments, a method of the present invention is practiced by irradiating long-chain MTXPGs such as $MTXPG_3$ or $MTXPG_{3-5}$ (SEQ ID NO:13) for about 0.5 to 60 seconds, 0.5 to 15 seconds, or 2 to 4 seconds.

Figure 16:
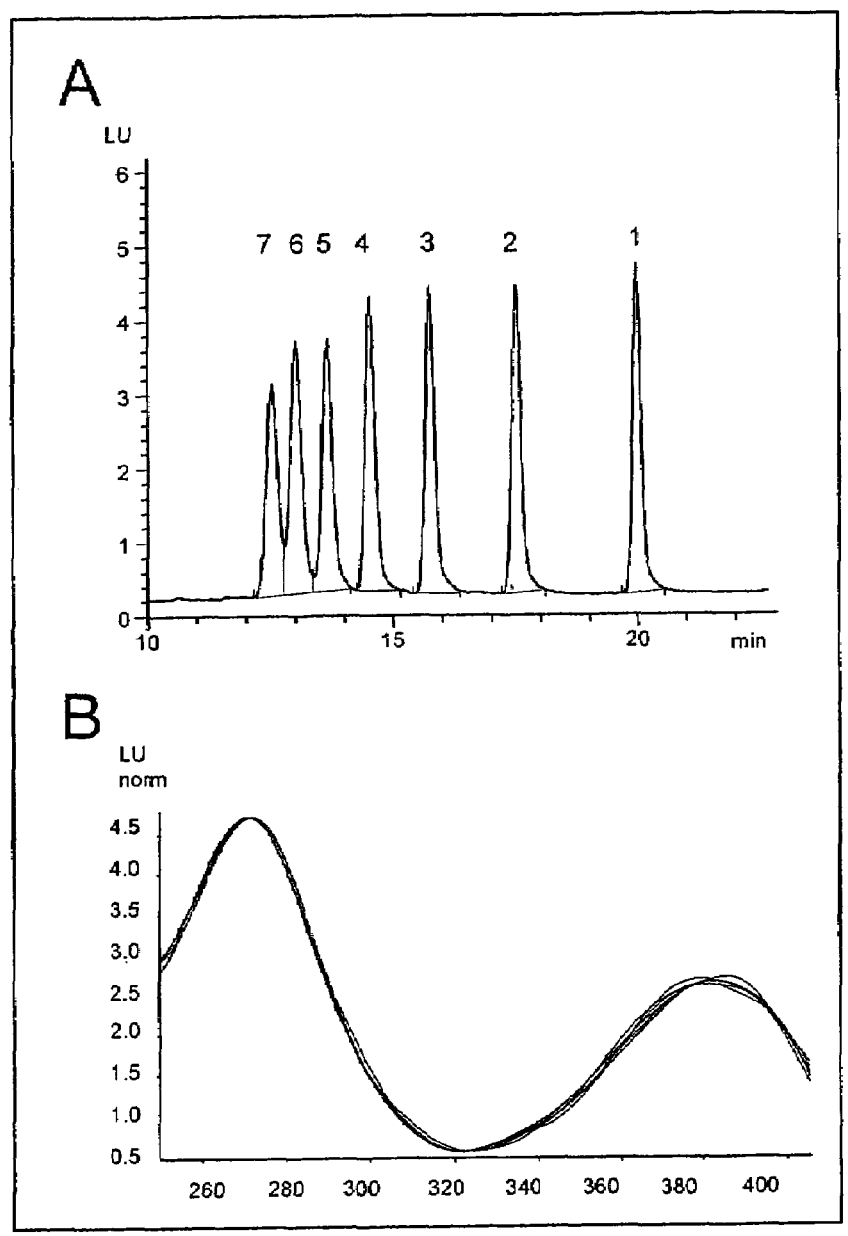
FIG. 16 shows a chromatogram of methotrexate and methotrexate polyglutamates in water and excitation spectra of the photolytic products of these analytes. Panel A: Chromatogram of a standard in water containing all seven methotrexate polyglutamates at a final concentration of 25 nmol/L each. Panel B: Excitation spectra of photolytic products of $MTXPG_1$ through $MTXPG_7$ (SEQ ID NO:14) in water.

As disclosed herein, irradiation of long-chain MTXPGs such as $MTXPG_3$ for three seconds with a 254 nm low pressure mercury ultraviolet lamp produced fluorescent MTXPG photolytic products with overlapping excitation spectra, readily detectable, for example, upon excitation with UV radiation with a wavelength of 274 nm and at an emission wavelength of 464 nm (see, for example, Example 3 and FIG. 16B). It is understood that the time of irradiation can be varied to produce the desired fluorescent long-chain MTXPG photolytic product having characteristic properties as desired for a particular application. A particular fluorescent photolytic product can have, for example, one or more characteristic properties such as characteristic fluorescence excitation and emission peak maxima, and characteristic fluorescence intensity levels depending, for example, upon the pH and amount of acetonitrile present during detection. Photolysis of the long-chain MTXPG such as $MTXPG_3$ can be carried out in the presence of hydrogen peroxide ($H_2O_2$) or another peroxide. As non-limiting examples, when hydrogen peroxide is added during irradiation of long-chain MTXPGs such as $MTXPG_3$ or $MTXPG_{3-5}$ (SEQ ID NO:13), the final concentration can be about 0.03% or higher. In particular embodiments, the final concentration of hydrogen peroxide during photolysis of long-chain MTXPGs such as $MTXPG_3$ or $MTXPG_{3-5}$ (SEQ ID NO:13) is in the range of about 0.05% to 1%, 0.1% to 1%, 0.1% to 0.5%, or 0.1% to 0.3%. A level of long-chain MTXPGs in a cellular extract can be determined based on the level of the corresponding resolved fluorescent MTXPG photolytic products. As one example, the amount or concentration of fluorescent long-chain MTXPG photolytic product can be determined based on the intensity of fluorescence from the photolytic product as illustrated in the examples below. As used herein, the term "fluorescence" means an emission of photons in the ultraviolet (UV), visible (VIS) or infrared (IR) region of the spectrum in response to electronic excitation by radiation. The term "fluorescent," when used in reference to a long-chain MTXPG photolytic product, means a photolytic product that emits photons in the UV, VIS, or IR region of the spectrum in response to electronic excitation by radiation. Thus, a fluorescent long-chain MTXPG photolytic product is a photolytic product derived from long-chain MTXPGs that emit photons in the UV, VIS, or IR region of the spectrum in response to electronic excitation by radiation. A fluorescent long-chain MTXPG photolytic product can be characterized, for example, as emitting photons at a quantum yield of at least 0.01 when excited by radiation in solution. In particular embodiments, a fluorescent long-chain MTXPG photolytic product is characterized by a quantum yield of fluorescence that is at least 0.1, 0.2, 0.3, 0.4, 0.5, 0.6, 0.7, 0.8, 0.9, or higher when excited by radiation in solution.

A fluorescent molecule, such as a fluorescent long-chain MTXPG photolytic product, can also be characterized with respect to its maximum emission wavelength or maximum excitation wavelength. In particular embodiments, a method of the invention involves detecting a resolved fluorescent long-chain MTXPG photolytic product having a maximum excitation wavelength in the infrared, red, orange, yellow, green, blue, violet, or ultraviolet region of the spectrum. In additional embodiments, a method of the invention is practiced by detecting a resolved fluorescent long-chain MTXPG photolytic product having a maximum emission wavelength in the infrared, red, orange, yellow, green, blue, violet, or ultraviolet region of the spectrum.

Fluorescence can be detected in a method of the present invention using any of a variety of excitation sources and emission detectors. Excitation of a fluorescent long-chain MTXPG photolytic product can be achieved, for example, with an excitation source such as a lamp or laser including, without limitation, any of those described above in regard to photolysis. Excitation at a particular wavelength or in a particular wavelength range can be achieved in a method of the invention using, for example, a laser that is tuned to the desired wavelength or a lamp having an output that includes the desired wavelength range. An appropriate optical filter can be placed between the excitation source and the fluorescent long-chain MTXPG photolytic product to further limit the range of wavelengths contacting the fluorescent long-chain MTXPG photolytic product, if desired. As shown in FIG. 16B and set forth in Example 3, each of the seven fluorescent $MTXPG_1$ to $MTXPG_7$ (SEQ ID NO:14) photolytic products has two excitation peaks in the range of 240 nm to 420 nm, including a peak from about 240 nm to 300 nm and a peak from about 360 nm to 410 nm. In particular embodiments of the invention, a fluorescent long-chain MTXPG photolytic product can be detected by excitation at a wavelength in the range of about 240 nm to 420 nm, about 240 nm to 300 nm or about 360 nm to 410 nm. If desired, the methods of the present invention can include excitation at or near the peak of 274 μm or in a range near this peak including, for example, excitation at a wavelength in the range of 250 nm to 300 nm or 260 nm to 285 nm.

Excitation at or near the peak of 385 nm or in a range near this peak can also be useful in a method of the invention including, for example, excitation at a wavelength in the range of 360 nm to 400 nm or 375 nm to 395 run. Emission can be detected from a fluorescent long-chain MTXPG photolytic product using any of a variety of detectors such as, without limitation, a photomultiplier tube, diode, diode array, or charge coupled device camera. A detector that detects light at a particular wavelength or in a particular wavelength range can be useful in a method of the invention. If desired, an optical filter can be placed between the fluorescent long-chain MTXPG photolytic product and the detector to limit the range of wavelengths detected. As disclosed herein, fluorescent $MTXPG_1$ to $MTXPG_7$ (SEQ ID NO:14) photolytic products emit from about 320 run to 550 nm and have a primary emission peak from about 440 nm to 520 nm. In particular embodiments of the present invention, emission from a fluorescent long-chain MTXPG photolytic product can be detected at a wavelength in the range of about 320 run to 550 nm or about 440 nm to 520 nm. If desired, the methods of the present invention can include detection of emission at or near the peak of 464 nm or in a range near this peak including, for example, emission at a wavelength in the range of 430 nm to 510 nm or 450nm to 480 nm.

The content of a solution that is used to detect a resolved long-chain MTXPG, or a photolytic product thereof, can be varied, for example, with respect to pH or acetonitrile content. The pH at which long-chain MTXPGs such as $MTXPG_3$, or photolytic products thereof, are detected can be in the range of, for example, about pH 2 to 8 or in the range of about pH 4 to 7. In particular embodiments, long-chain MTXPGs such as $MTXPG_3$, or photolytic products thereof, can be detected, for example, at pH 4, 4.5, 5, 5.5, 6, 6.5, or 7. The amount of acetonitrile present during detection of long-chain MTXPGs, or photolytic products thereof, can be in the range of, for example, about 0% to 20% or about 10% to 20%. In particular embodiments, the amount of acetonitrile present can be, for example, 5%, 10%, 15% or 20%, or 11%, 11.5%, 12%, 12.5%, 13% or 13.5%. Resolved long-chain MTXPGs can also be detected based on one or more other observable characteristic properties of the MTXPG including, for example, ultraviolet or visible light absorption properties, fluorescence, electrochemical properties, or mass. As non-limiting examples, a resolved long-chain MTXPG such as $MTXPG_3$ can be detected with UV/Vis absorption spectroscopy, fluorimetry, electrochemical detection, or mass spectrometry. Those skilled in the art will know or be able to determine an appropriate means for detecting long-chain MTXPGs such as, without limitation, $MTXPG_3$ or $MTXPG_{3-5}$ (SEQ ID NO:13) based on the accuracy and sensitivity desired and the presence of potentially interfering substances in the particular cellular extract being analyzed. As disclosed in FIG. 4E, a threshold of a red blood cell long-chain MTXPG level of about 60 mol/L defined the point at which a dramatic improvement in clinical responsiveness to chemotherapy was observed. Based on this result, the present invention provides a method for optimizing the therapeutic efficacy of chemotherapy in an individual by calculating a level of at least one long-chain MTXPG in an individual treated with the chemotherapy, where a level of the at least one long-chain MTXPG less than a predetermined threshold indicates a need to increase the amount of the chemotherapy subsequently administered to the individual. In a method of the present invention, the chemotherapy can be, for example, methotrexate therapy. Furthermore, the individual treated with chemotherapy can have, without limitation, rheumatoid arthritis.

The level of long-chain MTXPGs can be, for example, the level of long-chain MTXPGs in red blood cells from the individual. The calculation can be based, for example, on determination of the $MTXPG_3$ level in red blood cells from the individual, or, for example, on determination of $MTXPG_3$, $MTXPG_4$ and/or $MTXPG_5$ (SEQ ID NO:12) levels in red blood cells from the individual. Such levels can be conveniently determined, if desired, following resolution by high performance liquid chromatography (HPLC).

In one embodiment, the predetermined threshold is a level of about 60 nmol/L RBC long-chain MTXPGs. In another embodiment, the predetermined threshold is a level of about 40 nmol/L RBC long-chain MTXPGs. In further embodiments, the predetermined threshold is a level of about 40 nmol/L, 45 nmol/L, 50 nmol/L, 55 nmol/L, 60 nmol/L, 65 nmol/L, 70 nmol/L, 75 nmol/L or 80 nmol/L RBC long-chain MTXPGs. In yet further embodiments, the predetermined threshold is a level of about 10 nmol/L, 20 nmol/L, 30 nmol/L, 40 nmol/L, 50 nmol/L, 60 nmol/L, 70 nmol/L, 80 nmol/L, 90 nmol/L, 100 nmol/L, 110 nmol/L or 120 nmol/L. One skilled in the art understands that in the rheumatoid arthritis patient population studied, a predetermined threshold level of about 60 nmol/L can be useful for optimizing therapeutic responsiveness, and that in other patient populations, the optimal predetermined threshold level may be slightly higher or lower.

IV. EXAMPLES

The following examples are intended to illustrate but not limit the present invention.

Example 1

Methotrexate Tri-Glutamate Concentrations can Predict Clinical Responsiveness to Chemotherapy A. Methods In this cross-sectional study, eligibility was limited to patients of at least 18 years of age who met the revised criteria of the American Rheumatism Association for Rheumatoid Arthritis and had received low dose methotrexate therapy for at least three months. Some patients were on additional medications for rheumatoid arthritis, including low dose corticosteroids (<10 mg day), and folic acid supplementation (1 mg/day). The Institutional Review Board approved the study, and patient consent was obtained.

Patient characteristics were collected at the time of the enrollment in the clinical study. Clinical assessment included a tender joint count, a swollen joint count, a Physician's Assessment of Disease Activity (using a 10 cm visual analog scale (VAS)), and a Patient's Assessment of Physical Function using the modified-Health Assessment Questionnaire (m-HAQ). The mHAQ is the average score obtained on eight items addressed to the patient to assess loss of typical lifestyle activities. Scoring of items within each is from 0 (without any difficulty) to 3 (unable to do). The eight items are as follows: 1: dress yourself, 2: get in and out of bed, 3: lift a full glass to your mouth, 4: walk, 5: wash and dry entire body, 6: bend down and pick up clothing, 7: turn faucets on and off, and 8: get in and out of a car. In addition to these standards, the American College of Rheumatology measures, and a Physician's Assessment of Response to methotrexate scored on a 10 cm visual analogue scale (VAS) were also used. In this visual analogue scale, "0" is defined as a perfect response, while "10" is defined as no response. Based on these definitions, a physician's assessment of response to MTX below group median corresponds to a perception of response above group median. Clinical data were collected on case report forms at the time of the clinical visit, and the physician and each patient were blinded to all laboratory parameters throughout the entire study. Furthermore, using the VAS for the physician's assessment of disease activity and the physician's assessment of response to methotrexate, the highest $25^{th}$ percentiles for disease activity or response to methotrexate were calculated. Chi-square analysis was applied, and odds ratios (OR) were calculated.

Red blood cell methotrexate polyglutamate concentrations were measured as described further below using HPLC-fluorometry with post-column photo-oxidation technique. The technologist in charge of quantification of red blood cell methotrexate polyglutamates was blinded to patients' clinical information.

Genotyping was performed as follows: Whole blood (EDTA) was drawn the day of the clinical visit; genomic DNA was extracted using a Generation Purification Capture Column (Gentra Systems, Inc; Minneapolis, Minn.). The RFC-1 G80A polymorphism, which results in a histidine to arginine substitution at codon 27 of RFC-1, was detected using the PCR RFLP method described in Chango et al., supra, 2000. The ATIC C347G polymorphism, which results in a threonine to serine substitution at position 116 of ATIC, was determined with a real time TaqMan allelic discrimination assay performed using fluorogenic 3'-minor groove binding probes. The forward primer sequence was 5'-CCTG-CAATCTCTATCCCTTTGTAAA-3' (SEQ ID NO:3), and the reverse primer sequence was 5'-TTCTGACTTACCAAT-GTCAATTTGCT-3' (SEQ ID NO:4). Allelic discrimination was performed using the wild-type fluorescent probe 5'-FAM-CCAGGTGTAAGTGTTG-MGB 3' (SEQ ID NO:5) and the mutant fluorescent probe 5'-VIC-TCCAGGTG-TAACTGTT-MGB 3' (SEQ ID NO:6). Final reaction conditions were as follows: 900 nM of each primer, 200 nM of each probe, 5 ng genomic DNA, and a 1×TaqMan master mix (Applied Biosystems; Foster City, Calif.). PCR reactions were incubated for one 2-minute cycle at 50° C., a 10-minute cycle at 95° C., and 40 cycles of 95° C. for 15 seconds, 58° C. for 15 seconds, and finally 60° C. for 45 seconds. Statistical analyses were performed using Statistica (StatSoft Inc., Tulsa, Okla.) essentially as follows. The median value for each outcome variable (total number of swollen and tender joints, mHAQ, Physician Assessment of Disease Activity, and response to methotrexate) was used to dichotomize the population of patients into those having a value above the group median value and those having a value below the group median. Logistic regression analysis was used to assess the association between methotrexate polyglutamate levels (as a continuous variable), genotype (0: non-homozygous mutant genotype; 1: homozygous mutant genotype), pharmacogenetics index and outcome variables. The probability of the event (above or below median as appropriate) was derived from the equation: $\text{Log }(1/1-P)=B_0+B_1\times MTXPG+B_2\times X_2$, where $X_2$ corresponds to a genotypic variable. Results are expressed as mean or estimate with standard error. A total of 108 patients (76 females and 32 males) who were undergoing methotrexate therapy for at least three months were enrolled in a cross sectional observational study. The median for duration of methotrexate treatment was 65 months, within a range of 4 to 266 months. Of the total patients, ninety-one (84%) received folic acid supplementation, while 53 patients (49%) were on concomitant steroids. The median weekly methotrexate dose was 14 mg, and the range was 5 to mg/week). Demographic data are presented in Table 1.

TABLE 1

Clinical and Laboratory Characteristics of the 108 patients enrolled in a cross sectional clinical study.

| Parameter | Median (range) |
|---|---|
| Methotrexate dose (mg/week) | 15.0 (5.0-25) |
| Erythrocyte sedimentation rate (mm/hr) | 23 (1-204) |
| Number of swollen and tender joints (total number) | 5.5 (0-44) |
| Physician assessment of disease activity (10 cm VAS score) | 2.9 (0.1-8.4) |

TABLE 1-continued

Clinical and Laboratory Characteristics of the 108 patients enrolled in a cross sectional clinical study.

| Parameter | Median (range) |
|---|---|
| Modified Health Assessment Questionnaire (mHAQ score) | 0.375 (0-2) |
| Physician assessment of response to methotrexate (10 cm VAS score) | 2.1 (0.1-8.3) |

B. MTXPG$_3$ Concentration Correlates with Long-Chain MTXPG Concentrations

Total red blood cell (RBC) methotrexate polyglutamate concentrations (MTXPG$_{1-5}$; (SEQ ID NO:16) were 113 nmol/L (range: 0-322 nmol/L). Because long-chain methotrexate polyglutamates are more effective than short-chain methotrexate polyglutamates at inhibiting amino-imidazole carboxamide ribonucleotide transformylase (ATIC), total long-chain methotrexate polyglutamates were calculated. The tri-order of glutamation (i.e., MTXPG$_3$) was considered as the cut-off for long-chain methotrexate polyglutamates.

Under this criteria, the total long-chain methotrexate polyglutamate concentration (sum of MTXPG$_3$, MTXPG$_4$ and MTXPG$_5$ (SEQ ID NO:12)), denoted "MTXPG$_{3-5}$," (SEQ ID NO:13), was 51 nmol/L (0-203 nmol/L). One patient presented no detectable methotrexate polyglutamates but was not removed from the intent to treat analysis.

The concentration of methotrexate tri-glutamates (MTXPG$_3$) predominated over all long-chain methotrexate polyglutamates. Levels of MTXPG$_3$ were analyzed in the above-described population of rheumatoid arthritis patients as a predictor of long-chain methotrexate polyglutamate concentrations. As shown in FIG. 3B, a strong correlation ($R^2$=0.94) was identified between total long-chain methotrexate polyglutamate concentration (sum of MTXPG$_3$, MTXPG$_4$ and MTXPG$_5$ (SEQ ID NO:12)) and the concentration of MTXPG$_3$. Thus, MTXPG$_3$ concentration was used as a surrogate for long-chain MTXPG concentration in subsequent analyses.

Figure 4:
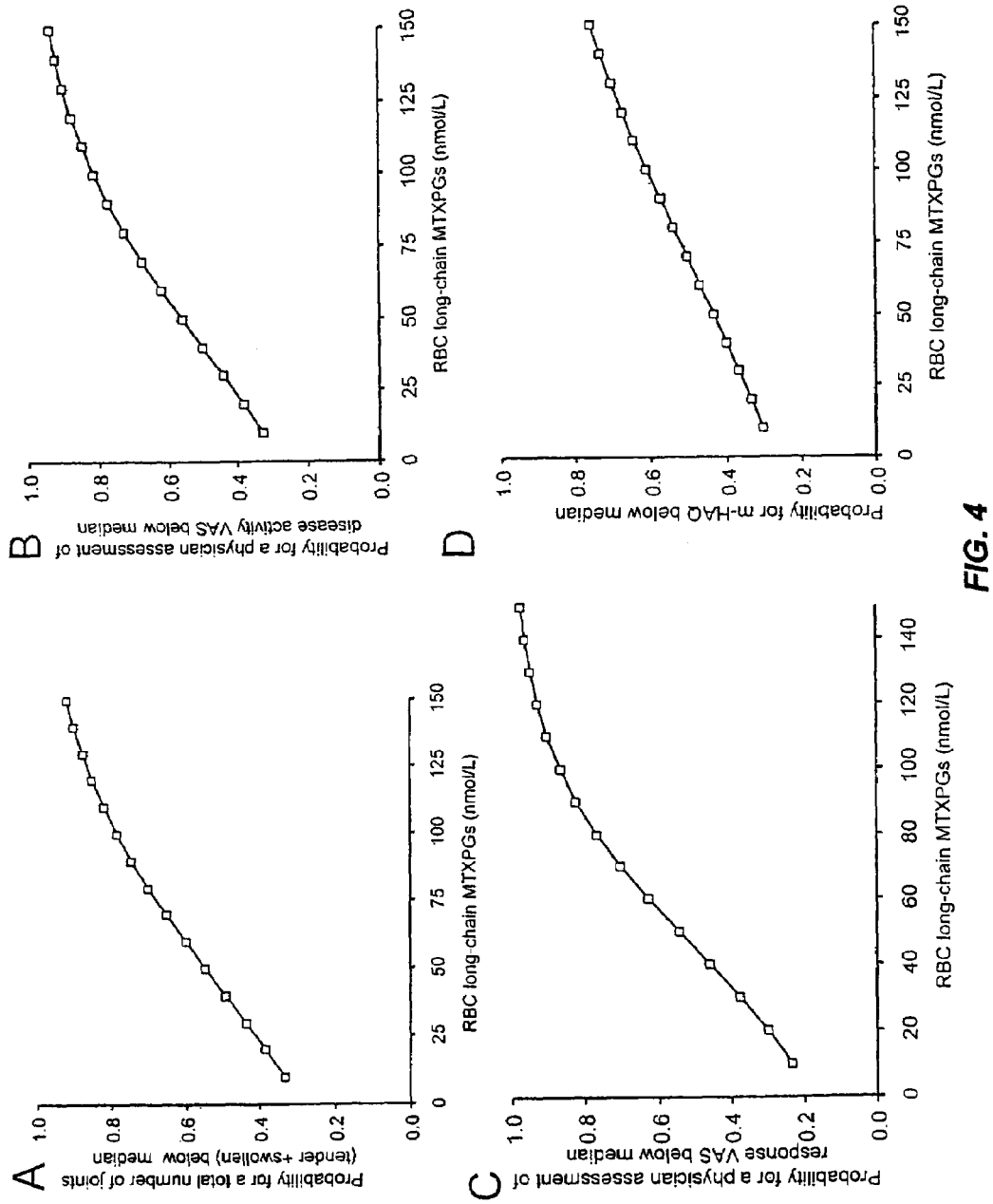
FIG. 4 shows the relationship between red blood cell long-chain MTXPG concentration and the effect of methotrexate. A logistic regression equation with standard error of the estimates and p values is given. Panel A: Probability P of a total number of tender and swollen joints below group median. $Log(1/1-P)=-0.92\pm0.41+0.022\pm0.008\times MTXPG_3$. $MTXPG_3$: p=0.012. Panel B: Probability P of a Physician Assessment of Disease Activity VAS below group median. $Log(1/1-P)=-0.96\pm0.42+0.024\pm0.009\times MTXPG_3$. $MTXPG_3$: p=0.007. Panel C: Probability P of a Physician Assessment of Response to methotrexate VAS below group median (which corresponds to a perception of response to MTX above median). $Log(1/1-P)=-1.53\pm0.455+0.034\pm0.01\times MTXPG_3$. $MTXPG_3$: p=0.007. Panel D: Probability P of a modified health assessment questionnaire (mHAQ) below group median. $Log(1/1-P)=-0.97\pm0.41+0.014\pm0.008\times MTXPG_3$. $MTXPG_3$: p=0.08. Panel E: Relationship between increasing levels of $MTXPG_3$ and increasing likelihood of response above group median.

C. Association Between Red Blood Cell Long-Chain MTXPG Concentrations and Clinical Responsiveness As shown in FIG. 4, in a given patient increasing concentrations of red blood cell long-chain methotrexate polyglutamates were significantly associated with an increased probability of a total number of tender and swollen joints below group median (p=0.012; FIG. 4A), an increased probability of a physician assessment of a disease activity VAS score below group median (p=0.007; FIG. 4B), and an increased probability for a physician assessment of response to methotrexate above median (p=0.001; FIG. 4C). Furthermore, as shown in FIG. 4D, increasing red blood cell long-chain methotrexate polyglutamate concentration tended to be associated with an increased probability for a mHAQ below group median (p=0.08). Methotrexate polyglutamate concentrations were not associated with erythrocyte sedimentation rate (ESR).

Figure 4E:
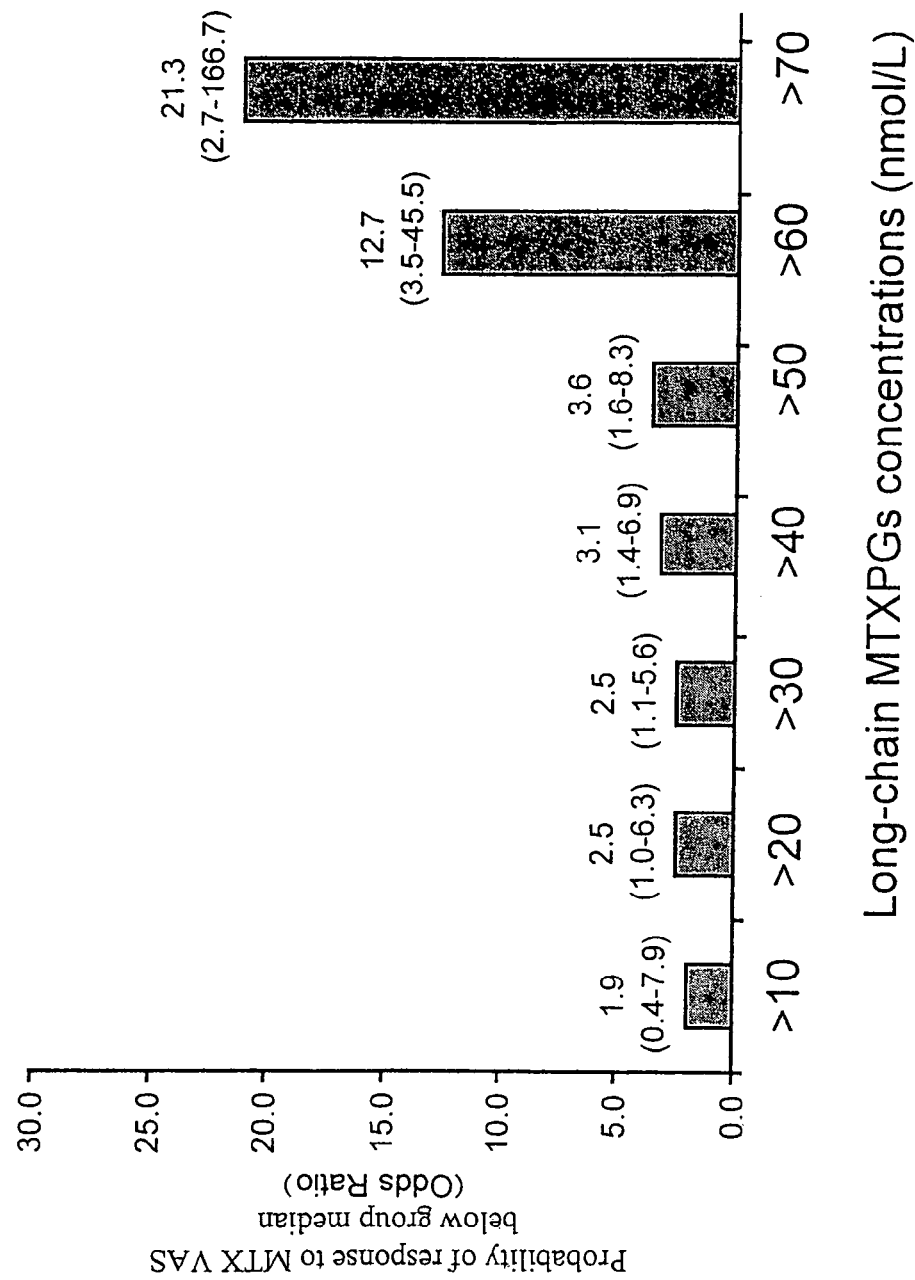

The relationship between increasing levels of MTXPG$_3$ and likelihood of response above median is further illustrated in FIG. 4E. In particular, patients having RBC MTXPG$_3$ levels, which correlated with long-chain MTXPG levels as shown above, above 60 nmol/L were 12.7-fold more likely to have clinical responsiveness to the chemotherapy above average (95% CI; OR: 3.5-4.5; p<0.01). Furthermore, patients having red blood cell long-chain MTXPG levels above 60 nmol/L were 4.4-fold more likely to be within the top 25$^{th}$ percentile of clinical responsiveness to methotrexate (95% CI; OR 1.7-11.7; p<0.01). In contrast, patients having red blood cell long-chain MTXPG levels below 40 nmol/L were 4.1-fold more likely to be within the highest 25$^{th}$ percentile of disease activity (95% CI; OR: 1.6-10.9; p<0.01). These results indicate that a predetermined threshold of long-chain MTXPG levels, calculated, for example, based on MTXPG$_3$ levels, can be useful for predicting clinical responsiveness to methotrexate and other chemotherapies.

Example 2

Genetic Polymorphisms Associated with Superior Clinical Responsiveness to Chemotherapy This example describes the identification of novel associations between genetic polymorphisms in the folate, de novo purine synthesis, and de novo pyrimidine synthesis pathways and clinical responsiveness to chemotherapy.

A. Contribution of the RFC-1 G80A Polymorphism to Clinical Responsiveness to Methotrexate Therapy In the 108 patients, allelic frequency for the RFC-1 80A variant allele was 44%. The distribution of genotypes consisted of 34/108 (31%) patients with the homozygous wild-type genotype (RFC-1 80G/G), 53/108 (49%) heterozygous patients (RFC-1 80G/A) and 21/108 (19%) patients with the homozygous mutant genotype (RFC-1 80A/A). The twenty-one patients carrying the RFC-1 homozygous mutant genotype (RFC-1 80A/A) were compared to the eighty-seven patients carrying the non-homozygous mutant genotype, which was either wild-type or heterozygous (RFC-1 80G/G or 80G/A).

As shown in FIG. 5, increasing red blood cell long-chain methotrexate polyglutamate concentrations were significantly associated with therapeutic response to methotrexate in a logistic regression model that included the RFC-1 G80A genotype (0: non-homozygous mutant; 1: homozygous mutant). Individual carriers of the homozygous mutant RFC-1 genotype tended to have an increased probability of response above the group median and an increased probability for a total number of tender and swollen joints below the median, albeit these associations were not statistically significant (FIGS. 5A and 5C; p>0.05). However, mutant homozygosity for RFC-1 was an additional independent factor for increased disease activity VAS score and mHAQ below the group median (FIG. 5, panels B and D). The data revealed that the contribution of the RFC-1 homozygous mutant genotype to an increased probability of lower disease activity VAS score was evident at low concentrations of MTXPGs, while increasing MTXPG concentrations tended to overcome this contribution (FIG. 5B). In contrast, the overall contribution of the RFC-1 homozygous mutant genotype to an increased probability of mHAQ below the group median did not appear to be affected by increasing RBC methotrexate polyglutamate concentrations (FIG. 5D).

Previous reports have shown that individuals carrying the RFC-1 80A variant allele have a worse outcome during treatment of acute lymphoblastic leukemia compared to those with the RFC-1 G/G genotype (Layerdiere et al., supra, (2002)). Furthermore, individuals carrying the RFC-1 homozygous mutant genotype have been shown to have higher plasma methotrexate concentrations as compared to those with the non-homozygous mutant genotype (Layerdiere et al., supra, (2002)). In the rheumatoid patient population described here, no differences in red blood cell long-chain methotrexate polyglutamate levels were observed between patients carrying the RFC-1 homozygous mutant genotype as compared to those carrying the non-homozygous mutant genotype. These results indicate that individual carriers of the RFC-1 80A/A genotype can have an increased probability of responsiveness to chemotherapeutics such as methotrexate. Thus, in autoimmune diseases such as rheumatoid arthritis, the RFC-1 G80A polymorphism can directly impact disease activity through subtle alteration in folate homeostasis rather than in methotrexate pharmacokinetics (Whetstine et al., supra, (2001); Chango et al., supra, (2000)).

B. Contribution of the ATIC C347G Polymorphism to Clinical Responsiveness to Chemotherapy A mutation in ATIC, which is a fundamental component of the de novo purine synthetic pathway, was analyzed for a correlation with patient responsiveness to methotrexate therapy. The ATIC C347G mutation results in a threonine to serine substitution at position 116 of ATIC (C347G).

In the population of 108 rheumatoid arthritis study patients described above, allelic frequency for the ATIC 347G variant allele was 37%. The frequency of genotypes consisted of 43% patients homozygous wild-type (ATIC 347C/C; n=47), 40% heterozygous patients (ATIC 347C/G; n=43) and 17% patients homozygous for the G mutation (ATIC 347G/G; n=18). Patients carrying the 347G/G homozygous mutant genotype were compared to those carrying either the heterozygous or wild type genotype ("non-homozygous mutant carriers").

ATIC genotype (homozygous mutant versus non-homozygous mutant) was included in a logistic regression model with long-chain methotrexate polyglutamate concentration. As disclosed herein, individual carriers of the homozygous mutant ATIC genotype presented an increased probability of clinical responsiveness above the group median (FIG. 6C) and an increased probability of a total number of tender and swollen joints below the group median (FIG. 6A) compared to those carriers of the non-homozygous mutant genotype. Furthermore, individual carriers of the homozygous mutant genotype tended to present an increased probability of disease activity and a mHAQ below the group median, but the overall contribution was not statistically significant (FIGS. 6B and 6C). The contribution of the polymorphism appeared relevant at low concentrations of methotrexate polyglutamates, while higher levels of methotrexate polyglutamates tended to overcome the beneficial contribution of the polymorphism to therapeutic response (FIG. 6C). The percentage of patients receiving concomitant low dose corticosteroids, generally used to treat patients with refractory disease, was significantly lower in those with the ATIC homozygous mutant 347G/G genotype as compared with those having the ATIC 347C/C or C/G genotypes (22% vs. 51%; p=0.02).

These results indicate that rheumatoid arthritis patients carrying the ATIC homozygous variant allele genotype 347G/G can have a superior clinical responsiveness to chemotherapeutics such as methotrexate as compared to patients having a non-homozygous variant allele genotype; these results are consistent with the anti-inflammatory effect of methotrexate occurring, at least in part, through inhibition of ATIC. The threonine to serine substitution at position 116 of ATIC may affect catalytic activity of the enzyme and, thus, subsequently alter intracellular concentrations of purine precursors. Based on these results, individual carriers of the ATIC homozygous variant allele genotype can present decreased ATIC enzymatic activity and therefore accumulate increased intracellular pools for the purine precursor AICAR, resulting in a selective advantage due to build-up of the anti-inflammatory adenosine though inhibition of adenosine deaminase by AICAR, and a corresponding superior responsiveness to methotrexate and other chemotherapeutics.

C. Contribution of the TS 2TR Polymorphism to Clinical Responsiveness to Chemotherapy A mutation in TS, which is a fundamental component of the de novo pyrimidine synthetic pathway, was analyzed for a correlation with patient responsiveness to methotrexate therapy. TS methylates deoxyuridine monophosphate to produce deoxythymidylate, the unique de novo source of thymidylate in the cell. Inhibition of TS by methotrexate causes cytotoxicity by dTTP pool depletion, leading to thymineless death (Hryniuk, W. M., Cancer Res 35:1085-1092 (1975)). The TS 2TR variant allele contains two 28 base pair tandem repeats (2TR or TSER*2) in the promoter of TS instead of the three tandem repeats (3TR or TSER*3) observed in the wild-type allele.

Figure 8:
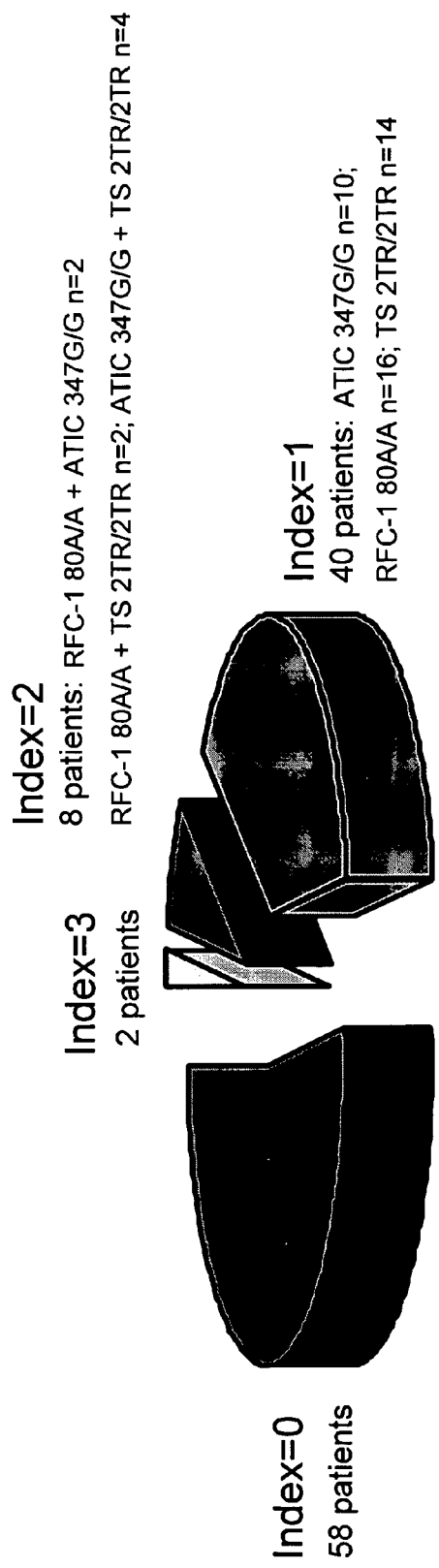
FIG. 8 shows the number of patients with homozygous variant allele genotypes in RFC-1, ATIC, and/or TS, and the corresponding pharmacogenetic index.

As shown in FIG. 8, for the population of 108 rheumatoid arthritis study patients described above, the frequency of genotypes consisted of 14 patients homozygous for TS 2TR, but non-homozygous for ATIC 347G or RFC-1 80A variant alleles; 2 patients homozygous for TS 2TR and RFC-1 80A; 4 patients homozygous for TS 2TR and ATIC 347G; and 2 patients homozygous for all three variant alleles. 58 patients were non-homozygous for all three variant alleles. The contribution of the TS 2TR variant allele to the therapeutic response is described below.

D. Contribution of the Pharmacogenetic Index to Therapeutic Response

The results disclosed herein indicate that common polymorphisms in the folate, de novo purine synthesis, and de novo pyrimidine synthesis pathways can be associated with superior responsiveness to methotrexate and other chemotherapeutics. Given that penetrance of these polymorphisms in patients experiencing clinical responsiveness was relatively low, the sum of variant homozygosities (pharmacogenetic index, or PGENi) was analyzed for its ability to enhance the distinction between superior and inferior responsiveness to the chemotherapy. As shown in FIG. 8, for the 108 patients enrolled, 40/108 patients (37%) were carriers of one homozygous variant allele genotype (RFC 80A/A, ATIC 347G/G, or TS 2TR/2TR; PGENi=1), 8/108 (7%) were carriers of any combination of two homozygous variant allele genotypes (PGENi=2), 2/108 patients (2%) were carriers of all three homozygous variant allele genotypes (PGENi=3), and 58/108 patients (54%) did not carry either of these homozygous variant allele genotypes (PGENi=0).

As shown in FIGS. 7 and 9, the pharmacogenetic index was useful in predicting an increased probability of responsiveness to chemotherapy, a lower number of tender and swollen joints, a lower disease activity, and a lower functional disability in patients with rheumatoid arthritis. In particular, FIG. 7 shows the PGENi for homozygous variant alleles in ATIC and RFC-1 (PGENi values range from 0-2), whereas FIG. 9 shows the PGENi for homozygous variant alleles in ATIC, RFC-1, and TS (PGENi values range from 0-3). Each of the clinical outcome variables was significantly predicted by the model which included both phenotypic and genetic variables.

Figure 10:
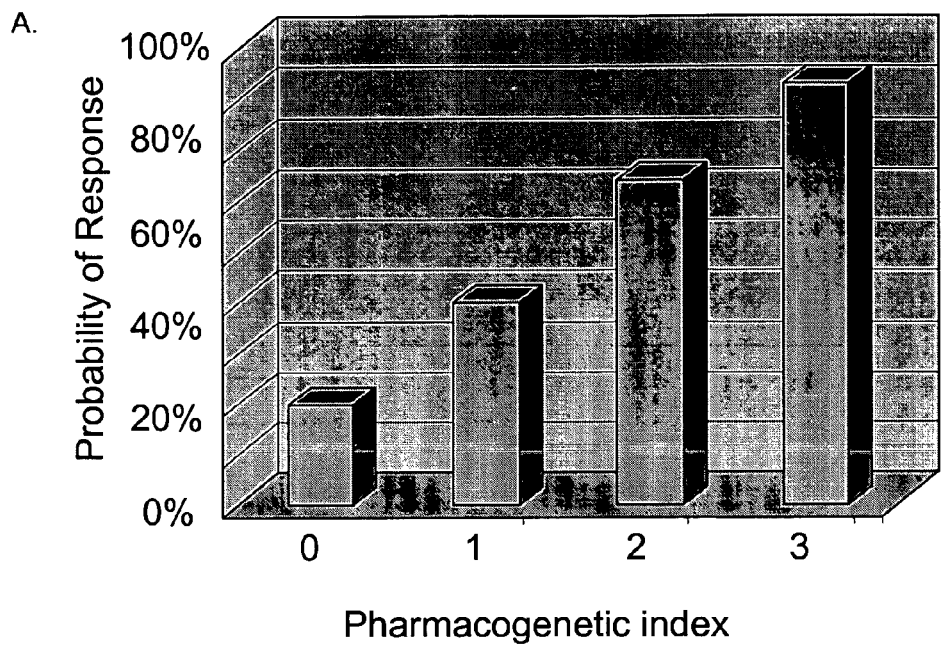
FIG. 10 shows the effect of the PGENi on the probability of response to MTX. Panel A shows that patients with a PGENi greater than 0 have an increased probability of response to MTX. Panel B shows that patients with a PGENi greater than 0 and higher concentrations of MTXPGs have an increased probability of response to MTX.
Figure 10:
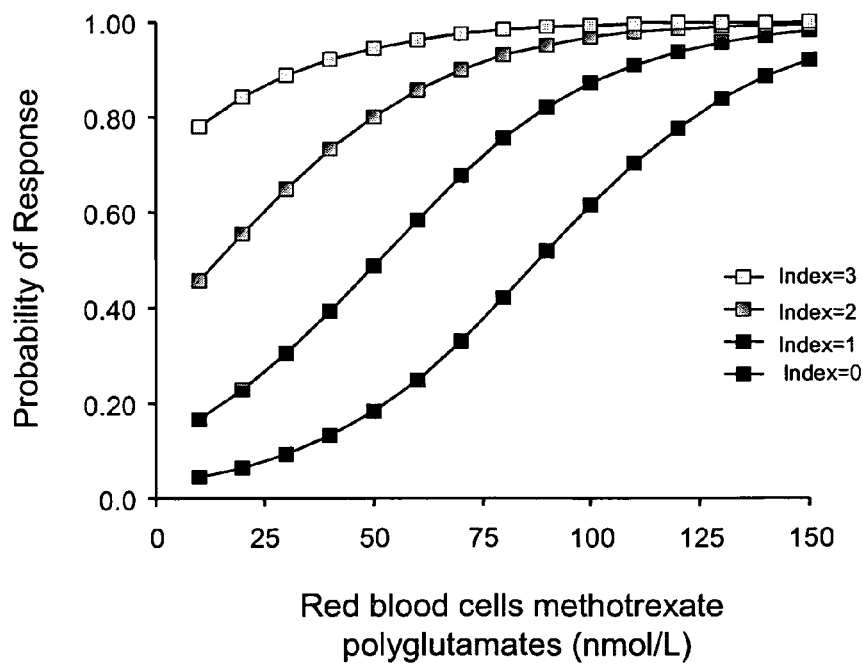
Figure 11:
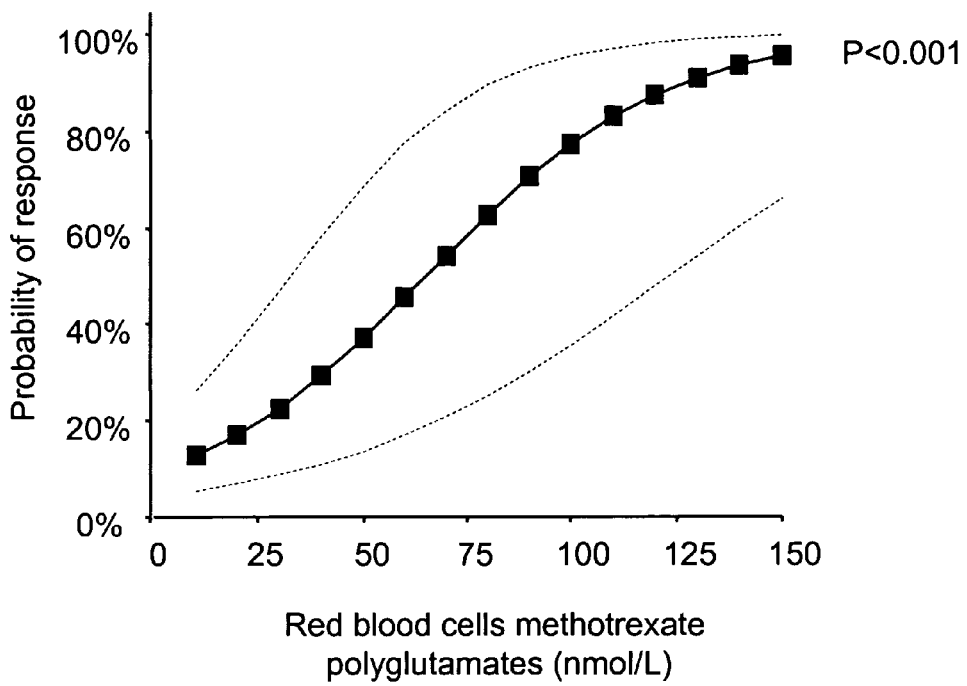
FIG. 11 shows the effect of the RBC MTXPG concentration on the probability of response to MTX. Panel A shows that patients with red blood cell (RBC) MTXPG concentrations above about 60 nmol/L have an increased probability of response to MTX. Panel B shows that patients with MTXPG concentrations above 60 mmol/L have an increased probability of response to MTX for a particular PGENi.
Figure 11:
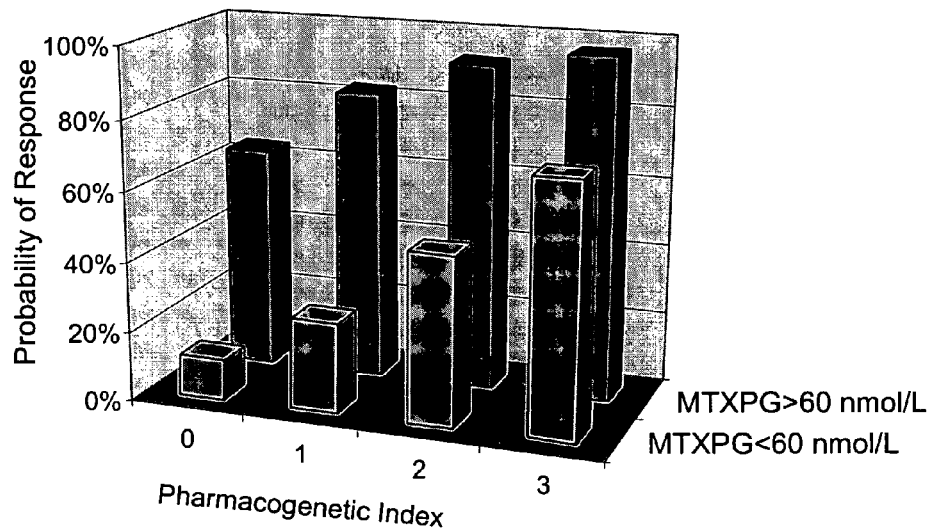

As shown in FIG. 10A, patients with a PGENi between 1-3 are 3.7-fold more likely to have a good response to methotrexate therapy (CI 95%; 1.4-9.1). FIG. 10B shows that as the PGENi value increases (i.e., more homozygous variant allele genotypes), the greater the probability of response to methotrexate therapy at a given RBC MTXPG concentration. Further, as shown in FIG. 11A, patients with RBC MTXPG concentrations above about 60 nmol/L have an increased probability of response to methotrexate therapy. FIG. 11B shows that patients with a PGENi greater than 0 and concentrations of MTXPG above 60 nmol/L have an increased probability of response to methotrexate therapy. As such, while either MTXPG concentration or PGENi alone is an excellent indicator of an individual's response to a chemotherapy, their combined determination provides a superior method for predicting, calculating, and/or optimizing an individual's clinical responsiveness to the chemotherapy.

One skilled in the art understands that the pharmacogenetic index can be applied to patients with autoimmune diseases such as rheumatoid arthritis as well as other patients for individualization of methotrexate and other chemotherapies. As a non-limiting example, identification of individuals with a PGENi of 0 (66% of patients) and who have low methotrexate polyglutamate concentrations ("slow polylgutamators") indicates that it can be beneficial to use a more aggressive methotrexate dose in order to maximize polyglutamation and therapeutic effect. Such patients also can benefit from a more aggressive combination regimen in which, for example, methotrexate is combined with one or more additional disease-modifying anti-rheumatic drugs (DMARDs) such as TNF-α antagonists.

In sum, the results disclosed herein indicate that analysis of methotrexate tri-glutamate level as an indicator of long-chain methotrexate polyglutamate level, combined with determination of a PGENi that includes total variant homozygosity for low penetrance polymorphisms in the folate and de novo purine and pyrimidine synthesis pathways, including specific variant alleles in ATIC, RFC-1, and TS, can be utilized to individualize and optimize chemotherapy.

Example 3

An HPLC System Suitable for Detection of MTXPGs in Samples from Individuals Undergoing Methotrexate Therapy This example describes a chromatographic system, conditions, and reagents suitable for separation of methotrexate polyglutamates (MTXPGs) in cell samples.

A. Preparation of Reagents 4-amino-10-methylpteroylglutamic acid (methotrexate; MTXPG$_1$) was purchased from SIGMA (St. Louis, Mo.). 4-amino-10-methylpteroyldi-glutamic acid (MTXPG$_2$), 4-amino-10-methylpteroyltri-glutamic acid (MTXPG$_3$), 4-amino-10-methylpteroyltetra-glutamic acid (MTXPG$_4$), 4-amino-10-methylpteroylpenta-glutamic acid (MTXPG$_5$; (SEQ ID NO:12)), 4-amino-10-methylpteroylhexa-glutamic acid (MTXPG$_6$; (SEQ ID NO:15)), and 4-amino-10-methylpteroylhepta-glutamic acid (MTXPG$_7$; (SEQ ID NO:14)) were purchased as ammonium salts from Schircks laboratories (Jona, Switzerland). HPLC grade acetonitrile was purchased from Fisher Chemicals (Fair Lawn, N.J.); hydrogen peroxide (30%, v/v), ammonium hydroxide, and glacial acetic acid were obtained from Sigma.

Methotrexate and each of the individual purified methotrexate polyglutamates were dissolved in 0.1 N potassium hydroxide. After dissolution, the concentration of the standards was confirmed using a Hitachi U-2000 spectrophotometer and the UV molar extinction coefficients ($\epsilon$256 nm=23,000). The individual purified methotrexate polyglutamate standards were diluted to a final concentration of 100 µM in water and stored at −70° C., where they were stable for at least 6 months.

B. Chromatographic System and Separation

The liquid chromatograph was an Agilent 1100 HPLC chemstation system composed of a quaternary pump, a system controller, an autoinjector, a sample cooler kept at 4° C., and a fluorometer. Chromatograms were acquired and analyzed on a Hewlett-Packard Vector XA computer. Methotrexate polyglutamates were detected with post-column derivatization using a photochemical reactor unit (Aura Industries, New York, N.Y.) equipped with an elongated 254 nm low pressure mercury ultraviolet lamp and containing a $\frac{1}{16}$" outer diameter TEFLON™ tubing (internal diameter 0.25 mm) assembled as a knitted coil and connected on-line between the analytical column and fluorometer. The knitted coil was extended lengthwise through the photochemical reactor unit; all but a portion of the elongated lamp was masked with foil such that only a segment of the knitted coil was irradiated. In particular, the lamp was masked such that only 1 meter of the coil was irradiated with the lamp, which at a flow rate of 1 ml/min. corresponded to 3 seconds irradiation. Methotrexate polyglutamate photolytic products were measured at an excitation wavelength of 274 nm and an emission wavelength of 464 nm, unless otherwise indicated. The retention times described herein were measured from time of injection to time of detection at the post-reactor unit fluorometer.

HPLC separation was performed on a 25 cm×4.6 mm X Terra MS C18 column (Waters, Milford, Mass.), 5 µm particle size, protected by a guard column. The system also included a C18 pre-column that was changed every 200 injections. Mobile phase A consisted of ammonium acetate (10 mM) at pH 6.50 with hydrogen peroxide (30% v/v) at a final concentration of 0.2%. Mobile phase B consisted of acetonitrile. The samples were eluted at a flow rate of 1 ml/minute, with a 20-minute linear gradient from 2 to 12.5% acetonitrile. After 20 minutes, the mobile phase was returned to 100% mobile phase A and re-equilibrated for 5 minutes. Samples were maintained at 4° C. and injected every 30 minutes with an autoinjector. The analytical column demonstrated no deterioration of its performance after up to 500 injections. Methotrexate polyglutamate photolytic products were analyzed at an excitation wavelength of 274 nm and an emission wavelength of 464 nm. Spectral identification using the excitation spectra of the methotrexate polyglutamate post-column photolytic product in red blood cell extracts was performed by comparison with the excitation spectra of the methotrexate post-column photolytic product in water.

C. Calibration and Preparation of Standard Curves

Calibration and standard curves were performed essentially as follows. Standard curves were prepared by supplementing known amounts of purified MTXPG$_1$, MTXPG$_2$, MTXPG$_3$, MTXPG$_4$, MTXPG$_5$ (SEQ ID NO:12), MTXPG$_6$ (SEQ ID NO:15), and MTXPG$_7$ (SEQ ID NO:14) to a hemolysate prepared from a pool of red blood cells isolated from healthy donors (Blood bank, San Diego, Calif.). These "supplemented" red blood cell standards containing methotrexate polyglutamate concentrations ranging from to 50 nmol/L packed red blood cells. Standard curves were fit by linear regression using peak area versus concentration.

D. Precision, Accuracy, and Recovery

The precision, accuracy, and recovery of the assays were determined as follows. Intra- and inter-day precision and accuracy were determined by analyzing low and high concentrations of methotrexate polyglutamates supplemented at known amounts into red blood cell hemolysates. Intra-day analysis was performed with supplemented replicates, and inter-day evaluation was assessed with 5 replicates on 5 different days. Accuracy was calculated as the percentage error of the measured concentrations from the supplemented samples relative to the target concentration (measured concentration/target concentration×100%). Precision was determined by determining the coefficient of variation. Recoveries for methotrexate polyglutamates were determined by comparing the peak height from supplemented red blood cell samples with those from samples prepared with water at the same concentrations within the validated range.

E. Treatment of Patient Samples

Blood samples (5 ml) were collected from patients receiving low dose methotrexate therapy after written informed consent. Samples were centrifuged for 10 minutes to separate plasma and buffy coat from red blood cells. Red blood cells were washed with two volumes of saline and then stored at −70° C. until analysis.

A 100µl aliquot of RBC hemolysate was briefly homogenized with 150 µl of water in an eppendorf tube before addition of 25 µl 70% perchloric acid to the mixture, vortexing for 10 seconds and centrifuging for minutes. A total volume of 80 µl of red blood cell supernatant was directly injected onto the HPLC system.

Results were expressed as nmol/L packed red blood cells, and patient results were expressed as an average plus or minus the standard error of the mean (±SEM). Spectral identification of methotrexate polyglutamate post-column photolytic product was performed by comparison of the excitation spectra of post-column photolytic product of purified methotrexate in water.

Example 4

Quantification of MTXPG Concentration in Red Blood Cell Extracts by HPLC Fluorometry with Post-Column Derivatization This example describes determination of the intracellular concentration of methotrexate polyglutamates in patients treated with methotrexate therapy.

A. Separation and Detection of MTX and MTXPGs in Cellular Samples

A chromatogram of a standard containing all seven methotrexate polyglutamates at a final concentration of 25 nmol/L each in water is presented in FIG. 16A. The retention times of individual methotrexate polyglutamates on the HPLC system described above were as follows: $MTXPG_7$ (SEQ ID NO:14): 12.5 minutes; $MTXPG_6$ (SEQ ID NO:15): 13.0 minutes; $MTXPG_5$ (SEQ ID NO:12): 13.7 minutes; $MTXPG_4$: 14.5 minutes; $MTXPG_3$: 15.7 minutes; $MTXPG_2$: 17.5 minutes; and $MTXPG_1$: 19.8 minutes. As shown in FIG. 16B in which the excitation spectra of $MTXPG_1$ through $MTXPG_7$ (SEQ ID NO:14) photolytic products are overlaid, the spectra of the different photolytic products are essentially identical. As further shown in FIG. 16B, the $MTXPG_1$ through $MTXPG_7$ (SEQ ID NO:14) photolytic products exhibited a maximum excitation wavelength at 274 nm.

Figure 17:
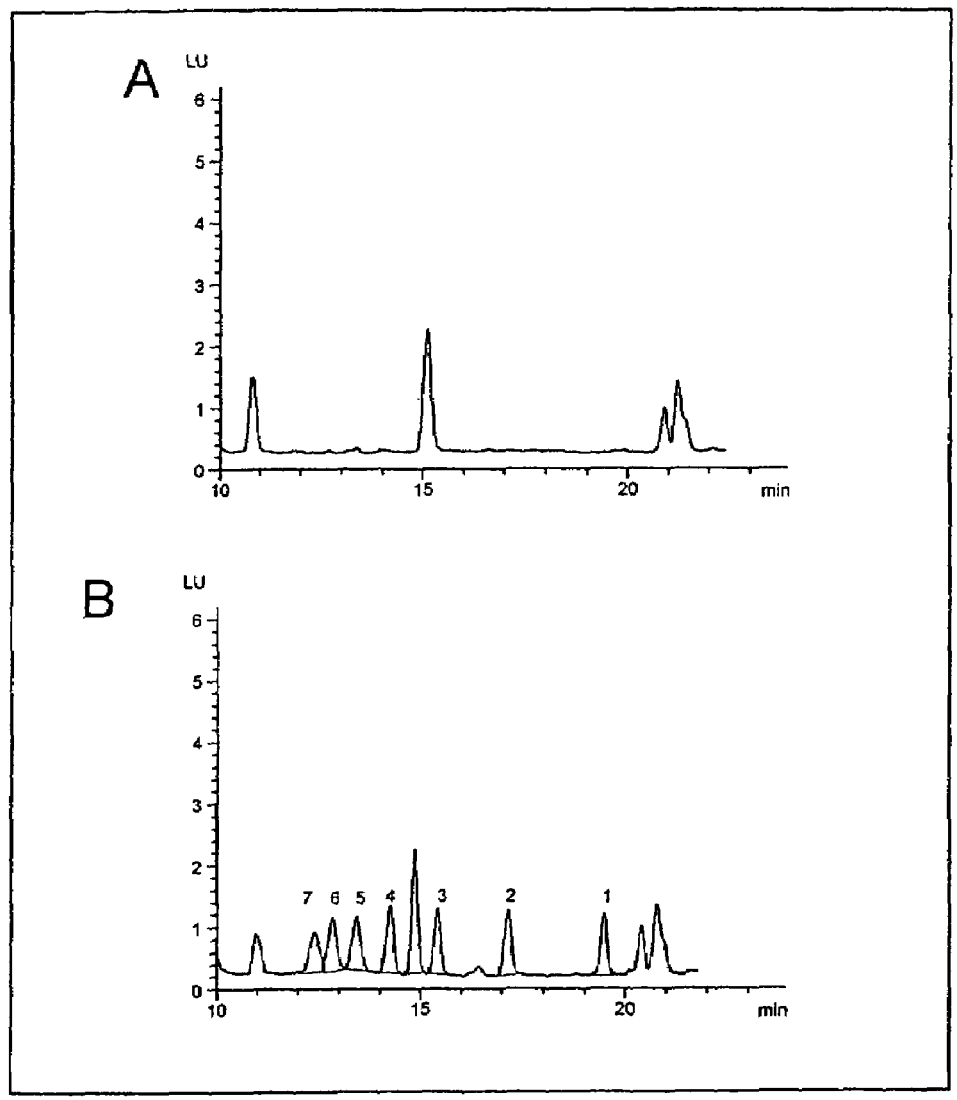
FIG. 17 shows chromatograms of control and supplemented red blood cell samples homogenized and treated with perchloric acid. The excitation wavelength was 274 nm, and the emission wavelength 464 nm. Panel A: Typical chromatogram of control red blood cell sample. Panel B: Typical chromatogram of a red blood cell sample supplemented with purified $MTXPG_1$ to $MTXPG_7$ (SEQ ID NO:14) at a final concentration of 25 nmol/L each. Equations describing the standard curves were: $MTXPG_1$, y=0.493x+0.245; $MTXPG_2$, y=0.540x+0.130; $MTXPG_3$, y=0.561x+0.125; $MTXPG_4$, y=0.568x+0.112; $MTXPG_5$, y=0.668x+0.01; $MTXPG_6$, y=0.710x+0.07; and $MTXPG_7$ (SEQ ID NO:14), y=0.430x+0.316, where y is the peak area and x is the supplemental concentration.

Typical chromatograms of control red blood cell extracts or red blood cell extracts supplemented with known amounts of purified methotrexate polyglutamates are shown in FIG. 17. Control (FIG. 17A) and supplemented (FIG. 17B) hemolysates were homogenized and perchloric acid treated as described above. Standard curves demonstrated a linear relationship between peak area and concentration, with correlation coefficients greater than 0.995 for all seven analytes.

Intra-day and inter-day precision and accuracy of the assay are summarized in Table I. The coefficients of variation for intra-day and inter-day precision were less than 15% at low and high concentrations of analytes. Accuracy ranged from 88 to 112% for the seven MTXPGs. Average extraction recoveries were as follows: 60% $MTXPG_1$; 66% $MTXPG_2$; 65% $MTXPG_3$; 66% $MTXPG_4$; 79% $MTXPG_5$ (SEQ ID NO:12); 80% $MTXPG_6$ (SEQ ID NO:15); and 60% $MTXPG_7$ (SEQ ID NO:14). The limits of detection, defined as three times the signal-to-noise ratio, were 2 nmol/L packed red blood cells. The limit of quantification for all seven methotrexate polyglutamates was 5 nmol/L packed red blood cells.

B. Detection of MTX and MTXPGs in Patient Red Blood Cell Samples

Figure 18:
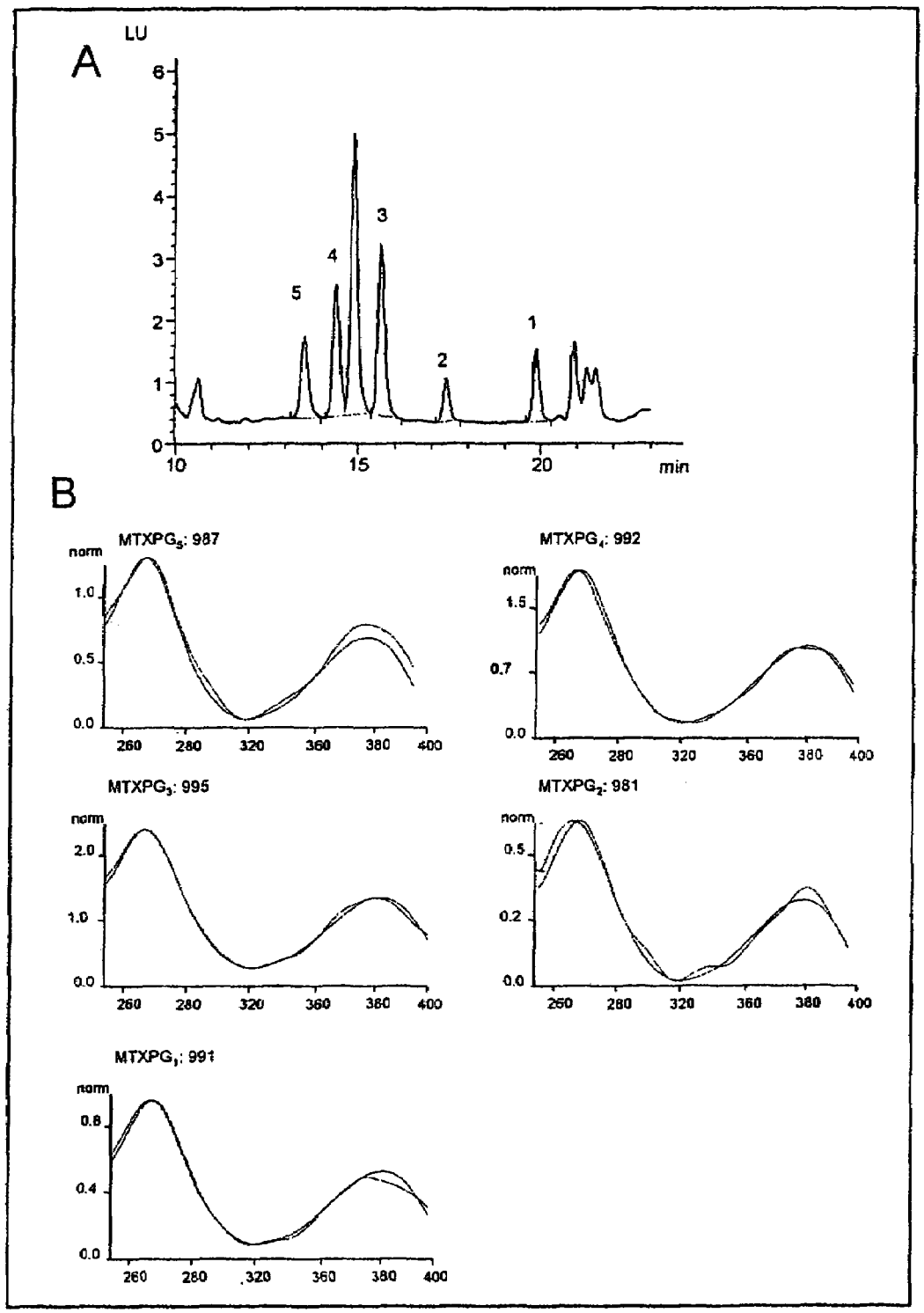
FIG. 18 shows the chromatogram of a red blood cell sample of a patient treated with low-dose methotrexate therapy. Panel A: Chromatogram of a patient on 17.5 mg weekly methotrexate for at least 3 months. Concentrations were as follows: 39 nmol/L $MTXPG_5$ (SEQ ID NO:12); 50 nmol/L $MTXPG_4$; 64 nmol/L $MTXPG_3$; 10 nmol/L $MTXPG_2$; and 27 nmol/L $MTXPG_1$. $MTXPG_6$ (SEQ ID NO:15) and $MTXPG_7$ (SEQ ID NO:14) were undetected in this sample. Panel B: Excitation spectra of each detected methotrexate polyglutamate photolytic product from the patient sample in A compared to the excitation spectra of the methotrexate photolytic product in water. The matching value was greater than 900 for each of the five spectral comparisons.

Red blood cell samples were obtained from 14 patients with polyarthritis receiving low dose weekly methotrexate for at least three months. The weekly doses of methotrexate ranged from 10.0 to 25.0 mg with a median dose of 16.2 mg per week. FIG. 18A shows a typical patient chromatogram for a patient receiving 17.5 mg/week methotrexate. FIG. 18B shows that the excitation spectra of methotrexate polyglutamate photolytic products resolved from the patient sample was very similar to the spectra of the photolytic product of methotrexate in water.

Figure 19:
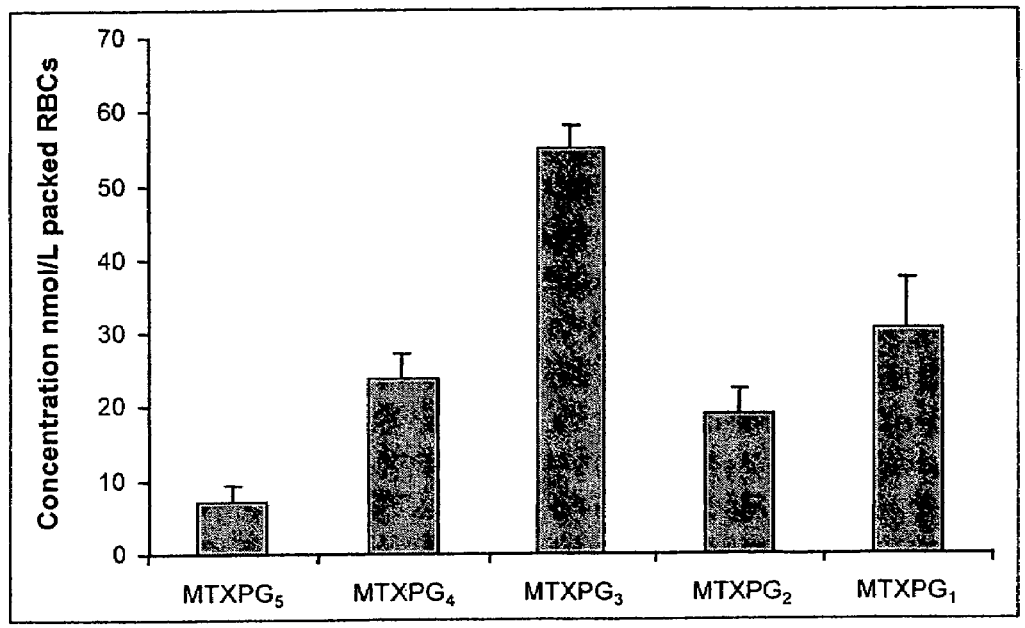
FIG. 19 shows average individual $MTXPG_1$ to $MTXPG_5$ (SEQ ID NO:12) concentrations in 14 patients with rheumatoid arthritis. $MTXPG_6$ (SEQ ID NO:15) and $MTXPG_7$ (SEQ ID NO:14) were undetected.

In the 14 patients receiving 10.0 to 25.0 mg/week methotrexate, the total methotrexate polyglutamate concentration ranged from 69 to 221 nmol/L RBC, with a median of 135 nmol/L RBC (FIG. 19). $MTXPG_6$ (SEQ ID NO:15) and $MTXPG_7$ (SEQ ID NO:14) were undetected (<5 nmol/L) in all 14 patient samples, while $MTXPG_5$ (SEQ ID NO:12) was detected in 8 of 14 patient samples. The total average long chain polyglutamate concentration ($MTXPG_4$+$MTXPG_5$ (SEQ ID NO:12)) was 31±5.7 nmol/L and represented an average of 23% of total methotrexate polyglutamates. $MTXPG_3$ was the principal methotrexate polyglutamate detected in the patient samples, representing an average of 55% of total methotrexate polyglutamates.

Example 5

Contribution of RBC MTXPGs and Polymorphisms in RFC-1, ATIC, and TS to the Effects of MTX This example illustrates that RBC MTXPGs and common polymorphisms in RFC-1, ATIC, and TS are associated with methotrexate effects in rheumatoid arthritis.

A. Methods

1. Study Design

The study was cross-sectional at a single investigational site, a community based rheumatology clinic (Knoxville, Tenn.). To be eligible, patients ($\geq$18 yrs.) had to meet the revised criteria of the American Rheumatism Association for Rheumatoid Arthritis and to have received low-dose MTX therapy for at least three months. Other medications for rheumatoid arthritis included low-dose corticosteroids (<10 mg day), and folic acid supplementation (1 mg/day) to prevent MTX's induced side effects. The Institutional Review Board approved the study and patient consent was obtained.

Patient clinical and demographic characteristics were collected at the time of the enrollment in the study. Patient clinical assessments included a tender joint count (maximum 22), a swollen joint count (maximum 22), a Physician's Global Assessment of Disease Activity (10 cm visual analog scale), a Patient's Global Assessment of Disease Activity (10 cm visual analog scale) and a Patient's Assessment of Physical Function using the modified-Health Assessment Questionnaire (mHAQ). The mHAQ score was calculated using the average score on 8 questions addressed to the patient (1: Dress yourself, 2: Get in and out of bed, 3: Lift a full glass to your mouth, 4: Walk, 5: Wash and dry entire body, 6: Bend down and pick up clothing, 7: Turn faucets on and off, 8: Get in and out of a car). Scoring of items within each was from 0 (without any difficulty) to 3 (unable to do). In addition, a Physician's Assessment of Patient's Response to MTX using a 10 cm visual analogue scale was used. The Physician's Assessment of Patient's Response to MTX was scored from 0 (high response) to 10 (poor response). Clinical data were collected on case report forms at the time of a single study visit. The attending physician and each patient were blinded to MTXPGs concentrations and genotypes throughout the entire study.

2. HPLC Quantification of Red Blood Cells MTXPGs Concentrations

Red blood cell long-chain MTXPG concentrations were measured as described previously using an HPLC-fluorometry procedure with post-column photo-oxidation technique (Dervieux, Clin Chem. (2003)). The technologist performing the quantification of RBC MTXPGs (up to the penta-order of glutamation) was blinded to patient's information.

MTX tri-glutamate ($MTXPG_3$) is the predominant polyglutamate species in RBCs From patients with rheumatoid arthritis and is strongly predictive of the total long-chain MTXPGs concentrations expressed as the sum of $MTXPG_3$+$MTXPG_4$+$MTXPG_5$ (SEQ ID NO:12) ($R^2$=0.94; n=108). Therefore, RBC $MTXPG_3$ concentration was used as the marker of long-chain MTXPGs concentrations ($MTXPG_{3-5}$; (SEQ ID NO:13)). The quantification limit of the analytical method is 5 nmol/L and the detection limit is 2 nmol/L packed RBC (for all MTXPG species) (Dervieux, Clin Chem. (2003)).

3. Genotyping Procedures

Whole blood (EDTA) was drawn the day of each patient's clinical visit and genomic DNA was extracted using a Generation Purification Capture Column (Gentra Systems, Inc; Minneapolis, Minn.) as per manufacturer instructions. Total genomic DNA was quantified using a Hitachi U-2000 spectrophotometer at 260 nm.

The RFC-1 G80A polymorphism (resulting in a histidine to arginine substitution at codon 27 of RFC-1) was detected using a PCR-RFLP method as previously described (Chango et al., *Mol Genet Metab* 70:310-315 (2000)). PCR amplification was performed with 5 ng genomic DNA in a final volume of 50 µl containing 900 nM forward primer (5'-AGT GTC ACC TTC GTC CCC TC-3'; SEQ ID NO:7), 900 nM reverse primer (5'-CTC CCG CGT GAA GTT CTT; SEQ ID NO:8), and with 1×AmpliTaqGold master mix (Applied Biosystem, Forster city, CA). The PCR conditions consisted of a 5-minute initial denaturation at 95° C. followed by 35 cycles with denaturation for 15 seconds at 95° C., annealing/extension at 60° C. for 1 minute, with a final extension at 72° C. for 7 minutes. A 20 µl PCR product (amplicon of 230 bp) was subjected to enzymatic digestion at 37° C. using CfoI (Promega, Madison Wis.) for 3 hours. Following a 3% agarose gel electrophoresis in presence of ethidium bromide, individuals with the 80GG genotype presented three fragments (125, 68, and 37 bp) whereas individuals with the 80AA genotype presented two fragments (162 and 68 bp).

The ATIC C347G polymorphism (resulting in a threonine to serine substitution at position 116 of ATIC) was determined using a real-time TaqMan allelic discrimination method using fluorogenic 3'-minor groove binding probes. The forward primer sequence was 5'-CCT GCA ATC TCT ATC CCT TTG TAA A-3' (SEQ ID NO:3) and the reverse primer was 5'-TTC TGA CTT ACC AAT GTC AAT TTG CT-3' (SEQ ID NO:4). The allelic discrimination was performed using the 347C fluorescent 5'-FAM-CCA GGT GTA AGT GTT G-MGB-3' (SEQ ID NO:5) and the 347G fluorescent 5'-VIC-TCC AGG TGT AAC TGT T-MGB-3' probes (SEQ ID NO:6). The final conditions were 900 nM of each primer, 200 nM of each probe, with 5 ng genomic DNA in a 1×TaqMan master mix (Applied Biosystem, Forster city, CA). PCR conditions consisted of one 2-minute cycle at 50° C. followed by a 10-minute cycle at 95° C. followed by 40 cycles of 95° C. for 15 seconds, 58° C. for 15 seconds, and finally 60° C. for 45 seconds.

The 28 bp variable number of tandem repeats (TSER*2/*3) in the 5'-UTR promoter region of TS was measured using modifications of the method developed by Horie (Horie et al., *Cell Struct Funct* 20:191-197 (1995)). A 5 ng genomic DNA was amplified in final conditions consisting of 900 nM forward primer (5'-GTG GCT CCT GCG TTT CCC CC-3'; SEQ ID NO:9), 900 nM reverse primer (5'-CCA AGC TTC GCT CCG AGC CGG CCA CAG GCA TGG CGC GG-3'; SEQ ID NO:10), 1.5 mM Magnesium Sulfate (Invitrogen, Carlsbad, Calif.), 1×PCR amplification buffer (Invitrogen, Carlsbad, Calif.), 0.5×PCR enhancer (Invitrogen, Carlsbad, Calif.), and 2.5 U Platinum Taq (Invitrogen, Carlsbad, Calif.). The PCR conditions consisted of a two-minute initial denaturation at 95° C. followed by 35 cycles with a 30 second denaturation at 95° C. followed by 60° C. annealing for 30 seconds, 68° C. extension for 1 minute, and finally a 72° C. final extension for 7 minutes. PCR products were run on 3% agarose. Two 28 bp tandem repeats (TSER*2) consisted of a 220 bp amplicon whereas three 28 bp tandem repeats (TSER*3) consisted of 248 bp amplicon.

4. Statistical Analyses

Because the integrity of the folate/purine/pyrimidine pathways are critical for cell survival, mutations that produces only subtle alterations in a key enzymatic step may be transmitted across generations (common polymorphism) but are likely to exhibit low phenotypic manifestations (low penetrance). Therefore, a pharmacogenetic index was calculated as the sum of the number of ATIC 347G alleles (0: ATIC 347C/C, 1: ATIC 347C/G; 2: ATIC 347G/G), plus the number of TSER*2 alleles (0: TSER*3/*3; 1: TSER*2/*3; 2: TSER*2/*2), plus the presence of the RFC-1 80A/A genotype (0: RFC-1 G/A or G/G; 1: RFC-1 80 A/A, because no difference was found between carriers of the 80A variant versus those carriers of the 80G variant).

Multivariate linear regression analysis with clinical outcome variables as dependant variables was performed with MTXPG concentrations and genetic data (individual component or index) as independent variables. Results were adjusted for concomitant use of corticosteroids or folic acid. Using the Physician's Assessment of Patient's Response to MTX, the population of patients was dichotomized into those responders to methotrexate (VAS≦2 cm) and those non-responders to MTX (VAS>2 cm). Responders were compared to non-responders using a multivariate logistic regression analysis adjusting for corticosteroids and folic acid. The probability of the event (being a responder) was derived from the logistic regression model. Results are expressed as mean±SEM, odds ratio (OR) and probability (P) are given with a 95% confidence interval (CI). Chi-square tests were used as appropriate.

B. Results

A total of 108 patients (76 females and 32 males) aged 65 years (range: 36-90) who were undergoing MTX therapy for more than 3 months (median: 65 range 3-266) were enrolled from December 2002 to May 2003 at the Rheumatology Practice, Knoxville, Tenn. Ninety one patients (84%) received folic acid supplementation (1 mg/day), and 53 patients (49%) were on concomitant low-dose corticosteroids. Demographic data are presented in Table 2.

TABLE 2

Clinical and Laboratory Characteristics of the 108 patients enrolled in the study.

|  | N | Mean ± SEM |
|---|---|---|
| Number of Tender joints (maximum 22) | 108 | 5.0 ± 0.6 |
| Number of Swollen joints (maximum 22) | 108 | 4.0 ± 0.5 |
| Physician assessment of disease activity VAS | 108 | 3.5 ± 0.2 |
| Patient assessment of disease activity VAS | 108 | 4.1 ± 0.2 |
| Physician assessment of response to Methotrexate VAS | 108 | 2.7 ± 0.2 |
| Modified Health assessment questionnaire | 108 | 0.55 ± 0.05 |

1. MTX Dose is Poorly Associated with MTX's Effects

The median weekly MTX dose administered was 14 mg (range 5-25 mg). In a multivariate linear regression including administration of folic acid and corticosteroids, MTX dose was not associated with the number of tender joints (p=0.15), the number of swollen joints (p=0.82), the Physician's Assessment of Patient's Response to MTX (p=0.82), the mHAQ (p=0.09) and ESR($R^2$=0.052; p=0.16). However, higher MTX doses tended to be associated with lower Physicians' Global Assessment of Disease Activity and with lower Patient's Global Assessment of Disease Activity. Results are presented in Table 3.

TABLE 3

Multivariate analysis of outcome variables with methotrexate dose adjusting for concomitant administration of corticosteroids and folic acid.

|  | Global $R^2$ | Methotrexate dose (mg/week) Estimate ± SEM (p level) |
|---|---|---|
| Number of Tender joints | 0.021 | −0.17 ± 0.12; p = 0.15 |
| Number of Swollen joints | 0.003 | −0.22 ± 0.10; p = 0.82 |
| Physician assessment of disease activity VAS | 0.038 | −0.088 ± 0.044; p = 0.06 |
| Patient assessment of disease activity VAS | 0.052 | −0.083 ± 0.065; p = 0.002 |
| Physician assessment of response to Methotrexate VAS | 0.005 | −0.014 ± 0.004; p = 0.71 |
| Modified Health assessment questionnaire | 0.035 | −0.017 ± 0.009; p = 0.09 |

2. Contribution of RFC-1 G80A, ATIC C347G, and TSER*2/*3 Polymorphisms and of RBC MTXPGs to the Effects of MTX The median RBC long-chain MTXPGs concentration (MTXPG$_3$) was 40 nmol/L (range: <5-131 nmol/L). In the 108 patients, the allelic frequency for the RFC-1 80A variant was 44%. The distribution of genotype consisted of 87 patient carriers of the non-homozygous variant genotype (RFC-1 80G/G: n=34; RFC-1 80G/A: n=53) and 21 patient carriers of the homozygous variant genotype (RFC-1 80A/A). The allelic frequency for the ATIC 347G variant was 37%. The distribution of genotypes consisted of 47 patient carriers of the ATIC 347C/C genotype, 43 patient carriers of the ATIC 347C/G genotype and 18 patient carriers of the ATIC 347G/G genotype. The distribution of the TSER*2/*3 tandem repeat polymorphism consisted of 19 patient carriers of the TSER*3/*3 genotype, 66 patients carriers of the TSER*2/*3 genotype and 23 patient carriers of the TSER*2/*2 genotype.

In a multivariate regression analysis, the data revealed that MTXPGs levels and genetic polymorphisms in the folate/purine/pyrimidine pathways contributed significantly to the effects of MTX (Table 4).

Figure 12:
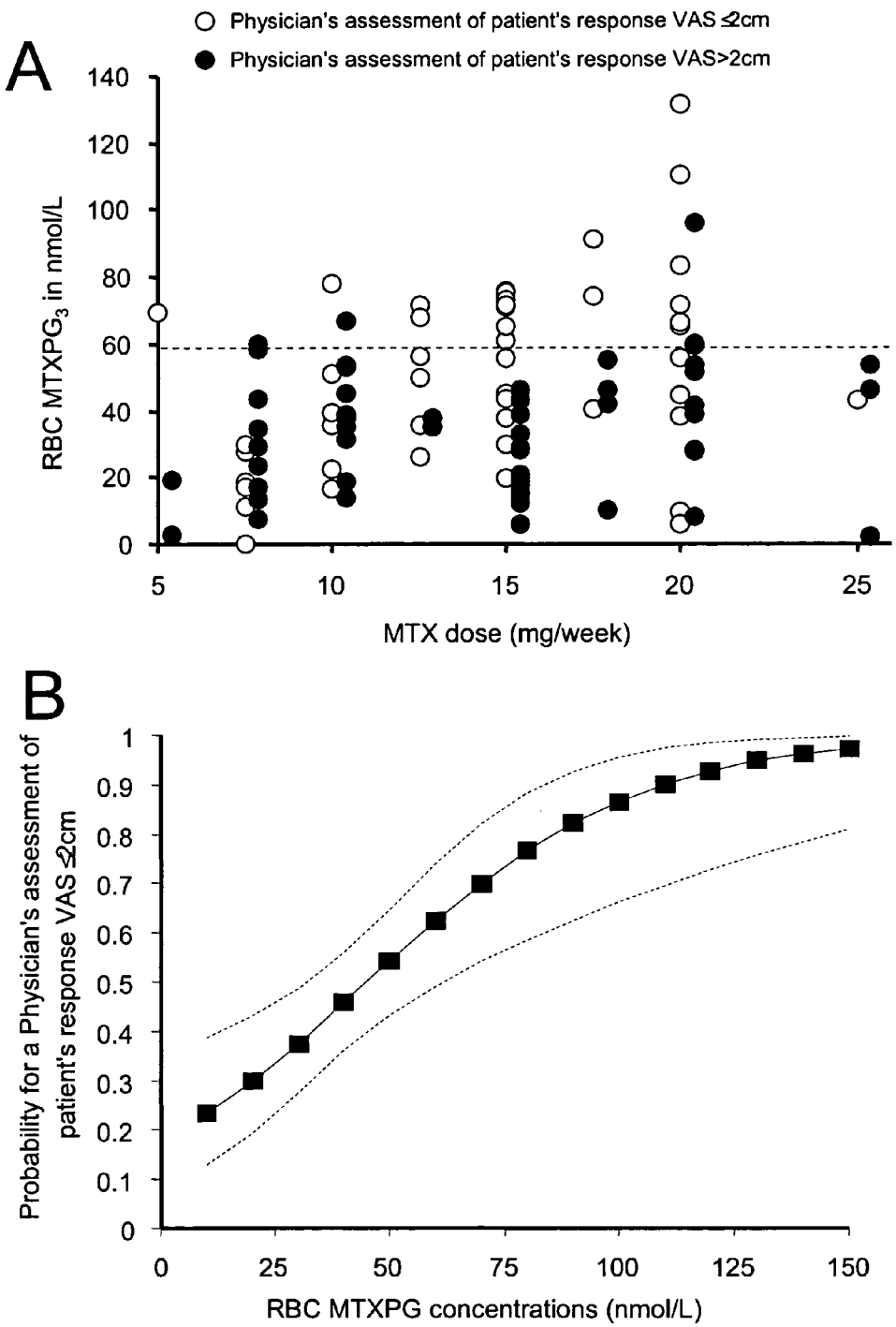
FIG. 12 shows the effects of RBC MTXPG levels on therapeutic response. Panel A: Increased MTX dose is associated with increased MTXPG concentrations. Patients with a physician's assessment of patient's response to MTX VAS≦2 cm (responders: 51 patients) were compared to those with a physician's assessment of patient's response to MTX VAS>2 cm (non-responders: 57 patients). MTXPG concentrations above 60 nmol/L were associated with a 14.0-fold (OR CI 95%: 3.6-53.8; p<0.001) higher likelihood for a good response to MTX. Panel B: Probability P (derived from the logistic regression) for physician's assessment of patient's response to MTX VAS≦2 cm. $MTXPG_3$ estimates: 0.035±0.01 (p<0.001). Increased MTXPG levels are associated with increased probability for a physician's assessment of patient's response to MTX VAS≦2 cm (response). The model predicted accurately 40/57 (70%) of individuals with physician's assessment of patient's response to MTX VAS>2 cm (poor responders) and 32/51 (62%) of patients with a physician's assessment of patient's response to MTX VAS≦2 cm (responders).

Increased concentrations of RBC MTXPG levels were associated with decreased number of tender joints (p=0.048), decreased number of swollen joints (p=0.052), decreased Physician's Global assessment of disease activity VAS (p=0.003) and decreased Physician's assessment of Patient's response to MTX VAS (p=0.0004). In contrast, the Patient's Global assessment of disease activity VAS and the Modified Health assessment questionnaire were not associated by RBC MTXPG levels (p>0.2). Higher MTX doses were associated with higher MTXPGs concentrations ($R^2$=0.078; p=0.003) and MTXPGs concentrations above 60 nmol/L were associated with a 14.0 (OR CI 95%: 3.6-53.8; p<0.001) higher likelihood for a Physician's Assessment of patient's Response to MTX VAS≦2 cm (p=0.001) (FIG. 12).

The RFC-1 80A/A genotype was associated with lower number of swollen joints (p=0.016), lower Patient and Physician's Assessment of Disease Activity VAS (p<0.05) and lower Modified Health assessment questionnaire (p=0.025). In addition, patients carriers of the RFC-1 80A/A genotype presented a higher frequency of RBC MTXPG levels above 60 nmol/L compared to those with those carrier of the 80G allele (38% versus 18%; p=0.051) but there was no difference in MTX dose between the two groups of patients (14.4±1.0 vs 14.1±0.5; p=0.95). Increased number of ATIC 347G alleles appeared associated with decreased number of tender joints (p=0.042), decreased number of swollen joints (p=0.018), decreased physician's assessment of disease activity (p=0.055) and also with decreased physician's assessment of patient's response to MTX (p=0.019). Furthermore, increased number of TSER*2 alleles appeared associated with lower number of tender joints (p=0.094), decreased physician's global assessment of disease activity (p=0.055) and decreased Modified Health assessment questionnaire (p=0.025).

3. Pharmacogenetic Marker and MTX Effects

Figure 13:
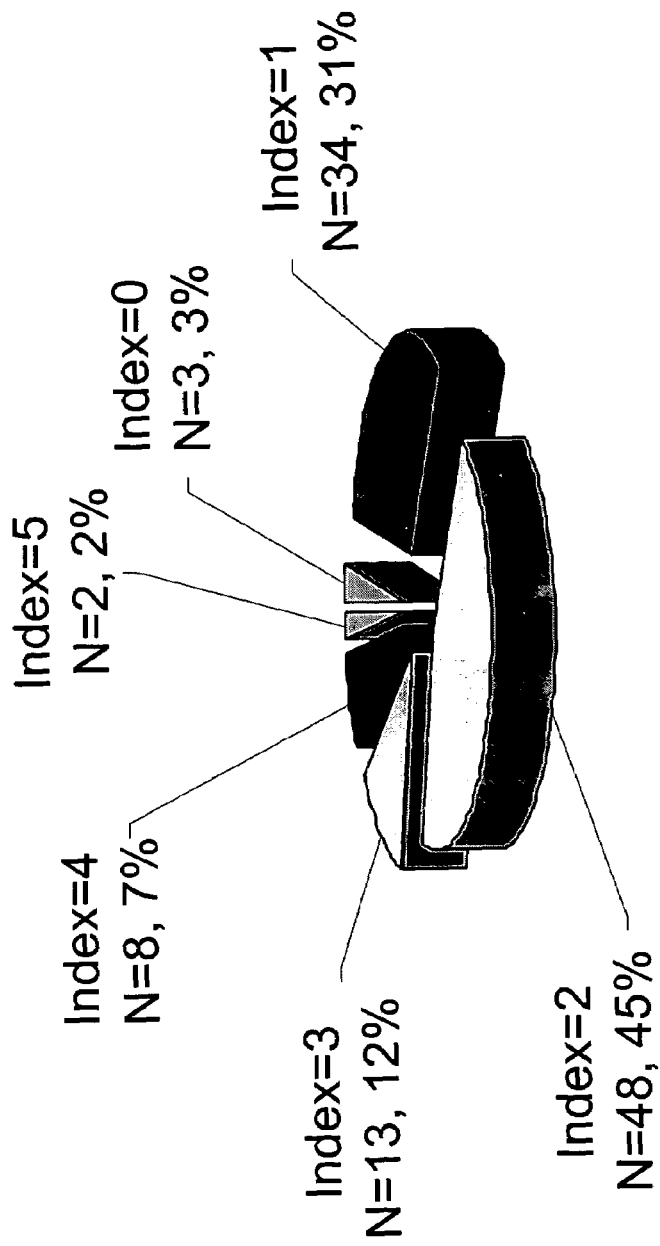
FIG. 13 shows the pharmacogenetic index (PGENi) in the population of 108 patients, where the PGENi is the sum of the number of variant alleles in RFC-1, ATIC, and TS. The PGENi ranged from 0 to 5 because a patient with one or two variant alleles in RFC-1 was counted as 0 or 1, respectively. The number and percentage of patients for each pharmacogenetic index is given.

We calculated the pharmacogenetic index as the total number of ATIC 347G alleles plus total number of TSER*2 alleles plus presence of the RFC-1 80A/A homozygous variant genotype. The index ranged from 0 to 5.0 (FIG. 13). Increased pharmacogenetic index was associated with decreased num-

TABLE 4

Multivariate analysis of outcome variables with RBC MTXPG concentrations, RFC-1 80A/A genotype, number of ATIC 347G alleles and number of TSER*2 alleles adjusting for concomitant administration of corticosteroids and folic acid.

Figure 14:
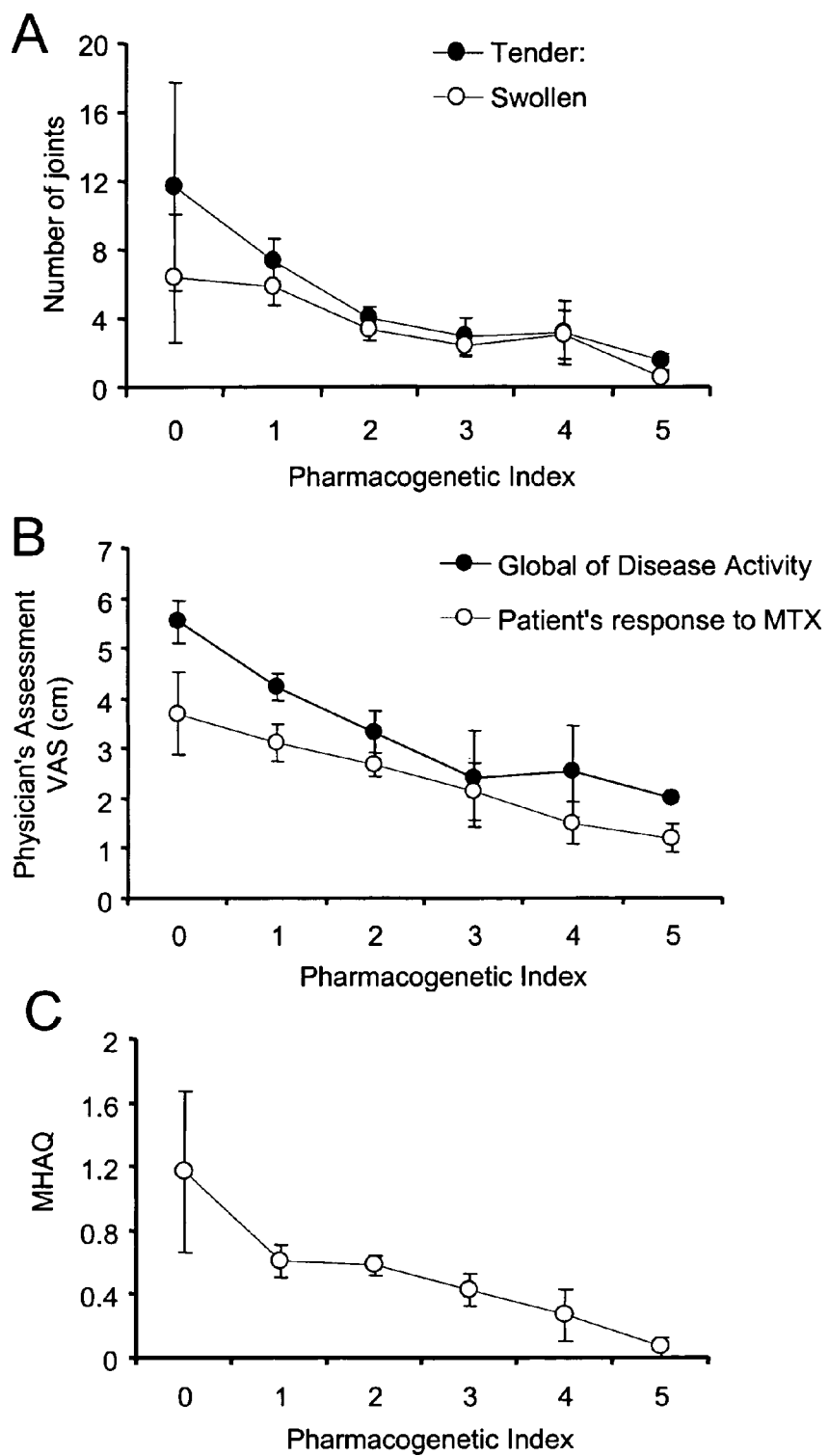
FIG. 14 shows the effect of the PGENi on various clinical parameters, where the PGENi takes into consideration heterozygosity for the variant alleles of RFC-1, ATIC, and TS. Panel A: Increased PGENi is associated with a lower number of tender joints ($R^2$=0.133; Estimate: −1.82±0.55; p=0.001) and a lower number of swollen joints ($R^2$=0.112; Estimate: −1.26±0.48; p=0.008). Panel B: Increased PGENi is associated with lower physician's assessment of disease activity VAS ($R^2$=0.193; Estimate −0.72±0.20; p=0.0004) and lower physician assessment of patient's response to MTX VAS ($R^2$=0.187; Estimate −0.50±0.17; p=0.004). Panel C: Increased PGENi is associated with lower modified Health Assessment Questionnaire (mHAQ) scores ($R^2$=0.095; Estimate −0.14±0.05; p=0.004).
Figure 15:
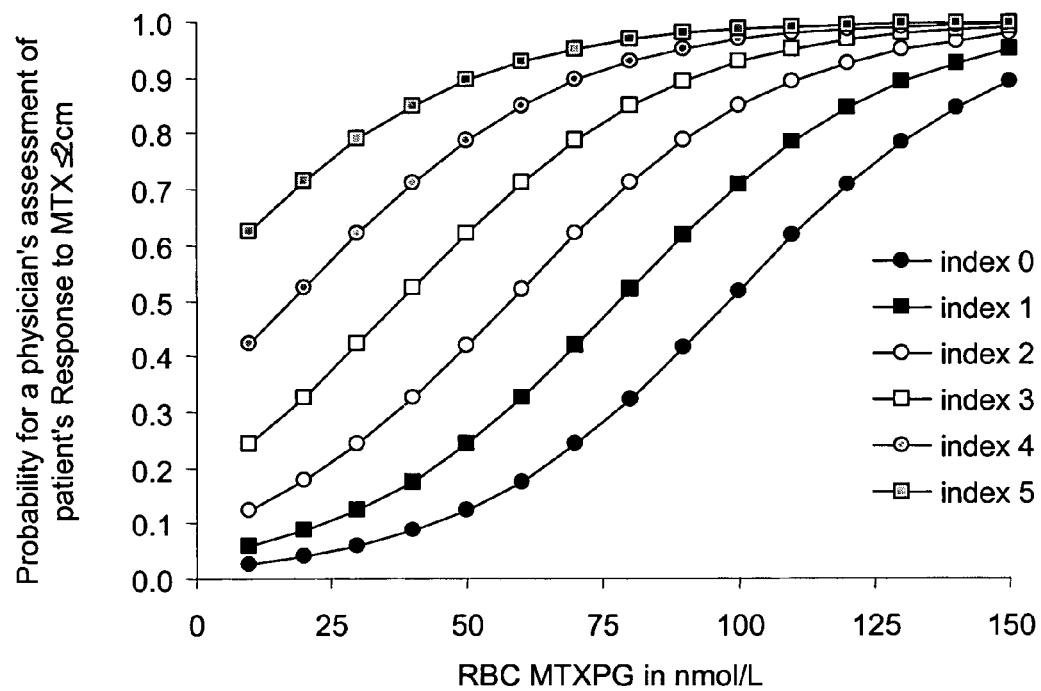
FIG. 15 shows the effect of the PGENi and MTXPGs on the response to methotrexate, where the PGENi takes into consideration heterozygosity for the variant alleles of RFC-1, ATIC, and TS. Probability for a physician's assessment of patient's response to MTX VAS≦2 cm at increasing concentrations of MTXPGs and for a PGENi ranging from 0 to 5 is shown. Patients with a PGENi greater than 0 and higher concentrations of MTXPGs have an increased probability of response to MTX. The model predicted accurately 42/57 (73%) of individuals with physician's assessment of patient's response to MTX VAS>2 cm (poor responders) and 35/51 (68%) of patients with a Physician's Assessment of Patient's Response to MTX VAS≦2 cm (responders).

|  | $R^2$ | RBC MTXPG$_3$ (nmol/L). Estimate ± SEM | RFC-1 80A/A homozygosity Estimate ± SEM | ATIC C347G Nb of 347G Estimate ± SEM | TSER *2/*2 Nb of TSER*2 Estimate ± SEM |
|---|---|---|---|---|---|
| Number of Tender joints | 0.119 | −0.047 ± 0.23 p = 0.048 | −2.35 ± 1.43 p = 0.103 | −1.60 ± 0.78 p = 0.043 | −1.51 ± 0.89 p = 0.094 |
| Number of Swollen joints | 0.146 | −0.035 ± 0.019 p = 0.052 | −2.94 ± 1.20 p = 0.016 | −1.58 ± 0.66 p = 0.018 | 0.06 ± 0.75 p = 0.931 |
| Physician's Global assessment of disease activity VAS | 0.208 | −0.025 ± 0.008 p = 0.003 | −1.50 ± 0.50 p = 0.003 | −0.53 ± 0.27 p = 0.055 | −0.60 ± 0.31 p = 0.055 |
| Patient's Global assessment of disease activity VAS | 0.063 | −0.004 ± 0.009 p = 0.623 | −1.16 ± 0.56 p = 0.040 | −0.09 ± 0.30 p = 0.767 | −0.55 ± 0.35 p = 0.115 |
| Physician's assessment of Patient's response to MTX VAS | 0.182 | −0.026 ± 0.007 p = 0.0004 | −0.34 ± 0.43 p = 0.435 | −0.56 ± 0.24 p = 0.019 | −0.41 ± 0.27 p = 0.131 |
| Modified Health assessment questionnaire | 0.113 | −0.002 ± 0.002 p = 0.214 | −0.27 ± 0.12 p = 0.025 | −0.07 ± 0.07 p = 0.264 | −0.17 ± 0.007 p = 0.026 | ber of tender joints (p=0.001), decreased number swollen joints (p=0.008), decreased Physician's Global Assessment of Disease Activity (p=0.0004), decreased Physician's Assessment of Patient's Response to MTX (p=0.004), and decreased Modified Health assessment questionnaire (p=0.004) (FIG. 14). Those having a pharmacogenetic index above 2 were 4.7 (OR C195% 1.1-7.2) more likely to have Physician's Assessment of Patient's Response to Methotrexate VAS≦2 cm (p<0.0001). In addition, as presented in FIG. 15, increased MTXPG concentrations tended to overcome the contribution of the genetic component on the therapeutic response.

C. Discussion

This is the first study to describe the contribution of MTXPGs and common polymorphisms in RFC-1, ATIC, and TS to the effects of MTX in patients with rheumatoid arthritis treated with low-dose MTX therapy.

Recent study indicates that MTX dosage is suboptimal in rheumatoid arthritis and that innovative approaches are required to more rapidly maximize effects (Ortendahl et al., *J. Rheumatol.* 29:2084-2091 (2002)). Because several investigators have advocated MTX therapeutic drug monitoring with measurement of MTXPGs in various diseases including rheumatoid arthritis (Angelis-Stoforidis et al., *Clin. Exp. Rheumatol.* 17:313-320 (1999); Kremer et al., *Arthritis Rheum.* 29:832-835 (1986); Chladek et al., *Eur. J. Clin. Pharmacol.* 53:437-444 (1998); Masson et al., *J. Clin. Invest.* 97:73-80 (1996); Schmiegelow et al., *J. Clin. Oncol.* 13:345-351 (1995)), RBC MTXPG levels in a large population of patients with rheumatoid arthritis under MTX was prospectively measured for more than three months. Because circulating erythrocytes lack folylpolyglutamate synthetase, MTXPGs in RBCs are representative of polyglutamation in bone marrow progenitors (Schroder et al., *Cancer Chemother. Pharmacol.* 21:145-149 (1988); da Costa et al., *Cancer* 48:2427-2432 (1981)), and therefore are representative of MTXPG levels in less accessible tissues such as lymphocytes. The data revealed that increased RBC MTXPG concentrations were associated with increased effects to MTX, and identified a therapeutic threshold of 60 nmol/L RBC MTXPGs associated with a 14-fold higher likelihood for a physician assessment of response to MTX≦2 cm (good response to MTX). This is consistent with previous findings in the treatment of rheumatoid arthritis (Angelis-Stoforidis et al., *Clin. Exp. Rheumatol.* 17:313-320 (1999); Kremer et al., *Arthritis Rheum.* 29:832-835 (1986)), psoriasis (Chladek et al., *Eur. J. Clin. Pharmacol.* 53:437-444 (1998)), and cancer (Masson et al., *J. Clin. Invest.* 97:73-80 (1996); Schmiegelow et al., *J. Clin. Oncol.* 13:345-351 (1995)), and is consistent with the notion that the quantification of RBC MTXPG can be useful for practicing physicians to achieve rapid, effective dosing of MTX.

There is growing evidence that a part of the large inter-patient variability in response to xenobiotics is related to genetic polymorphisms (Evans et al., *N. Engl. J. Med.* 348: 538-549 (2003)). In the present study, the contribution of three common polymorphisms in the folate (RFC-1 G80A), de novo purine (ATIC C347G), and pyrimidine (TSER*2/*3R) synthesis pathways were evaluated for their effects on methotrexate therapy.

Recent evidence suggests that the G80A polymorphism in RFC-1 is associated with altered folate/anti-folate levels and modestly with the risk of neural tube defects (Chango et al., *Mol. Genet. Metab.* 70:310-315 (2000); Shaw et al., *Am. J. Med. Genet.* 108:1-6 (2002); Morin et al., *Mol. Genet. Metab.* 79:197-200 (2003)). Data suggest that individuals carrying the homozygous mutant 80A/A genotype tend to present higher plasma folate and methotrexate levels (Chango et al., *Mol. Genet. Metab.* 70:310-315 (2000); Layerdiere et al., *Blood* 100:3832-3834 (2002)) and higher red blood cells folate polyglutamate levels compared to those with the non-homozygous mutant genotype (Shaw et al., *Am. J. Med. Genet.* 108:1-6 (2002)). This latter finding is consistent with the observation that individuals as carriers of the RFC-1 homozygous mutant genotype presented a 2-fold higher frequency of MTXPG above 60 nmol/L compared to those with the non-homozygous mutant genotype. It is tempting to suggest that this contributed to the lower disease activity and improved patients assessment of disability (lower mHAQ) in individuals with the 80A/A genotype compared to those with the non-homozygous genotype. However, the polymorphism could also directly impact disease activity and patients self assessment through more subtle alteration in folate homeostasis (Chango et al., *Mol. Genet. Metab.* 70:310-315 (2000); Whetstine et al., *Clin. Cancer Res.* 7:3416-3422 (2001)).

Previous in vitro reports have demonstrated that activation of T lymphocytes is associated with the de novo synthesis of purine and pyrimidine which leads to a 2-fold purine and up to an 8-fold pyrimidine pool expansion over 72, respectively (Fairbanks et al., *J. Biol. Chem.* 270:29682-29689 (1995)). Furthermore, evidence suggests that part of the mechanism of action of MTX in rheumatoid arthritis is associated with an apoptosis signal that is triggered by the purineless and pyrimidineless state induced (Quemeneur et al., *J. Immunol.* 170: 4986-4995 (2003); Genestier et al., *J. Clin. Invest.* 102:322-328 (1998)).

Investigators have previously demonstrated that an inhibition of the de novo purine synthesis pathway is an important component of the mechanism of MTX (Dervieux et al., *Blood* 100:1240-1247 (2002); Baggott et al., *Biochem. J.* 236:193-200 (1986)). For example, MTXPGs are inhibitors of ATIC, a bifunctional enzyme that catalyzes the penultimate and final steps in the de novo purine nucleotide biosynthetic pathway (Rayl et al., *J. Biol. Chem.* 271:2225-2233 (1996)). The result is accumulation of AICAR and release of the anti-inflammatory agent, adenosine (Morabito et al., *J. Clin. Invest.* 101: 295-300 (1998); Montesinos et al., *Arthritis Rheum.* 48:240-247 (2003); Cronstein et al., *J. Clin. Invest.* 92:2675-2682 (1993)). In the present study, the contribution of a threonine to serine substitution at position 116 of ATIC (C347G) to the effects of methotrexate was investigated and the data indicate that patients carrying the 347G variant may have an increased likelihood of response to MTX. These data are consistent with the hypothesis that MTX may produce part of its anti-inflammatory effects through inhibition of de novo purine synthesis. The SNPs decrease the enzymatic activity of ATIC, thereby increasing the intracellular pools for the purine precursor AICAR.

Previous studies have demonstrated that thymidylate synthase (TS) increases 10-fold 48 h after activation of T lymphocytes (Feder et al., *J. Cell. Biol.* 111:2693-2701 (1990)) and evidence suggests that increasing the number of tandem repeats in the TS promoter is associated with increased TS expression and decreased efficacy to 5-fluorouracil and methotrexate (Villafranca et al., *J. Clin. Oncol.* 19:1779-1786 (2001); Krajinovic et al., *Lancet* 359:1033-1034 (2002); Marsh et al., *Int. J. Oncol.* 19:383-386 (2001); Kumagai et al., *Int. J. Mol. Med.* 11:593-600 (2003)). In the present study, an increased number of TSER*2 alleles was associated with lower disease activity and improved response to methotrexate. Therefore, the data are in agreement with previous observations and suggest that inhibition of pyrimidine synthesis is part of mechanism of action of methotrexate in rheumatoid arthritis.

Because these common polymorphisms under investigation presented an overall low phenotypic penetrance, we considered that a pharmacogenetic index calculated as the summation of these genetic variations may improve the level of association with MTX's effects. The data revealed that increased pharmacogenetic index was associated with increased effect to MTX therapy and patients having a pharmacogenetic index above 2 were 4.7 fold more likely to present a good response to MTX therapy. Interestingly, the contribution of the pharmacogenetic index the effect of MTX was evident at low concentration of MTXPGs while increased MTXPGs concentrations tended to overcome the contribution of these polymorphisms to the inter-patient variability in MTX effects. This later observation is of interest and can have direct applications in clinical practice, as individuals with no homozygous mutant genotypes (score of 0, 56% of patients) and having low MTXPG levels may require more aggressive treatment to maximize polyglutamation and effects. This would be a cost effective alternative before considering other medications such as TNF alpha antagonists.

We conclude that MTXPGs and genetic variations in the folate/purine/pyrimidine pathways contribute to the effects of MTX and can be useful to individualize MTX therapy.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for optimizing therapeutic efficacy of methotrexate (MTX) therapy in an individual receiving MTX, wherein said individual has an autoimmune disease, said method comprising:
determining the concentration level of $MTXPG_3$ in a red blood cell sample from said individual, wherein a concentration level of said $MTXPG_3$ less than about 60 nmol/L is indicative of a need to increase the amount of MTX subsequently administered to said individual.

2. The method of claim 1, wherein said individual has rheumatoid arthritis.

3. The method of claim 1, wherein said $MTXPG_3$ is resolved chromatographically.

4. The method of claim 3, wherein the concentration level of said $MTXPG_3$ is determined using a technique selected from the group consisting of fluorimetry, spectrophotometry, and mass spectrometry.

5. A method for determining clinical responsiveness to methotrexate (MTX) therapy in an individual receiving MTX, wherein said individual has an autoimmune disease, said method comprising:
determining the concentration level of $MTXPG_3$ in a red blood cell sample from said individual, wherein a concentration level of said $MTXPG_3$ greater than about 60 nmol/L is indicative of superior clinical responsiveness to said MTX therapy.

6. The method of claim 5, wherein said individual has rheumatoid arthritis.

7. The method of claim 5, wherein said $MTXPG_3$ is resolved chromatographically.

8. The method of claim 7, wherein the concentration level of said $MTXPG_3$ is determined using a technique selected from the group consisting of fluorimetry, spectrophotometry, and mass spectrometry.

9. A method for determining clinical responsiveness to methotrexate (MTX) therapy in an individual receiving MTX, wherein said individual has an autoimmune disease, said method comprising:
determining the concentration level of $MTXPG_3$ in a red blood cell sample from said individual, wherein a concentration level of said $MTXPG_3$ less than about 40 nmol/L is indicative of inferior clinical responsiveness to said MTX therapy.

10. The method of claim 9, wherein said individual has rheumatoid arthritis.

11. The method of claim 9, wherein said $MTXPG_3$ is resolved chromatographically.

12. The method of claim 11, wherein the concentration level of said $MTXPG_3$ is determined using a technique selected from the group consisting of fluorimetry, spectrophotometry, and mass spectrometry.

13. The method of claim 1, 5, or 9, wherein $MTXPG_3$ is resolved by HPLC.

14. A method for optimizing therapeutic efficacy of methotrexate (MTX) therapy in an individual receiving MTX, wherein said individual has an autoimmune disease, said method comprising:
determining the concentration level of $MTXPG_{3-5}$ in a red blood cell sample from said individual, wherein a concentration level of said $MTXPG_{3-5}$ less than about 90 nmol/L is indicative of a need to optimize said MTX therapy.

15. The method of claim 14, wherein said individual has rheumatoid arthritis.

16. The method of claim 14, wherein said $MTXPG_{3-5}$ is resolved chromatographically.

17. The method of claim 14, wherein said $MTXPG_{3-5}$ is resolved by HPLC.

18. The method of claim 16, wherein the concentration level of said $MTXPG_{3-5}$ is determined using a technique selected from the group consisting of fluorimetry, spectrophotometry, and mass spectrometry.

19. A method for determining clinical responsiveness to methotrexate (MTX) therapy in an individual receiving MTX, wherein said individual has an autoimmune disease, said method comprising:
determining the concentration level of $MTXPG_{3-5}$ in a red blood cell sample from said individual, wherein a concentration level of said $MTXPG_{3-5}$ greater than about 90 nmol/L is indicative of clinical responsiveness to said MTX therapy.

20. The method of claim 19, wherein said individual has rheumatoid arthritis.

21. The method of claim 19, wherein said $MTXPG_{3-5}$ is resolved chromatographically.

22. The method of claim 19, wherein said $MTXPG_{3-5}$ is resolved by HPLC.

23. The method of claim 21, wherein the concentration level of said $MTXPG_{3-5}$ is determined using a technique selected from the group consisting of fluorimetry, spectrophotometry, and mass spectrometry.

24. A method for determining clinical responsiveness to methotrexate (MTX) therapy in an individual receiving MTX, wherein said individual has an autoimmune disease, said method comprising:
determining the concentration level of $MTXPG_{3-5}$ in a red blood cell sample from said individual, wherein a concentration level of said $MTXPG_{3-5}$ less than about 55 nmol/L is indicative of inferior clinical responsiveness to said MTX therapy.

25. The method of claim 24, wherein said individual has rheumatoid arthritis.

26. The method of claim 24, wherein said $MTXPG_{3-5}$ is resolved chromatographically.

27. The method of claim 24, wherein said MTXPG$_{3-5}$ is resolved by HPLC.

28. The method of claim 26, wherein the concentration level of said MTXPG$_{3-5}$ is determined using a technique selected from the group consisting of fluorimetry, spectrophotometry, and mass spectrometry.

* * * * *

UNITED STATES PATENT AND TRADEMARK OFFICE
CERTIFICATE OF CORRECTION

| | | |
|---|---|---|
| PATENT NO. | : 7,582,282 B2 | Page 1 of 1 |
| APPLICATION NO. | : 10/927904 | |
| DATED | : September 1, 2009 | |
| INVENTOR(S) | : Dervieux et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1008 days.

Signed and Sealed this

Fifteenth Day of March, 2011

David J. Kappos
*Director of the United States Patent and Trademark Office*